United States Patent [19]

Kavanaugh et al.

[11] Patent Number: 6,090,621
[45] Date of Patent: Jul. 18, 2000

[54] SIGNALING INOSITOL POLYPHOSPHATE 5-PHOSPHATASES (SIPS)

[75] Inventors: W. Michael Kavanaugh, Mill Valley; David Pot, San Francisco; Lewis T. Williams, Tiburon, all of Calif.

[73] Assignee: Chiron Corporation, Emeryville, Calif.

[21] Appl. No.: 09/195,868

[22] Filed: Nov. 19, 1998

Related U.S. Application Data

[60] Division of application No. 08/759,397, Dec. 4, 1996, which is a continuation-in-part of application No. 08/569,578, Dec. 8, 1995, abandoned, and application No. 08/624,190, Mar. 28, 1996, abandoned.
[60] Provisional application No. 60/008,606, Dec. 14, 1995.

[51] Int. Cl.[7] .................................................. C12N 5/06
[52] U.S. Cl. .......................... 435/338; 435/7.1; 435/21; 435/331; 435/346; 530/388.1; 530/388.15; 530/388.26
[58] Field of Search .................... 435/4, 7.1, 21, 435/331, 338, 346; 530/350, 324, 352, 388.1, 388.15, 388.26

[56] References Cited

U.S. PATENT DOCUMENTS 4,543,439  9/1985  Frackelton et al. ...................... 935/92
4,946,778  8/1990  Ladner et al. ......................... 435/69.6

OTHER PUBLICATIONS

Queen et al. "A Humanized Antibody That Binds to the Interleukin 2 Receptor", *Proceedings of the National Academy of Science,* vol. 86, (Dec. 1989), pp. 10029–10033.

*Primary Examiner*—Jeffrey Stucker
*Attorney, Agent, or Firm*—Roberta L. Robins; Kimberlin L. Morley; Robert P. Blackburn

[57] ABSTRACT

Novel polypeptides called signaling inositol polyphosphate 5-phosphatases are described called SIP-130, SIP-125, and SIP-N. SIP-130 is capable of binding to aPTB domain of SH2 and collagen containing protein (SHC). Also provided are polynucleotide sequences encoding the novel polypeptides, as well as vectors and host cells containing the polynucleotides. Further provided are modulators including agonists and antagonists of the novel polypeptides for use as therapeutics, including antibodies, polypeptides, small molecules, and polynucleotides and methods of using the therapeutics in treatment of diseases associated with abnormal cell growth. Methods of making the polypeptides, polynucleotides, vectors, host cells, antibodies, and small molecules are also provided. Gene delivery vehicles including SIP and SIP activity-modulating polynucleotides are described.

6 Claims, 5 Drawing Sheets

```
TGGAGGGGCCCTCCGCTCCCCCTCGTGGTGTGGGTCCTGCCTGCCTCCGGCCCCGAGGAGCCACGCCCACC        121
V  E  G  P  P  L  P  S  V  V  C  G  S  W  G  C  L  P  A  R  P  R  R  P  T  P  T          40

ATG TCCCCTGCTGAACCATGGCAACATCACCCGCTCAAGGCTGCTTTCCAGGACAGGCAAGGACGGA
 M   V  P  C  W  N  H  G  N  I  T  R  S  K  A  E  E  L  L  S  R  T  G  K  D  G

GCTTCCTCGTGCGTGCCAGGAGTCCATCTCCCGGGCATACGCGCTCTGCGTGTATCGGAATTGCGTTTACACTTAC        280
 S  F  L  V  R  A  S  E  S  I  S  R  A  Y  A  L  C  V  L  Y  R  N  C  V  Y  T  Y         93

AGAATTCTGCCCAATGAAGATGATAAATTCACTGTTCAGGCATCCGAAGGCGTCTCCATGAGGTTCTTCACCAAGCTGG
 R  I  L  P  N  E  D  D  K  F  T  V  Q  A  S  E  G  V  S  M  R  F  F  T  K  L

ACCAGCTCATCGAGTTTTACAAGAAGGAGAACATGGGGCTGGTGACCCATCTGCAATACCCTGTGCCGCTGGAGGAAGAG        439
 D  Q  L  I  E  F  Y  K  K  E  N  M  G  L  V  T  H  L  Q  Y  P  V  P  L  E  E  E        146

GACACAGGCGACGACCCTGAGGAGGACACAGTAGAAAGTGTCGTGTCTCCACCCGAGCTGCCCCCAAGAAACATCCCGC
 D  T  G  D  D  P  E  E  D  T  V  E  S  V  V  S  P  P  E  L  P  P  R  N  I  P

TGACTGCCAGTCCCTGTGAGGCCAAGGAGGTTCCTTTTCAAACGAGAATCCCGAGGCGACCGAGACCAGCCGGCCGAGC        598
 L  T  A  S  S  C  E  A  K  E  V  P  F  S  N  E  N  P  R  A  T  E  T  S  R  P  S        199

CTCTCCGAGACATTGTTCCAGCGACTGCAAAGCATGGACACCAGTGGCTTCCAGAAGAGCATCTTAAGGCCATCCAAG
 L  S  E  T  L  F  Q  R  L  Q  S  M  D  T  S  G  L  P  E  E  H  L  K  A  I  Q
                                                                         A  I  Q

ATTATTTAAGCACTCAGCTGCCCCAGGACTCTGAATTTGTGAAGACAGGGTCCAGCAGTCTTCCTCACCTGAAGAAACTG        757
 D  Y  L  S  T  Q  L  A  Q  D  S  E  F  V  K  T  G  S  S  S  L  P  H  L  K  K  L        252
 D  Y  L  S  T  Q  L  L  D  S  D  F  L  K

ACCACACTGCTCTGCAAGGAGCTCTATGGA 787
 T  T  L  C  K  E  L  Y  G  262

TAA TCCCTTGATGTTCACCTTGTCCCCTGCCCCCAGAGAAGTCATCCGGACCCTCCATCCCTGGAGTCTCTGCAGAGGT
 M  F  T  L  S  P  A  P  R  E  V  I  R  T  L  P  S  L  E  S  L  Q  R
```

FIG. 1A

```
TATTTGACCAGCAGCTCTCCCGGGCCTCCGTCTTCCAGTTCCTGGTGAGGCCAATCCCATCAACATGGTGTCC  159
 L  F  D  Q  Q  L  S  P  G  L  R  R  P  Q  V  P  G  E  A  N  P  I  N  M  V  S   50

AAGCTCAGCCAACTGACAAGCCTGTTGTCATCCATTGAAGACAAGGTCAAGGCCTTGCTGCACGAGGGTCCTGAGTCTC  318
 K  L  S  Q  L  T  S  L  L  S  S  I  E  D  K  V  K  A  L  L  H  E  G  P  E  S   103
                 *L* *S* *Q* *L* *T* *S* *L* *L* *S* *S* *I* *E* *D* *K*

CGCACCGGCCCCTCCCTTATCCCTCCAGTCACCTTTGAGGTGAAGGCAGAGTCTCTGGGGATTCCTCAGAAAATGCAGCTC  318
 P  H  R  P  S  L  I  P  P  V  T  F  E  V  K  A  E  S  L  G  I  P  Q  K  M  Q  L

AAAGTCGACGTTGAGTCTGGGAAACTGATCATTAAGAAGTCCAAGGATGGTTCTGAGGACAAGTTCTACAGCCACAAGA  477
 K  V  D  V  E  S  G  K  L  I  I  K  K  S  K  D  G  S  E  D  K  F  Y  S  H  K   156

AAATCCTGCAGCTCATTAAGTCACAGAAATTTCTGAATAAGTTGGTGATCTTGGTGAAACAGAGAAGGAGAAGATCCTG  477
 K  I  L  Q  L  I  K  S  Q  K  F  L  N  K  L  V  I  L  V  E  T  E  K  E  K  I  L
                                            *L* *V* *I* *L* *V* *E* *T* *E* *K*

CGGAAGGAATATGTTTTTGCTGACTCCAAAAAGAGAGAAGGCTTCTGCCAGCTCCTGCAGCAGATGAAGAACAAGCACT  636
 R  K  E  Y  V  F  A  D  S  K  K  R  E  G  F  C  Q  L  L  Q  Q  M  K  N  K  H

CAGAGCAGCCGGAGCCCGACATGATCACCATTCATCGGCACCTGGAACATGGTAACGCCCCCCCCAAGAAGATC  636
 S  E  Q  P  E  P  D  M  I  T  F  I  G  T  W  N  M  G  N  A  P  P  P  K  K  I   209

ACGTCCTGGTTTCTCTCCAAGGGCAGGGAAAGACGCGGGACGACTCTGCGACTACATCCCCATGACATTTACGTGA  795
 T  S  W  F  L  S  K  G  Q  G  K  T  R  D  D  S  A  D  Y  I  P  H  D  I  Y  V
                                *T* *R* *D* *D* *S* *X* *X* *Y* *I* *P*

TCGGCACCCAAGAGACCCCCTGAGTGAGAAGGAGTGGCTGGAGAATCCTCAAACACTCCTGCAAGAAATCACCAGTGTG  795
 I  G  T  Q  E  D  P  L  S  E  K  E  W  L  E  I  L  K  H  S  L  Q  E  I  T  S  V   262

ACTTTTAAAACAGTCGCCATCCACACGCTCTGGAACATCCGATCGTGGTGCTGGCCAAGCCTGAGCACGAGAACCGGA  954
 T  F  K  T  V  A  I  H  T  L  W  N  I  R  I  V  V  L  A  K  P  E  H  E  N  R

TCAGCCACATCTGTACTGACAACGTGAAGACAGGCATTGCAAACACTGGGAACAAGGAGCCGTGGGGTGTCGTTC  954
 I  S  H  I  C  T  D  N  V  K  T  G  I  A  N  T  L  G  N  K  G  A  V  G  V  S  F   315

ATGTTCAATGGAACCTCCTTAGGGTTCGTCAACAGCCACTTGACTTCAGGAAGTGAAAAGAAACTCAGGCGAAACCAAA
 M  F  N  G  T  S  L  G  F  V  N  S  H  L  T  S  G  S  E  K  K  L  R  R  N  Q
```

```
TTCCAGGGGAGATCAAGCTGCAGACCTCTCAGGGCAAGACGGAGAAGCTCTATGACTTTGTGAAGACGGAGCGTG
 F  Q  G  E  I  K  L  Q  T  S  Q  G  K  T  R  E  K  L  Y  D  F  V  K  T  E  R

ATGAATCCAGTGGGCCAAAGACCCTGAAGACCCACCAGCCACGACCCATGAAGCAGTGGGAAGTCACTAGCAGGGCC   2067
 M  N  P  V  G  Q  R  P  L  K  T  H  Q  P  R  P  M  K  Q  W  E  V  T  S  R  A    686

CCTCCGTGCAGTGGCTCCAGCATCACTGAAATCATCAACCCCAACTACATGGGAGTGGGCCCCTTTGGGCCACCAATGC
 P  P  C  S  G  S  S  I  T  E  I  I  N  P  N  Y  M  G  V  G  P  F  G  P  P  M

CCCTGCACGTGAAGCAGACCTTGTCCCCTGACCAGCAGCCCACAGCCTGGAGCTACGACCAGCCGCCCAAGGACTCCCCG   2226
 P  L  H  V  K  Q  T  L  S  P  D  Q  Q  P  T  A  W  S  Y  D  Q  P  P  K  D  S  P    739

CTGGGCCCTGCAGGGGAGAAAGTCCTCCGACACCTCCCGGCCAGCCCCATATCACCCAAGAAGTTTTTACCCTCAA
 L  G  P  C  R  G  E  S  P  P  T  P  P  G  Q  P  P  I  S  P  K  K  F  L  P  S

CAGCAAACCGGGGTCTCCCCTCCCAGGACACAGGAGTCAAGGCCCAGTGACCTGGGAAGAACGCAGGGACACGCTGCCT   2385
 Q  Q  T  G  V  S  P  P  R  T  Q  E  S  R  P  S  D  L  G  K  N  A  G  D  T  L  P    792
 T  A  N  R  G  L  P  P  R  T  Q  E  S  R  P  S  D  L  G  K  N  A  G  D  T  L  P
                                                                  G  X  X  L  X

CAGGAGGACCTGCCGCTGACGAAGCCCGAGATGTTTGAGAACCCCCTGTATGGGTCCCTGAGTTCCTTCCCTAAGCCTG
 Q  E  D  L  P  L  T  K  P  E  M  F  E  N  P  L  Y  G  S  L  S  S  F  P  K  P
 Q  E  D  L  X  L  T  K  P  P  E  M  X  E  N  X  L

CTCCCCAGGAAGGACCAGGAATCCCCCAAAATGCCGCGGAAGAAGGAACCCCCTGCCCGGAACCCGGCATCTTGTCGCCC   2544
 A  P  R  K  D  Q  E  S  P  K  M  P  R  K  E  P  P  P  C  P  E  P  G  I  L  S  P    845
 E  P  P  X  C  P  D  D  P  G  I  L  X  P

AGCATCGTGCTCACCAAAGCCCAGGAGGCTGATCGCGGAGAAGGGCCCGGGAAGCAGGTGCCCGCGCCCCGGCTGCGT
 S  I  V  L  T  K  A  Q  E  A  D  R  G  E  G  P  G  K  Q  V  P  A  P  R  L  R
 X  I

CCTTCACGTGCTCATCCTCTGCCAAGAGGCGGAAGGGGACAAGAGCCAAGGAAGCCAAGAGCCCGTCAGC   2703
 S  F  T  C  S  S  A  E  G  R  A  A  G  G  D  K  S  Q  G  K  P  K  T  P  V  S    898

TCCCAGGCCCCGGTGCCCGGCCAAGAGGCCTTCCAGATCGGAAATCAACCAGCAGCCCGCAGACCCCGA
 S  Q  A  P  V  P  A  K  R  P  I  K  P  S  R  E  I  N  Q  Q  T  P  P  T  P
```

FIG. 1D

```
CGCCGCGGCCGCCGCTGCCAGTCAAGAGCCCGGCTGTGCACCTCCAGCACTCCAAGGCCCGGCGACTACCGCGACAAC  2862
T   P   R   P   P   L   P   V   K   S   P   A   V   L   H   L   Q   H   S   K   G   R   D   Y   R   D   N    951

ACCGAGCTCCCGGATCACGGCAAGCACCGGCCCGAGGAGGGGCCACCAGGCCCTCTAGGCAGGACTGCCATGCAGTGA  2940
T   E   L   P   H   H   G   K   H   R   P   E   E   G   P   P   G   P   L   G   R   T   A   M   Q   *    976
```

FIG. 1E

```
                          SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Thr Arg Asp Asp Ser Ala Asp Tyr Ile Pro
1               5                   10

(2) INFORMATION FOR SEQ ID NO:2:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Pro Ile Ile Ser Asp Pro Glu Tyr Leu Leu Asp Gln His Ile Leu Ile
1               5                   10                  15

Ser Ile Lys (2) INFORMATION FOR SEQ ID NO:3:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gly Asp Thr Leu Pro Gln Glu Asp Leu Pro Leu Thr Lys Pro Glu Met
1               5                   10                  15

Phe Glu Asn Pro Leu
                20

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO:4:

Glu Pro Pro Pro Cys Pro Glu Pro Gly Ile Leu Ser Pro Ser Ile
1               5                   10                  15

(2) INFORMATION FOR SEQ ID NO:5:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:5:

Thr Arg Asp Asp Ser Xaa Xaa Tyr Ile Pro
1               5                   10

(2) INFORMATION FOR SEQ ID NO:6:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:6:

Pro Ile Ile Ser Asp Pro Glu Tyr Leu Leu Asp Gln His Ile Xaa Ile
1               5                   10                  15

Xaa Xaa Lys (2) INFORMATION FOR SEQ ID NO:7:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:7:

Gly Xaa Xaa Leu Xaa Gln Glu Asp Leu Xaa Leu Thr Lys Pro Glu Met
1               5                   10                  15

Xaa Glu Asn Xaa Leu
            20

(2) INFORMATION FOR SEQ ID NO:8:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:8:

Glu Pro Pro Xaa Cys Pro Asp Pro Gly Ile Leu Xaa Pro Xaa Ile
1               5                   10                  15

(2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ala Ile Gln Asp Tyr Leu Ser Thr Gln Leu Leu Leu Asp Ser Asp Phe
1               5                  10                  15
Leu Lys
```

(2) INFORMATION FOR SEQ ID NO:10:

(i) SEQUENCE CHARACTERISTICS:
        (A) LENGTH: 787 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GCAGCCGAGG CCACCAAGAG GCAACGGGCG GCAGGTTGCA GTGGAGGGGC CTCCGCTCCC      60
CTCGGTGGTG TGTGGGTCCT GGGGGTGCCT GCCGGCCCGG CCGAGGAGGC CCACGCCCAC     120
CATGGTCCCC TGCTGGAACC ATGGCAACAT CACCCGCTCC AAGGCGGAGG AGCTGCTTTC     180
CAGGACAGGC AAGGACGGGA GCTTCCTCGT GCGTGCCAGC GAGTCCATCT CCCGGGCATA     240
CGCGCTCTGC GTGCTGTATC GGAATTGCGT TTACACTTAC AGAATTCTGC CCAATGAAGA     300
TGATAAATTC ACTGTTCAGG CATCCGAAGG CGTCTCCATG AGGTTCTTCA CCAAGCTGGA     360
CCAGCTCATC GAGTTTTACA AGAAGGAAAA CATGGGGCTG GTGACCCATC TGCAATACCC     420
TGTGCCGCTG GAGGAAGAGG ACACAGGCGA CGACCCTGAG GAGGACACAG TAGAAAGTGT     480
CGTGTCTCCA CCCGAGCTGC CCCCAAGAAA CATCCCGCTG ACTGCCAGCT CCTGTGAGGC     540
CAAGGAGGTT CCTTTTTCAA CGAGAATCC CCGAGCGACC GAGACCAGCC GGCCGAGCCT      600
CTCCGAGACA TTGTTCCAGC GACTGCAAAG CATGGACACC AGTGGGCTTC AGAAGAGCA      660
TCTTAAGGCC ATCCAAGATT ATTTAAGCAC TCAGCTCGCC CAGGACTCTG AATTTGTGAA     720
GACAGGGTCC AGCAGTCTTC CTCACCTGAA GAAACTGACC ACACTGCTCT GCAAGGAGCT     780
CTATGGA                                                              787
```

(2) INFORMATION FOR SEQ ID NO:11:

(i) SEQUENCE CHARACTERISTICS:
        (A) LENGTH: 2940 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
TAATCCTTGA TGTTCACCTT GTCCCCTGCC CCCAGAGAAG TCATCCGGAC CCTCCCATCC      60
CTGGAGTCTC TGCAGAGGTT ATTTGACCAG CAGCTCTCCC CGGGCCTCCG TCCACGTCCT     120
CAGGTTCCTG GTGAGGCCAA TCCCATCAAC ATGGTGTCCA AGCTCAGCCA ACTGACAAGC     180
CTGTTGTCAT CCATTGAAGA CAAGGTCAAG GCCTTGCTGC ACGAGGGTCC TGAGTCTCCG     240
```

-continued

```
CACCGGCCCT CCCTTATCCC TCCAGTCACC TTTGAGGTGA AGGCAGAGTC TCTGGGGATT      300

CCTCAGAAAA TGCAGCTCAA AGTCGACGTT GAGTCTGGGA AACTGATCAT TAAGAAGTCC      360

AAGGATGGTT CTGAGGACAA GTTCTACAGC CACAAGAAAA TCCTGCAGCT CATTAAGTCA      420

CAGAAATTTC TGAATAAGTT GGTGATCTTG GTGGAAACAG AGAAGGAGAA GATCCTGCGG      480

AAGGAATATG TTTTTGCTGA CTCCAAAAAG AGAGAAGGCT TCTGCCAGCT CCTGCAGCAG      540

ATGAAGAACA AGCACTCAGA GCAGCCGGAG CCCGACATGA TCACCATCTT CATCGGCACC      600

TGGAACATGG GTAACGCCCC CCCTCCCAAG AAGATCACGT CCTGGTTTCT CTCCAAGGGG      660

CAGGGAAAGA CGCGGGACGA CTCTGCGGAC TACATCCCCC ATGACATTTA CGTGATCGGC      720

ACCCAAGAGG ACCCCCTGAG TGAGAAGGAG TGGCTGGAGA TCCTCAAACA CTCCCTGCAA      780

GAAATCACCA GTGTGACTTT TAAAACAGTC GCCATCCACA CGCTCTGGAA CATCCGCATC      840

GTGGTGCTGG CCAAGCCTGA GCACGAGAAC CGGATCAGCC ACATCTGTAC TGACAACGTG      900

AAGACAGGCA TTGCAAACAC ACTGGGGAAC AAGGGAGCCG TGGGGGTGTC GTTCATGTTC      960

AATGGAACCT CCTTAGGGTT CGTCAACAGC CACTTGACTT CAGGAAGTGA AAAGAAACTC     1020

AGGCGAAACC AAAACTATAT GAACATTCTC CGGTTCCTGG CCCTGGGCGA CAAGAAGCTG     1080

AGTCCCTTTA ACATCACTCA CCGCTTCACG CACCTCTTCT GGTTTGGGGA TCTTAACTAC     1140

CGTGTGGATC TGCCTACCTG GGAGGCAGAA ACCATCATCC AGAAAATCAA GCAGCAGCAG     1200

TACGCAGACC TCCTGTCCCA CGACCAGCTG CTCACAGAGA GGAGGGAGCA GAAGGTCTTC     1260

CTACACTTCG AGGAGGAAGA AATCACGTTT GCCCCAACCT ACCGTTTTGA GAGACTGACT     1320

CGGGACAAAT ACGCCTACAC CAAGCAGAAA GCGACAGGGA TGAAGTACAA CTTGCCTTCC     1380

TGGTGTGACC GAGTCCTCTG GAAGTCTTAT CCCCTGGTGC ACGTGGTGTG TCAGTCTTAT     1440

GGCAGTACCA GCGACATCAT GACGAGTGAC CACAGCCCTG TCTTTGCCAC ATTTGAGGCA     1500

GGAGTCACTT CCCAGTTTGT CTCCAAGAAC GGTCCCGGGA CTGTTGACAG CCAAGGACAG     1560

ATTGAGTTTC TCAGGTGCTA TGCCACATTG AAGACCAAGT CCCAGACCAA ATTCTACCTG     1620

GAGTTCCACT CGAGCTGCTT GGAGAGTTTT GTCAAGAGTC AGGAAGGAGA AAATGAAGAA     1680

GGAAGTGAGG GGGAGCTGGT GGTGAAGTTT GGTGAGACTC TTCCAAAGCT GAAGCCCATT     1740

ATCTCTGACC CTGAGTACCT GCTAGACCAG CACATCCTCA TCAGCATCAA GTCCTCTGAC     1800

AGCGACGAAT CCTATGGCGA GGGCTGCATT GCCCTTCGGT TAGAGGCCAC AGAAACGCAG     1860

CTGCCCATCT CACGCCTCT CACCCACCAT GGGGAGTTGA CAGGCCACTT CCAGGGGGAG     1920

ATCAAGCTGC AGACCTCTCA GGGCAAGACG AGGGAGAAGC TCTATGACTT TGTGAAGACG     1980

GAGCGTGATG AATCCAGTGG GCCAAAGACC CTGAAGAGCC TCACCAGCCA CGACCCCATG     2040

AAGCAGTGGG AAGTCACTAG CAGGGCCCCT CCGTGCAGTG GCTCCAGCAT CACTGAAATC     2100

ATCAACCCCA ACTACATGGG AGTGGGCCCC TTTGGGCCAC CAATGCCCCT GCACGTGAAG     2160

CAGACCTTGT CCCCTGACCA GCAGCCCACA GCCTGGAGCT ACGACCAGCC GCCCAAGGAC     2220

TCCCCGCTGG GGCCTGCAG GGGAGAAAGT CCTCCGACAC CTCCCGGCCA GCCGCCCATA     2280

TCACCCAAGA AGTTTTTACC CTCAACAGCA AACCGGGGTC TCCCTCCCAG GACACAGGAG     2340

TCAAGGCCCA GTGACCTGGG GAAGAACGCA GGGGACACGC TGCCTCAGGA GGACCTGCCG     2400

CTGACGAAGC CCGAGATGTT TGAGAACCCC CTGTATGGGT CCCTGAGTTC CTTCCCTAAG     2460

CCTGCTCCCA GGAAGGACCA GGAATCCCCC AAAATGCCGC GGAAGGAACC CCCGCCCTGC     2520

CCGGAACCCG GCATCTTGTC GCCCAGCATC GTGCTCACCA AAGCCCAGGA GGCTGATCGC     2580

GGCGAGGGGC CCGGCAAGCA GGTGCCCGCG CCCCGGCTGC GCTCCTTCAC GTGCTCATCC     2640
```

-continued

```
TCTGCCGAGG GCAGGGCGGC CGGCGGGGAC AAGAGCCAAG GGAAGCCCAA GACCCCGGTC        2700

AGCTCCCAGG CCCCGGTGCC GGCCAAGAGG CCCATCAAGC CTTCCAGATC GGAAATCAAC        2760

CAGCAGACCC CGCCCACCCC GACGCCGCGG CCGCCGCTGC CAGTCAAGAG CCCGGCGGTG        2820

CTGCACCTCC AGCACTCCAA GGGCCGCGAC TACCGCGACA ACACCGAGCT CCCGCATCAC        2880

GGCAAGCACC GGCCGGAGGA GGGGCCACCA GGGCCTCTAG GCAGGACTGC CATGCAGTGA        2940
```

(2) INFORMATION FOR SEQ ID NO:12:

(i) SEQUENCE CHARACTERISTICS:
        (A) LENGTH: 3691 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GCAGCCGAGG CCACCAAGAG GCAACGGGCG GCAGGTTGCA GTGGAGGGGC CTCCGCTCCC          60

CTCGGTGGTG TGTGGGTCCT GGGGGTGCCT GCCGGCCCGG CCGAGGAGGC CCACGCCCAC         120

CATGGTCCCC TGCTGGAACC ATGGCAACAT CACCCGCTCC AAGGCGGAGG AGCTGCTTTC         180

CAGGACAGGC AAGGACGGGA GCTTCCTCGT GCGTGCCAGC GAGTCCATCT CCCGGGCATA         240

CGCGCTCTGC GTGCTGTATC GGAATTGCGT TTACACTTAC AGAATTCTGC CCAATGAAGA         300

TGATAAATTC ACTGTTCAGG CATCCGAAGG CGTCTCCATG AGGTTCTTCA CCAAGCTGGA         360

CCAGCTCATC GAGTTTTACA AGAAGGAAAA CATGGGGCTG GTGACCCATC TGCAATACCC         420

TGTGCCGCTG GAGGAAGAGG ACACAGGCGA CGACCCTGAG GAGGACACAG TAGAAAGTGT         480

CGTGTCTCCA CCCGAGCTGC CCCCAAGAAA CATCCCGCTG ACTGCCAGCT CCTGTGAGGC         540

CAAGGAGGTT CCTTTTTCAA ACGAGAATCC CCGAGCGACC GAGACCAGCC GGCCGAGCCT         600

CTCCGAGACA TTGTTCCAGC GACTGCAAAG CATGGACACC AGTGGGCTTC AGAAGAGCA         660

TCTTAAGGCC ATCCAAGATT ATTTAAGCAC TCAGCTCGCC CAGGACTCTG AATTTGTGAA         720

GACAGGGTCC AGCAGTCTTC CTCACCTGAA GAAACTGACC ACACTGCTCT GCAAGGAGCT         780

CTATGGAGAA GTCATCCGGA CCCTCCCATC CCTGGAGTCT CTGCAGAGGT TATTTGACCA         840

GCAGCTCTCC CCGGGCCTCC GTCCACGTCC TCAGGTTCCT GGTGAGGCCA ATCCCATCAA         900

CATGGTGTCC AAGCTCAGCC AACTGACAAG CCTGTTGTCA TCCATTGAAG ACAAGGTCAA         960

GGCCTTGCTG CACGAGGGTC CTGAGTCTCC GCACCGGCCC TCCCTTATCC CTCCAGTCAC        1020

CTTTGAGGTG AAGGCAGAGT CTCTGGGGAT TCCTCAGAAA ATGCAGCTCA AAGTCGACGT        1080

TGAGTCTGGG AAACTGATCA TTAAGAAGTC CAAGGATGGT TCTGAGGACA AGTTCTACAG        1140

CCACAAGAAA ATCCTGCAGC TCATTAAGTC ACAGAAATTT CTGAATAAGT GGTGATCTT         1200

GGTGGAAACA GAGAAGGAGA AGATCCTGCG GAAGGAATAT GTTTTTGCTG ACTCCAAAAA        1260

GAGAGAAGGC TTCTGCCAGC TCCTGCAGCA GATGAAGAAC AAGCACTCAG AGCAGCCGGA        1320

GCCCGACATG ATCACCATCT TCATCGGCAC CTGGAACATG GGTAACGCCC CCCTCCCAA         1380

GAAGATCACG TCCTGGTTTC TCTCCAAGGG GCAGGGAAAA ACGCGGGACG ACTCTGCGGA        1440

CTACATCCCC CATGACATTT ACGTGATCGG CACCCAAGAG GACCCCCTGA GTGAGAAGGA        1500

GTGGCTGGAG ATCCTCAAAC ACTCCCTGCA AGAAATCACC AGTGTGACTT TTAAAACAGT        1560

CGCCATCCAC ACGCTCTGGA ACATCCGCAT CGTGGTGCTG GCCAAGCCTG AGCACAGAAA        1620

CCGGATCAGC CACATCTGTA CTGACAACGT GAAGACAGGC ATTGCAAACA CACTGGGGAA        1680
```

```
CAAGGGAGCC GTGGGGGTGT CGTTCATGTT CAATGGAACC TCCTTAGGGT TCGTCAACAG    1740

CCACTTGACT TCAGGAAGTG AAAAGAAACT CAGGCGAAAC CAAAACTATA TGAACATTCT    1800

CCGGTTCCTG GCCCTGGGCG ACAAGAAGCT GAGTCCCTTT AACATCACTC ACCGCTTCAC    1860

GCACCTCTTC TGGTTTGGGG ATCTTAACTA CCGTGTGGAT CTGCCTACCT GGGAGGCAGA    1920

AACCATCATC CAGAAAATCA AGCAGCAGCA GTACGCAGAC CTCCTGTCCC ACGACCAGCT    1980

GCTCACAGAG AGGAGGGAGC AGAAGGTCTT CCTACACTTC GAGGAGGAAG AAATCACGTT    2040

TGCCCCAACC TACCGTTTTG AGAGACTGAC TCGGGACAAA TACGCCTACA CCAAGCAGAA    2100

AGCGACAGGG ATGAAGTACA ACTTGCCTTC CTGGTGTGAC CGAGTCCTCT GGAAGTCTTA    2160

TCCCCTGGTG CACGTGGTGT GTCAGTCTTA TGGCAGTACC AGCGACATCA TGACGAGTGA    2220

CCACAGCCCT GTCTTTGCCA CATTTGAGGC AGGAGTCACT TCCCAGTTTG TCTCCAAGAA    2280

CGGTCCCGGG ACTGTTGACA GCCAAGGACA GATTGAGTTT CTCAGGTGCT ATGCCACATT    2340

GAAGACCAAG TCCCAGACCA AATTCTACCT GGAGTTCCAC TCGAGCTGCT TGGAGAGTTT    2400

TGTCAAGAGT CAGGAAGGAG AAAATGAAGA AGGAAGTGAG GGGGAGCTGG TGGTGAAGTT    2460

TGGTGAGACT CTTCCAAAGC TGAAGCCCAT TATCTCTGAC CCTGAGTACC TGCTAGACCA    2520

GCACATCCTC ATCAGCATCA AGTCCTCTGA CAGCGACGAA TCCTATGGCG AGGGCTGCAT    2580

TGCCCTTCGG TTAGAGGCCA CAGAAACGCA GCTGCCCATC TACACGCCTC TCACCCACCA    2640

TGGGGAGTTG ACAGGCCACT TCCAGGGGGA GATCAAGCTG CAGACCTCTC AGGGCAAGAC    2700

GAGGGAGAAG CTCTATGACT TTGTGAAGAC GGAGCGTGAT GAATCCAGTG GGCCAAAGAC    2760

CCTGAAGAGC CTCACCAGCC ACGACCCCAT GAAGCAGTGG GAAGTCACTA GCAGGGCCCC    2820

TCCGTGCAGT GGCTCCAGCA TCACTGAAAT CATCAACCCC AACTACATGG GAGTGGGCCC    2880

CTTTGGGCCA CCAATGCCCC TGCACGTGAA GCAGACCTTG TCCCCTGACC AGCAGCCCAC    2940

AGCCTGGAGC TACGACCAGC CGCCCAAGGA CTCCCCGCTG GGGCCCTGCA GGGGAGAAAG    3000

TCCTCCGACA CCTCCCGGCC AGCCGCCCAT ATCACCCAAG AAGTTTTTAC CCTCAACAGC    3060

AAACCGGGGT CTCCCTCCCA GGACACAGGA GTCAAGGCCC AGTGACCTGG GGAAGAACGC    3120

AGGGGACACG CTGCCTCAGG AGGACCTGCC GCTGACGAAG CCCGAGATGT TTGAGAACCC    3180

CCTGTATGGG TCCCTGAGTT CCTTCCCTAA GCCTGCTCCC AGGAAGGACC AGGAATCCCC    3240

CAAAATGCCG CGGAAGGAAC CCCCGCCCTG CCCGGAACCC GGCATCTTGT CGCCCAGCAT    3300

CGTGCTCACC AAAGCCCAGG AGGCTGATCG CGGCGAGGGG CCCGGCAAGC AGGTGCCCGC    3360

GCCCCGGCTG CGCTCCTTCA CGTGCTCATC CTCTGCCGAG GGCAGGGCGG CCGGCGGGGA    3420

CAAGAGCCAA GGGAAGCCCA AGACCCCGGT CAGCTCCCAG GCCCCGGTGC CGGCCAAGAG    3480

GCCCATCAAG CCTTCCAGAT CGGAAATCAA CCAGCAGACC CCGCCCACCC CGACGCCGCG    3540

GCCGCCGCTG CCAGTCAAGA GCCCGGCGGT GCTGCACCTC CAGCACTCCA AGGGCCGCGA    3600

CTACCGCGAC AACACCGAGC TCCCGCATCA CGGCAAGCAC CGGCCGGAGG AGGGGCCACC    3660

AGGGCCTCTA GGCAGGACTG CCATGCAGTG A                                  3691
```

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Ala Ile Gln Asp Tyr Leu Ser Thr Gln Leu Ala Gln Asp Ser Glu Phe
1               5                   10                  15

Val Lys (2) INFORMATION FOR SEQ ID NO:14:

(i) SEQUENCE CHARACTERISTICS:
        (A) LENGTH: 976 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Met Phe Thr Leu Ser Pro Ala Pro Arg Glu Val Ile Arg Thr Leu Pro
1               5                   10                  15

Ser Leu Glu Ser Leu Gln Arg Leu Phe Asp Gln Gln Leu Ser Pro Gly
                20                  25                  30

Leu Arg Pro Arg Pro Gln Val Pro Gly Glu Ala Asn Pro Ile Asn Met
            35                  40                  45

Val Ser Lys Leu Ser Gln Leu Thr Ser Leu Leu Ser Ser Ile Glu Asp
50                  55                  60

Lys Val Lys Ala Leu Leu His Glu Gly Pro Glu Ser Pro His Arg Pro
65                  70                  75                  80

Ser Leu Ile Pro Pro Val Thr Phe Glu Val Lys Ala Glu Ser Leu Gly
                85                  90                  95

Ile Pro Gln Lys Met Gln Leu Lys Val Asp Val Glu Ser Gly Lys Leu
            100                 105                 110

Ile Ile Lys Lys Ser Lys Asp Gly Ser Glu Asp Lys Phe Tyr Ser His
            115                 120                 125

Lys Lys Ile Leu Gln Leu Ile Lys Ser Gln Lys Phe Leu Asn Lys Leu
            130                 135                 140

Val Ile Leu Val Glu Thr Glu Lys Glu Lys Ile Leu Arg Lys Glu Tyr
145                 150                 155                 160

Val Phe Ala Asp Ser Lys Lys Arg Glu Gly Phe Cys Gln Leu Leu Gln
                165                 170                 175

Gln Met Lys Asn Lys His Ser Glu Gln Pro Glu Pro Asp Met Ile Thr
            180                 185                 190

Ile Phe Ile Gly Thr Trp Asn Met Gly Asn Ala Pro Pro Pro Lys Lys
            195                 200                 205

Ile Thr Ser Trp Phe Leu Ser Lys Gly Gln Gly Lys Thr Arg Asp Asp
            210                 215                 220

Ser Ala Asp Tyr Ile Pro His Asp Ile Tyr Val Ile Gly Thr Gln Glu
225                 230                 235                 240

Asp Pro Leu Ser Glu Lys Glu Trp Leu Glu Ile Leu Lys His Ser Leu
                245                 250                 255

Gln Glu Ile Thr Ser Val Thr Phe Lys Thr Val Ala Ile His Thr Leu
            260                 265                 270

Trp Asn Ile Arg Ile Val Val Leu Ala Lys Pro Glu His Glu Asn Arg
            275                 280                 285

Ile Ser His Ile Cys Thr Asp Asn Val Lys Thr Gly Ile Ala Asn Thr
            290                 295                 300

Leu Gly Asn Lys Gly Ala Val Gly Val Ser Phe Met Phe Asn Gly Thr

```
305                 310                 315                 320
Ser Leu Gly Phe Val Asn Ser His Leu Thr Ser Gly Ser Glu Lys Lys
                325                 330                 335
Leu Arg Arg Asn Gln Asn Tyr Met Asn Ile Leu Arg Phe Leu Ala Leu
                340                 345                 350
Gly Asp Lys Lys Leu Ser Pro Phe Asn Ile Thr His Arg Phe Thr His
                355                 360                 365
Leu Phe Trp Phe Gly Asp Leu Asn Tyr Arg Val Asp Leu Pro Thr Trp
370                 375                 380
Glu Ala Glu Thr Ile Ile Gln Lys Ile Lys Gln Gln Tyr Ala Asp
385                 390                 395                 400
Leu Leu Ser His Asp Gln Leu Leu Thr Glu Arg Arg Glu Gln Lys Val
                405                 410                 415
Phe Leu His Phe Glu Glu Glu Ile Thr Phe Ala Pro Thr Tyr Arg
                420                 425                 430
Phe Glu Arg Leu Thr Arg Asp Lys Tyr Ala Tyr Thr Lys Gln Lys Ala
                435                 440                 445
Thr Gly Met Lys Tyr Asn Leu Pro Ser Trp Cys Asp Arg Val Leu Trp
450                 455                 460
Lys Ser Tyr Pro Leu Val His Val Val Cys Gln Ser Tyr Gly Ser Thr
465                 470                 475                 480
Ser Asp Ile Met Thr Ser Asp His Ser Pro Val Phe Ala Thr Phe Glu
                485                 490                 495
Ala Gly Val Thr Ser Gln Phe Val Ser Lys Asn Gly Pro Gly Thr Val
                500                 505                 510
Asp Ser Gln Gly Gln Ile Glu Phe Leu Arg Cys Tyr Ala Thr Leu Lys
                515                 520                 525
Thr Lys Ser Gln Thr Lys Phe Tyr Leu Glu Phe His Ser Ser Cys Leu
                530                 535                 540
Glu Ser Phe Val Lys Ser Gln Glu Gly Glu Asn Glu Glu Gly Ser Glu
545                 550                 555                 560
Gly Glu Leu Val Val Lys Phe Gly Glu Thr Leu Pro Lys Leu Lys Pro
                565                 570                 575
Ile Ile Ser Asp Pro Glu Tyr Leu Leu Asp Gln His Ile Leu Ile Ser
                580                 585                 590
Ile Lys Ser Ser Asp Ser Asp Glu Ser Tyr Gly Glu Gly Cys Ile Ala
                595                 600                 605
Leu Arg Leu Glu Ala Thr Glu Thr Gln Leu Pro Ile Tyr Thr Pro Leu
                610                 615                 620
Thr His His Gly Glu Leu Thr Gly His Phe Gln Gly Glu Ile Lys Leu
625                 630                 635                 640
Gln Thr Ser Gln Gly Lys Thr Arg Glu Lys Leu Tyr Asp Phe Val Lys
                645                 650                 655
Thr Glu Arg Asp Glu Ser Ser Gly Pro Lys Thr Leu Lys Ser Leu Thr
                660                 665                 670
Ser His Asp Pro Met Lys Gln Trp Glu Val Thr Ser Arg Ala Pro Pro
                675                 680                 685
Cys Ser Gly Ser Ser Ile Thr Glu Ile Ile Asn Pro Asn Tyr Met Gly
                690                 695                 700
Val Gly Pro Phe Gly Pro Pro Met Pro Leu His Val Lys Gln Thr Leu
705                 710                 715                 720
Ser Pro Asp Gln Gln Pro Thr Ala Trp Ser Tyr Asp Gln Pro Pro Lys
                725                 730                 735
```

-continued

```
Asp Ser Pro Leu Gly Pro Cys Arg Gly Glu Ser Pro Thr Pro Pro
            740                 745                 750
Gly Gln Pro Pro Ile Ser Pro Lys Lys Phe Leu Pro Ser Thr Ala Asn
        755                 760                 765
Arg Gly Leu Pro Pro Arg Thr Gln Glu Ser Arg Pro Ser Asp Leu Gly
    770                 775                 780
Lys Asn Ala Gly Asp Thr Leu Pro Gln Glu Asp Leu Pro Leu Thr Lys
785                 790                 795                 800
Pro Glu Met Phe Glu Asn Pro Leu Tyr Gly Ser Leu Ser Ser Phe Pro
                805                 810                 815
Lys Pro Ala Pro Arg Lys Asp Gln Glu Ser Pro Lys Met Pro Arg Lys
            820                 825                 830
Glu Pro Pro Pro Cys Pro Glu Pro Gly Ile Leu Ser Pro Ser Ile Val
        835                 840                 845
Leu Thr Lys Ala Gln Glu Ala Asp Arg Gly Glu Gly Pro Gly Lys Gln
    850                 855                 860
Val Pro Ala Pro Arg Leu Arg Ser Phe Thr Cys Ser Ser Ser Ala Glu
865                 870                 875                 880
Gly Arg Ala Ala Gly Gly Asp Lys Ser Gln Gly Lys Pro Lys Thr Pro
                885                 890                 895
Val Ser Ser Gln Ala Pro Val Pro Ala Lys Arg Pro Ile Lys Pro Ser
            900                 905                 910
Arg Ser Glu Ile Asn Gln Gln Thr Pro Thr Pro Thr Pro Arg Pro
        915                 920                 925
Pro Leu Pro Val Lys Ser Pro Ala Val Leu His Leu Gln His Ser Lys
    930                 935                 940
Gly Arg Asp Tyr Arg Asp Asn Thr Glu Leu Pro His His Gly Lys His
945                 950                 955                 960
Arg Pro Glu Glu Gly Pro Pro Gly Pro Leu Gly Arg Thr Ala Met Gln
                965                 970                 975
```

(2) INFORMATION FOR SEQ ID NO:15:

(i) SEQUENCE CHARACTERISTICS:
        (A) LENGTH: 1189 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Met Val Pro Cys Trp Asn His Gly Asn Ile Thr Arg Ser Lys Ala Glu
1               5                   10                  15
Glu Leu Leu Ser Arg Thr Gly Lys Asp Gly Ser Phe Leu Val Arg Ala
            20                  25                  30
Ser Glu Ser Ile Ser Arg Ala Tyr Ala Leu Cys Val Leu Tyr Arg Asn
        35                  40                  45
Cys Val Tyr Thr Tyr Arg Ile Leu Pro Asn Glu Asp Asp Lys Phe Thr
    50                  55                  60
Val Gln Ala Ser Glu Gly Val Ser Met Arg Phe Phe Thr Lys Leu Asp
65                  70                  75                  80
Gln Leu Ile Glu Phe Tyr Lys Lys Glu Asn Met Gly Leu Val Thr His
                85                  90                  95
Leu Gln Tyr Pro Val Pro Leu Glu Glu Glu Asp Thr Gly Asp Asp Pro
            100                 105                 110
```

-continued

```
Glu Glu Asp Thr Val Glu Ser Val Val Ser Pro Pro Glu Leu Pro Pro
            115                 120                 125

Arg Asn Ile Pro Leu Thr Ala Ser Ser Cys Glu Ala Lys Glu Val Pro
        130                 135                 140

Phe Ser Asn Glu Asn Pro Arg Ala Thr Glu Thr Ser Arg Pro Ser Leu
145                 150                 155                 160

Ser Glu Thr Leu Phe Gln Arg Leu Gln Ser Met Asp Thr Ser Gly Leu
                165                 170                 175

Pro Glu Glu His Leu Lys Ala Ile Gln Asp Tyr Leu Ser Thr Gln Leu
            180                 185                 190

Ala Gln Asp Ser Glu Phe Val Lys Thr Gly Ser Ser Ser Leu Pro His
        195                 200                 205

Leu Lys Lys Leu Thr Thr Leu Leu Cys Lys Glu Leu Tyr Gly Glu Val
    210                 215                 220

Ile Arg Thr Leu Pro Ser Leu Glu Ser Leu Gln Arg Leu Phe Asp Gln
225                 230                 235                 240

Gln Leu Ser Pro Gly Leu Arg Pro Arg Pro Gln Val Pro Gly Glu Ala
                245                 250                 255

Asn Pro Ile Asn Met Val Ser Lys Leu Ser Gln Leu Thr Ser Leu Leu
            260                 265                 270

Ser Ser Ile Glu Asp Lys Val Lys Ala Leu Leu His Glu Gly Pro Glu
        275                 280                 285

Ser Pro His Arg Pro Ser Leu Ile Pro Pro Val Thr Phe Glu Val Lys
    290                 295                 300

Ala Glu Ser Leu Gly Ile Pro Gln Lys Met Gln Leu Lys Val Asp Val
305                 310                 315                 320

Glu Ser Gly Lys Leu Ile Ile Lys Lys Ser Lys Asp Gly Ser Glu Asp
                325                 330                 335

Lys Phe Tyr Ser His Lys Lys Ile Leu Gln Leu Ile Lys Ser Gln Lys
            340                 345                 350

Phe Leu Asn Lys Leu Val Ile Leu Val Glu Thr Glu Lys Glu Lys Ile
        355                 360                 365

Leu Arg Lys Glu Tyr Val Phe Ala Asp Ser Lys Lys Arg Glu Gly Phe
    370                 375                 380

Cys Gln Leu Leu Gln Gln Met Lys Asn Lys His Ser Glu Gln Pro Glu
385                 390                 395                 400

Pro Asp Met Ile Thr Ile Phe Ile Gly Thr Trp Asn Met Gly Asn Ala
                405                 410                 415

Pro Pro Pro Lys Lys Ile Thr Ser Trp Phe Leu Ser Lys Gly Gln Gly
            420                 425                 430

Lys Thr Arg Asp Asp Ser Ala Asp Tyr Ile Pro His Asp Ile Tyr Val
        435                 440                 445

Ile Gly Thr Gln Glu Asp Pro Leu Ser Glu Lys Glu Trp Leu Glu Ile
    450                 455                 460

Leu Lys His Ser Leu Gln Glu Ile Thr Ser Val Thr Phe Lys Thr Val
465                 470                 475                 480

Ala Ile His Thr Leu Trp Asn Ile Arg Ile Val Val Leu Ala Lys Pro
                485                 490                 495

Glu His Glu Asn Arg Ile Ser His Ile Cys Thr Asp Asn Val Lys Thr
            500                 505                 510

Gly Ile Ala Asn Thr Leu Gly Asn Lys Gly Ala Val Gly Val Ser Phe
        515                 520                 525
```

-continued

```
Met Phe Asn Gly Thr Ser Leu Gly Phe Val Asn Ser His Leu Thr Ser
        530                 535                 540

Gly Ser Glu Lys Lys Leu Arg Arg Asn Gln Asn Tyr Met Asn Ile Leu
545                 550                 555                 560

Arg Phe Leu Ala Leu Gly Asp Lys Lys Leu Ser Pro Phe Asn Ile Thr
                565                 570                 575

His Arg Phe Thr His Leu Phe Trp Phe Gly Asp Leu Asn Tyr Arg Val
            580                 585                 590

Asp Leu Pro Thr Trp Glu Ala Glu Thr Ile Ile Gln Lys Ile Lys Gln
        595                 600                 605

Gln Gln Tyr Ala Asp Leu Leu Ser His Asp Gln Leu Leu Thr Glu Arg
    610                 615                 620

Arg Glu Gln Lys Val Phe Leu His Phe Glu Glu Glu Ile Thr Phe
625                 630                 635                 640

Ala Pro Thr Tyr Arg Phe Glu Arg Leu Thr Arg Asp Lys Tyr Ala Tyr
                645                 650                 655

Thr Lys Gln Lys Ala Thr Gly Met Lys Tyr Asn Leu Pro Ser Trp Cys
            660                 665                 670

Asp Arg Val Leu Trp Lys Ser Tyr Pro Leu Val His Val Val Cys Gln
        675                 680                 685

Ser Tyr Gly Ser Thr Ser Asp Ile Met Thr Ser Asp His Ser Pro Val
    690                 695                 700

Phe Ala Thr Phe Glu Ala Gly Val Thr Ser Gln Phe Val Ser Lys Asn
705                 710                 715                 720

Gly Pro Gly Thr Val Asp Ser Gln Gly Gln Ile Glu Phe Leu Arg Cys
                725                 730                 735

Tyr Ala Thr Leu Lys Thr Lys Ser Gln Thr Lys Phe Tyr Leu Glu Phe
            740                 745                 750

His Ser Ser Cys Leu Glu Ser Phe Val Lys Ser Gln Glu Gly Glu Asn
        755                 760                 765

Glu Glu Gly Ser Glu Gly Glu Leu Val Val Lys Phe Gly Glu Thr Leu
    770                 775                 780

Pro Lys Leu Lys Pro Ile Ile Ser Asp Pro Glu Tyr Leu Leu Asp Gln
785                 790                 795                 800

His Ile Leu Ile Ser Ile Lys Ser Ser Asp Ser Asp Glu Ser Tyr Gly
                805                 810                 815

Glu Gly Cys Ile Ala Leu Arg Leu Glu Ala Thr Glu Thr Gln Leu Pro
            820                 825                 830

Ile Tyr Thr Pro Leu Thr His His Gly Glu Leu Thr Gly His Phe Gln
        835                 840                 845

Gly Glu Ile Lys Leu Gln Thr Ser Gln Gly Lys Thr Arg Glu Lys Leu
    850                 855                 860

Tyr Asp Phe Val Lys Thr Glu Arg Asp Glu Ser Ser Gly Pro Lys Thr
865                 870                 875                 880

Leu Lys Ser Leu Thr Ser His Asp Pro Met Lys Gln Trp Glu Val Thr
                885                 890                 895

Ser Arg Ala Pro Pro Cys Ser Gly Ser Ser Ile Thr Glu Ile Ile Asn
            900                 905                 910

Pro Asn Tyr Met Gly Val Gly Pro Phe Gly Pro Pro Met Pro Leu His
        915                 920                 925

Val Lys Gln Thr Leu Ser Pro Asp Gln Gln Pro Thr Ala Trp Ser Tyr
    930                 935                 940

Asp Gln Pro Pro Lys Asp Ser Pro Leu Gly Pro Cys Arg Gly Glu Ser
```

```
                      945                 950                 955                 960
Pro Pro Thr Pro Pro Gly Gln Pro Pro Ile Ser Pro Lys Lys Phe Leu
                965                 970                 975

Pro Ser Thr Ala Asn Arg Gly Leu Pro Pro Arg Thr Gln Glu Ser Arg
                980                 985                 990

Pro Ser Asp Leu Gly Lys Asn Ala Gly Asp Thr Leu Pro Gln Glu Asp
                995                1000                1005

Leu Pro Leu Thr Lys Pro Glu Met Phe Glu Asn Pro Leu Tyr Gly Ser
    1010                1015                1020

Leu Ser Ser Phe Pro Lys Pro Ala Pro Arg Lys Asp Gln Glu Ser Pro
1025                1030                1035                1040

Lys Met Pro Arg Lys Glu Pro Pro Cys Pro Glu Pro Gly Ile Leu
                1045                1050                1055

Ser Pro Ser Ile Val Leu Thr Lys Ala Gln Glu Ala Asp Arg Gly Glu
                1060                1065                1070

Gly Pro Gly Lys Gln Val Pro Ala Pro Arg Leu Arg Ser Phe Thr Cys
                1075                1080                1085

Ser Ser Ser Ala Glu Gly Arg Ala Ala Gly Gly Asp Lys Ser Gln Gly
    1090                1095                1100

Lys Pro Lys Thr Pro Val Ser Ser Gln Ala Pro Val Pro Ala Lys Arg
1105                1110                1115                1120

Pro Ile Lys Pro Ser Arg Ser Glu Ile Asn Gln Gln Thr Pro Pro Thr
                1125                1130                1135

Pro Thr Pro Arg Pro Pro Leu Pro Val Lys Ser Pro Ala Val Leu His
                1140                1145                1150

Leu Gln His Ser Lys Gly Arg Asp Tyr Arg Asp Asn Thr Glu Leu Pro
                1155                1160                1165

His His Gly Lys His Arg Pro Glu Glu Gly Pro Pro Gly Pro Leu Gly
                1170                1175                1180

Arg Thr Ala Met Gln
1185

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Pro Lys Thr Pro
1

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Pro Ile Lys Pro
1
```

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Pro Pro Thr Pro
1
```

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Pro Arg Pro Pro Leu Pro
1               5
```

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Pro Pro Gly Pro
1
```

(2) INFORMATION FOR SEQ ID NO:21:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GGGAAGCCCA AGACCCCGGT CAGCTCCCAG GCCCCGGTGC CGGCCAAGAG GCCCATCAAG     60

CCTTCCAGAT CGGAAATCAA CCAGCAGACC CCGCCCACCC CGACGCCGCG GCCGCCGCTG    120

CCAGTCAAGA GCCCGGCGGT GCTGCACCTC CAGCACTCCA AGGGCCGCGA CTACCGCGAC    180

AACACCGAGC TCCCGCATCA CGGCAAGCAC CGGCCGGAGG AGGGGCCACC AGGGCCTCTA    240

GGCAGGACTG CCATGCAGTG A                                              261
```

(2) INFORMATION FOR SEQ ID NO:22:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Gly Lys Pro Lys Thr Pro Val Ser Ser Gln Ala Pro Val Pro Ala Lys
1               5                   10                  15

Arg Pro Ile Lys Pro Ser Arg Ser Glu Ile Asn Gln Gln Thr Pro Pro
            20                  25                  30

Thr Pro Thr Pro Arg Pro Pro Leu Pro Val Lys Ser Pro Ala Val Leu
        35                  40                  45

His Leu Gln His Ser Lys Gly Arg Asp Tyr Arg Asp Asn Thr Glu Leu
    50                  55                  60

Leu Pro His His Gly Lys His Arg Pro Glu Glu Gly Pro Pro Gly Pro
65                  70                  75                  80

Leu Gly Arg Thr Ala Met Gln
                85
```

(2) INFORMATION FOR SEQ ID NO:23:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Trp Asn His Gly Asn Ile Thr Arg Ser Lys Ala Glu Glu Leu Leu Ser
1               5                   10                  15

Arg Thr Gly Lys Asp Gly Ser Phe Leu Val Arg Ala Ser Glu Ser Ile
            20                  25                  30

Ser Arg Ala Tyr Ala Leu Cys Val Leu Tyr Arg Asn Cys Val Tyr Thr
        35                  40                  45

Tyr Arg Ile Leu Pro Asn Glu Asp Asp Lys Phe Thr Val Gln Ala Ser
    50                  55                  60

Glu Gly Val Ser Met Arg Phe Phe Thr Lys Leu Asp Gln Leu Ile Glu
65                  70                  75                  80

Phe Tyr Lys Lys Glu Asn Met Gly Leu Val Thr His Leu Gln Tyr Pro
                85                  90                  95

Val Pro Leu
```

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Phe Trp Phe Gly Asp Leu Asn Tyr Arg
1               5
```

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:25:

Leu Val Ile Leu Val Glu Thr Glu Lys
1               5

(2) INFORMATION FOR SEQ ID NO:26:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:26:

Leu Ser Pro Phe Asn Ile Thr His Arg Phe
1               5                   10

(2) INFORMATION FOR SEQ ID NO:27:

(i) SEQUENCE CHARACTERISTICS:
          (A) LENGTH: 14 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:27:

Leu Ser Gln Leu Thr Ser Leu Leu Ser Ser Ile Glu Asp Lys
1               5                   10

(2) INFORMATION FOR SEQ ID NO:28:

(i) SEQUENCE CHARACTERISTICS:
          (A) LENGTH: 1229 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:28:

Gln Pro Arg Pro Pro Arg Gly Asn Gly Arg Gln Val Ala Val Glu Gly
1               5                   10                  15

Pro Pro Leu Pro Ser Val Val Cys Gly Ser Trp Gly Cys Leu Pro Ala
                20                  25                  30

Arg Pro Arg Arg Pro Thr Pro Thr Met Val Pro Cys Trp Asn His Gly
            35                  40                  45

Asn Ile Thr Arg Ser Lys Ala Glu Glu Leu Leu Ser Arg Thr Gly Lys
    50                  55                  60

Asp Gly Ser Phe Leu Val Arg Ala Ser Glu Ser Ile Ser Arg Ala Tyr
65                  70                  75                  80

Ala Leu Cys Val Leu Tyr Arg Asn Cys Val Tyr Thr Tyr Arg Ile Leu
                85                  90                  95

Pro Asn Glu Asp Asp Lys Phe Thr Val Gln Ala Ser Glu Gly Val Ser
                100                 105                 110

Met Arg Phe Phe Thr Lys Leu Asp Gln Leu Ile Glu Phe Tyr Lys Lys
            115                 120                 125

Glu Asn Met Gly Leu Val Thr His Leu Gln Tyr Pro Val Pro Leu Glu

-continued

```
            130                 135                 140
Glu Glu Asp Thr Gly Asp Asp Pro Glu Glu Asp Thr Val Glu Ser Val
145                 150                 155                 160
Val Ser Pro Pro Glu Leu Pro Pro Arg Asn Ile Pro Leu Thr Ala Ser
                    165                 170                 175
Ser Cys Glu Ala Lys Glu Val Pro Phe Ser Asn Glu Asn Pro Arg Ala
                180                 185                 190
Thr Glu Thr Ser Arg Pro Ser Leu Ser Glu Thr Leu Phe Gln Arg Leu
            195                 200                 205
Gln Ser Met Asp Thr Ser Gly Leu Pro Glu Glu His Leu Lys Ala Ile
        210                 215                 220
Gln Asp Tyr Leu Ser Thr Gln Leu Ala Gln Asp Ser Glu Phe Val Lys
225                 230                 235                 240
Thr Gly Ser Ser Leu Pro His Leu Lys Lys Leu Thr Thr Leu Leu
                    245                 250                 255
Cys Lys Glu Leu Tyr Gly Glu Val Ile Arg Thr Leu Pro Ser Leu Glu
                260                 265                 270
Ser Leu Gln Arg Leu Phe Asp Gln Gln Leu Ser Pro Gly Leu Arg Pro
            275                 280                 285
Arg Pro Gln Val Pro Gly Glu Ala Asn Pro Ile Asn Met Val Ser Lys
        290                 295                 300
Leu Ser Gln Leu Thr Ser Leu Leu Ser Ser Ile Glu Asp Lys Val Lys
305                 310                 315                 320
Ala Leu Leu His Glu Gly Pro Glu Ser Pro His Arg Pro Ser Leu Ile
                    325                 330                 335
Pro Pro Val Thr Phe Glu Val Lys Ala Glu Ser Leu Gly Ile Pro Gln
                340                 345                 350
Lys Met Gln Leu Lys Val Asp Val Glu Ser Gly Lys Leu Ile Ile Lys
            355                 360                 365
Lys Ser Lys Asp Gly Ser Glu Asp Lys Phe Tyr Ser His Lys Lys Ile
        370                 375                 380
Leu Gln Leu Ile Lys Ser Gln Lys Phe Leu Asn Lys Leu Val Ile Leu
385                 390                 395                 400
Val Glu Thr Glu Lys Glu Lys Ile Leu Arg Lys Glu Tyr Val Phe Ala
                    405                 410                 415
Asp Ser Lys Lys Arg Glu Gly Phe Cys Gln Leu Leu Gln Gln Met Lys
                420                 425                 430
Asn Lys His Ser Glu Gln Pro Glu Pro Asp Met Ile Thr Ile Phe Ile
            435                 440                 445
Gly Thr Trp Asn Met Gly Asn Ala Pro Pro Lys Lys Ile Thr Ser
        450                 455                 460
Trp Phe Leu Ser Lys Gly Gln Gly Lys Thr Arg Asp Asp Ser Ala Asp
465                 470                 475                 480
Tyr Ile Pro His Asp Ile Tyr Val Ile Gly Thr Gln Glu Asp Pro Leu
                    485                 490                 495
Ser Glu Lys Glu Trp Leu Glu Ile Leu Lys His Ser Leu Gln Glu Ile
                500                 505                 510
Thr Ser Val Thr Phe Lys Thr Val Ala Ile His Thr Leu Trp Asn Ile
            515                 520                 525
Arg Ile Val Val Leu Ala Lys Pro Glu His Glu Asn Arg Ile Ser His
        530                 535                 540
Ile Cys Thr Asp Asn Val Lys Thr Gly Ile Ala Asn Thr Leu Gly Asn
545                 550                 555                 560
```

-continued

```
Lys Gly Ala Val Gly Val Ser Phe Met Phe Asn Gly Thr Ser Leu Gly
            565                 570                 575
Phe Val Asn Ser His Leu Thr Ser Gly Ser Glu Lys Lys Leu Arg Arg
            580                 585                 590
Asn Gln Asn Tyr Met Asn Ile Leu Arg Phe Leu Ala Leu Gly Asp Lys
            595                 600                 605
Lys Leu Ser Pro Phe Asn Ile Thr His Arg Phe Thr His Leu Phe Trp
            610                 615                 620
Phe Gly Asp Leu Asn Tyr Arg Val Asp Leu Pro Thr Trp Glu Ala Glu
625                 630                 635                 640
Thr Ile Ile Gln Lys Ile Lys Gln Gln Tyr Ala Asp Leu Leu Ser
            645                 650                 655
His Asp Gln Leu Leu Thr Glu Arg Arg Glu Gln Lys Val Phe Leu His
            660                 665                 670
Phe Glu Glu Glu Ile Thr Phe Ala Pro Thr Tyr Arg Phe Glu Arg
            675                 680                 685
Leu Thr Arg Asp Lys Tyr Ala Tyr Thr Lys Gln Lys Ala Thr Gly Met
            690                 695                 700
Lys Tyr Asn Leu Pro Ser Trp Cys Asp Arg Val Leu Trp Lys Ser Tyr
705                 710                 715                 720
Pro Leu Val His Val Val Cys Gln Ser Tyr Gly Ser Thr Ser Asp Ile
            725                 730                 735
Met Thr Ser Asp His Ser Pro Val Phe Ala Thr Phe Glu Ala Gly Val
            740                 745                 750
Thr Ser Gln Phe Val Ser Lys Asn Gly Pro Gly Thr Val Asp Ser Gln
            755                 760                 765
Gly Gln Ile Glu Phe Leu Arg Cys Tyr Ala Thr Leu Lys Thr Lys Ser
            770                 775                 780
Gln Thr Lys Phe Tyr Leu Glu Phe His Ser Ser Cys Leu Glu Ser Phe
785                 790                 795                 800
Val Lys Ser Gln Glu Gly Glu Asn Glu Glu Gly Ser Glu Gly Glu Leu
            805                 810                 815
Val Val Lys Phe Gly Glu Thr Leu Pro Lys Leu Lys Pro Ile Ile Ser
            820                 825                 830
Asp Pro Glu Tyr Leu Leu Asp Gln His Ile Leu Ile Ser Ile Lys Ser
            835                 840                 845
Ser Asp Ser Asp Glu Ser Tyr Gly Glu Gly Cys Ile Ala Leu Arg Leu
850                 855                 860
Glu Ala Thr Glu Thr Gln Leu Pro Ile Tyr Thr Pro Leu Thr His His
865                 870                 875                 880
Gly Glu Leu Thr Gly His Phe Gln Gly Glu Ile Lys Leu Gln Thr Ser
            885                 890                 895
Gln Gly Lys Thr Arg Glu Lys Leu Tyr Asp Phe Val Lys Thr Glu Arg
            900                 905                 910
Asp Glu Ser Ser Gly Pro Lys Thr Leu Lys Ser Leu Thr Ser His Asp
            915                 920                 925
Pro Met Lys Gln Trp Glu Val Thr Ser Arg Ala Pro Pro Cys Ser Gly
            930                 935                 940
Ser Ser Ile Thr Glu Ile Ile Asn Pro Asn Tyr Met Gly Val Gly Pro
945                 950                 955                 960
Phe Gly Pro Pro Met Pro Leu His Val Lys Gln Thr Leu Ser Pro Asp
            965                 970                 975
```

```
Gln Gln Pro Thr Ala Trp Ser Tyr Asp Gln Pro Pro Lys Asp Ser Pro
            980                 985                 990
Leu Gly Pro Cys Arg Gly Glu Ser Pro Pro Thr Pro Pro Gly Gln Pro
        995                1000                1005
Pro Ile Ser Pro Lys Lys Phe Leu Pro Ser Thr Ala Asn Arg Gly Leu
    1010                1015                1020
Pro Pro Arg Thr Gln Glu Ser Arg Pro Ser Asp Leu Gly Lys Asn Ala
1025                1030                1035                1040
Gly Asp Thr Leu Pro Gln Glu Asp Leu Pro Leu Thr Lys Pro Glu Met
                1045                1050                1055
Phe Glu Asn Pro Leu Tyr Gly Ser Leu Ser Ser Phe Pro Lys Pro Ala
            1060                1065                1070
Pro Arg Lys Asp Gln Glu Ser Pro Lys Met Pro Arg Lys Glu Pro Pro
        1075                1080                1085
Pro Cys Pro Glu Pro Gly Ile Leu Ser Pro Ser Ile Val Leu Thr Lys
    1090                1095                1100
Ala Gln Glu Ala Asp Arg Gly Glu Gly Pro Gly Lys Gln Val Pro Ala
1105                1110                1115                1120
Pro Arg Leu Arg Ser Phe Thr Cys Ser Ser Ser Ala Glu Gly Arg Ala
                1125                1130                1135
Ala Gly Gly Asp Lys Ser Gln Gly Lys Pro Lys Thr Pro Val Ser Ser
            1140                1145                1150
Gln Ala Pro Val Pro Ala Lys Arg Pro Ile Lys Pro Ser Arg Ser Glu
        1155                1160                1165
Ile Asn Gln Gln Thr Pro Pro Thr Pro Thr Arg Pro Pro Leu Pro
    1170                1175                1180
Val Lys Ser Pro Ala Val Leu His Leu Gln His Ser Lys Gly Arg Asp
1185                1190                1195                1200
Tyr Arg Asp Asn Thr Glu Leu Pro His His Gly Lys His Arg Pro Glu
                1205                1210                1215
Glu Gly Pro Pro Gly Pro Leu Gly Arg Thr Ala Met Gln
            1220                1225
```

(2) INFORMATION FOR SEQ ID NO:29:

(i) SEQUENCE CHARACTERISTICS:
        (A) LENGTH: 934 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
GCAGCCGAGG CCACCAAGAG GCAACGGGCG GCAGGTTGCA GTGGAGGGGC CTCCGCTCCC     60
CTCGGTGGTG TGTGGGTCCT GGGGGTGCCT GCCGGCCCGG CCGAGGAGGC CCACGCCCAC    120
CATGGTCCCC TGCTGGAACC ATGGCAACAT CACCCGCTCC AAGGCGGAGG AGCTGCTTTC    180
CAGGACAGGC AAGGACGGGA GCTTCCTCGT GCGTGCCAGC GAGTCCATCT CCCGGGCATA    240
CGCGCTCTGC GTGCTGTATC GGAATTGCGT TTACACTTAC AGAATTCTGC CAATGAAGA    300
TGATAAATTC ACTGTTCAGG CATCCGAAGG CGTCTCCATG AGGTTCTTCA CCAAGCTGGA    360
CCAGCTCATC GAGTTTTACA AGAAGGAAAA CATGGGGCTG GTGACCCATC TGCAATACCC    420
TGTGCCGCTG AGGAAGAGG ACACAGGCGA CGACCCTGAG GAGGACACAG AAAGTGTCGT    480
GTCTCCACCC GAGCTGCCCC AAGAAACAT CCCGCTGACT GCCAGCTCCT GTGAGGCCAA    540
```

```
GGAGGTTCCT TTTTCAAACG AGAATCCCCG AGCGACCGAG ACCAGCCGGC CGAGCCTCTC      600

CGAGACATTG TTCCAGCGAC TGCAAAGCAT GGACACCAGT GGAAATCCTA ATGACAGGGC      660

TGAAGCCGCA TTTCCAACTT GAAGGATCCA TCTGAGGCTG CCAGGGCTGC CCTCCTCCTA      720

CTCTCTCACT TGGCAAAATA TGAAGTAGAT GCCGATGGGA CACATACGCC ACCGGGTTGC      780

TATGATACTT GGCGTGTTCC TATTTCCACC TGGACATACC CATTGGTTTT TTCCCTGGGC      840

TTTCCAGCCT GAATTTTGTG CACGCTCCTT GATTTATTTG TGGTATTTAT CAAATAGCCG      900

AATATCCAGT GTTGGTACTA AAAAAAAAAA AAAA                                 934
```

(2) INFORMATION FOR SEQ ID NO:30:

(i) SEQUENCE CHARACTERISTICS:
        (A) LENGTH: 226 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Gln Pro Arg Pro Pro Arg Gly Asn Gly Arg Gln Val Ala Val Glu Gly
1               5                   10                  15

Pro Pro Leu Pro Ser Val Val Cys Gly Ser Trp Gly Cys Leu Pro Ala
            20                  25                  30

Arg Pro Arg Pro Thr Pro Thr Met Val Pro Cys Trp Asn His Gly
        35                  40                  45

Asn Ile Thr Arg Ser Lys Ala Glu Glu Leu Leu Ser Arg Thr Gly Lys
    50                  55                  60

Asp Gly Ser Phe Leu Val Arg Ala Ser Glu Ser Ile Ser Arg Ala Tyr
65                  70                  75                  80

Ala Leu Cys Val Leu Tyr Arg Asn Cys Val Tyr Thr Tyr Arg Ile Leu
                85                  90                  95

Pro Asn Glu Asp Asp Lys Phe Thr Val Gln Ala Ser Glu Gly Val Ser
            100                 105                 110

Met Arg Phe Phe Thr Lys Leu Asp Gln Leu Ile Glu Phe Tyr Lys Lys
        115                 120                 125

Glu Asn Met Gly Leu Val Thr His Leu Gln Tyr Pro Val Pro Leu Glu
    130                 135                 140

Glu Glu Asp Thr Gly Asp Asp Pro Glu Glu Asp Thr Glu Ser Val Val
145                 150                 155                 160

Ser Pro Pro Glu Leu Pro Pro Arg Asn Ile Pro Leu Thr Ala Ser Ser
                165                 170                 175

Cys Glu Ala Lys Glu Val Pro Phe Ser Asn Glu Asn Pro Arg Ala Thr
            180                 185                 190

Glu Thr Ser Arg Pro Ser Leu Ser Glu Thr Leu Phe Gln Arg Leu Gln
        195                 200                 205

Ser Met Asp Thr Ser Gly Asn Pro Asn Asp Arg Ala Glu Ala Ala Phe
    210                 215                 220

Pro Thr
225
```

(2) INFORMATION FOR SEQ ID NO:31:

(i) SEQUENCE CHARACTERISTICS:
        (A) LENGTH: 4 amino acids
        (B) TYPE: amino acid
        (C) STRANDEDNESS: single

```
            (D) TOPOLOGY: linear (ii) MOLECULE TYPE: peptide (xi) SEQUENCE DESCRIPTION: SEQ ID NO:31:

Asn Pro Asn Tyr
1

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Asn Pro Leu Tyr
1

(2) INFORMATION FOR SEQ ID NO:33:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Leu Pro Ser Trp Cys Asp Arg Val Leu
1               5
```

SIGNALING INOSITOL POLYPHOSPHATE 5-PHOSPHATASES (SIPS)

CROSS-REFERENCE TO RELATED PATENT APPLICATION

This application is a divisional of U.S. patent application Ser. No. 08/759,397, filed Dec. 4, 1996, which is a continuation-in-part of application Ser. Nos. 08/569,578, filed Dec. 8, 1995, now abandoned and a CIP of Ser. No. 08/624,190, filed Mar. 28, 1996, now abandoned. This application also claims the benefit of Provisional No. 60/008,606 filed Dec. 14, 1995.

GENERAL DESCRIPTION

1. Field of the Invention

This invention relates to novel 5-phosphatase polypeptides called signaling inositol polyphosphate 5-phosphatases (SIPs) or fragments or derivatives thereof that participate in signal transduction. This invention further relates to polynucleotides that encode novel polypeptides or fragments or derivatives thereof and to vectors and host cells containing such. This invention describes modulators of SIP activity, and relates to methods of treating diseases characterized by abnormal cell growth associated with abnormal production of inositol polyphosphate and phosphatidylinositol phosphates or aberrant 5-phosphatase activity.

2. Background of the Invention

SHC and GRB2 protein signaling molecules form a complex in response to growth factor or oncogenic transformation, as described in Rozakis-Adcock et al *Nature* 360: 689–92 (1992). These proteins are thought to transmit mitogenic signals from receptor and non-receptor tyrosine kinases to ras, a member of a major class of oncogenes and proto-oncogenes that encode G proteins that are located on the inner face of the plasma membrane, where they bind and hydrolyze GTP. Ras proteins are involved in an unknown way in growth-factor stimulation of cell proliferation, as described in Alberts et al MOLECULAR BIOLOGY OF THE CELL (second edition, Garland publishing New York, 1989) pp. 699 and 705. The precise mechanism of the action of ras remains unknown, as indicated in Lowenstein et al *Cell* 70: 431–42 (1992) and Gale et al *Nature* 363: 88–92 (1993).

By expression interaction cloning, the GRB2 SH3 domains were found to bind to a GRB2-associated signaling inositol polyphosphate 5-phosphatase (called SIP-110), a 110 kDa protein believed to be involved in signaling events that follow growth factor stimulation, and occur between the cell surface and transcriptional activation events. Furthermore, SIP-110 is believed to participate in modulating signaling by ras and by phosphatidyl inositol 3-kinase (PI 3-kinase), two known regulators of cell growth. It would be advantageous in the process of elucidating the mechanism of ras, PI 3-kinase and other signaling molecules and pathways, to discover other signaling molecules that participate in the signal transduction that modulates the activity of the ras pathway, the PI 3-kinase pathway, the MAP kinase pathway, the calcium signaling pathway and other signaling pathways such that cellular responses including growth and proliferation may be regulated by regulating such signaling molecules.

Activation of phosphatidylinositol 3'-kinase (PI 3-kinase) by growth factors and oncogenes has been implicated as a critical step in mitogenic signaling and cellular transformation, as described in Cantley et al, *Cell* 64:281–302 (1991), Kapeller and Cantley. *Bioessays* 16:565–76 (1994), and Stephens et al, *Biochim BiophysActa* 1179:27–75 (1993), PI 3-kinase consists of 85 kDa and 110 kDa subunits which associate with receptor tyrosine kinases and intracellular signaling molecules in response to treatment with growth factors or in transformed cells. Blockade of PI 3-kinase function either by mutagenesis or with pharmacological inhibitors prevents mitogenic signaling. Further, two products of PI 3-kinase, PtdIns(3,4,5)P$_3$ and PtdIns(3,4)P$_2$, increase in cells treated with mitogenic stimuli as Hawkins, et al. *Nature* 358:157–910, (1992) and Klippel et al, *Molecular and Cellular Biology* 16:41174127 (1996). The products of PI 3-kinase are presumed to act as second messengers or as regulators of protein-protein interactions. The regulation of PI 3-kinase activity during signaling is less well studied. Changes in subcellular localization, in phosphorylation state and in conformation of the enzyme have been suggested to contribute to activation but little is known about how PI 3-kinase might be down-regulated. It would be advantageous to discover and characterize molecules implicated in PI 3-kinase mediated pathways, as a means to learning how to regulate PI 3-kinase.

SUMMARY OF THE INVENTION

The invention is an isolated signaling inositol polyphosphate 5-phosphatase (SIP) polypeptide having a polypeptide including a sequence of 50 consecutive amino acids from SEQ ID No. 15(SIP 130) where the polypeptide has an activity including 5' phosphatase activity specific for a 3' phosphorylated substrate, and binding of a phosphotyrosine binding (PTB) domain contained within a Src homology-2 domain and Collagen (SHC) containing polypeptide. The invention is also a polynucleotide that encodes this polypeptide. A polynucleotide sequence encoding a functional portion of a polypeptide sequence of SEQ ID No. 15 is also part of the invention. A polynucleotide sequence encoding SEQ ID No. 15 is likewise an aspect of the invention, as is a polynucleotide sequence of SEQ ID No. 12.

The invention is also a method of producing a SIP polypeptide by introducing into a host cell a polynucleotide that encodes the polypeptide, and expressing the polypeptide in the host cell.

The invention is a modulator capable of modulating an activity including an activity of SIP polypeptide, a level of SIP mRNA transcription, and a level of SIP protein expression.

The invention is also a method of treating a mammal having or at risk for having a condition characterized by higher than normal levels of PI 3-kinase activity by providing a therapeutic agent including a SIP polypeptide, a polynucleotide encoding a SIP polypeptide, or a modulator of a SIP polypeptide, and administering an effective amount of this therapeutic agent to a mammal.

The invention is also method of treating a mammal having or at risk for having a condition characterized by higher than normal levels of mitogen activated protein (MAP) kinase activity by providing a therapeutic agent including a SIP polypeptide, a polynucleotide encoding a SIP polypeptide, or a modulator of a SIP polypeptide, and administering an effective amount of this therapeutic agent to a mammal.

The invention is also a method of reducing a level of phosphatidylinositol (3,4,5) triphosphate (PtdIns(3,4,5)P$_3$) in a cell in a mammal by providing a therapeutic agent including a SIP polypeptide, a polynucleotide encoding a SIP polypeptide, or a modulator of a SIP polypeptide, and administering an effective amount of this therapeutic agent to a mammal.

The invention is also a method of regulating mitogenic activity in a population of cells in a mammal by providing a therapeutic agent including a SIP polypeptide, a polynucleotide encoding a SIP polypeptide, or a modulator of a SIP polypeptide, and administering an effective amount of this therapeutic agent to a mammal.

The invention is a pharmaceutical composition for treating a mammal having a population of mitogenic cells having higher than normal levels of PI 3-kinase activity or higher than normal levels of MAP kinase activity using an effective amount of a therapeutic agent including a SIP polypeptide, a polynucleotide encoding a SIP polypeptide, a modulator of a SIP polypeptide, and a pharmaceutically acceptable carrier.

The invention is a pharmaceutical composition for treating a mammal having a condition characterized by higher than normal levels of phosphatidylinositol (3,4,5) polyphosphate (PtdIns(3,4,5)P$_3$) including an effective amount of a therapeutic agent including a SIP polypeptide, a polynucleotide encoding a SIP polypeptide, a modulator of a SIP polypeptide, and a pharmaceutically acceptable carrier.

The invention is also a pharmaceutical composition for treating a mammal having a condition characterized by a deficiency of an inositol polyphosphate 5-phosphatase including an effective amount of a therapeutic agent including a SIP polypeptide, a polynucleotide encoding a SIP polypeptide, a modulator of a SIP polypeptide, and a pharmaceutically acceptable carrier.

The invention includes also a polynucleotide sequence of a 5' untranslated region of SIP gene, for use in a regulatory function for regulating a heterologous coding sequence; a polynucleotide sequence of a 3' untranslated region of a SIP gene, for use in a regulatory function for regulating a heterologous coding sequence, and a polynucleotide sequence of a promoter region of a SIP gene, for use in a regulatory function for regulating a heterologous coding sequence.

It is an object of the present invention to provide novel polypeptides that participate in the signaling pathway that may regulate cell growth and proliferation. A further object of the invention is to provide novel polypeptides and derivatives that are capable of correcting an inositol polyphosphate 5-phosphatase deficiency, and to provide a pharmaceutical composition that includes such. It is another object of the present invention to provide polynucleotides that encode such novel polypeptides, or derivatives thereof, as well as vectors and host cells containing such. It is also an object of the present invention to provide modulators, including inhibitors, and including antibodies, to the novel polypeptides. It is another object of the present invention to provide methods of obtaining the novel polypeptides, polynucleotides, vectors and host cells described above. A further object of the invention is to provide for a method of producing a modulator of the polypeptides, including an antibody, polynucleotide, peptide, peptoid, or small molecule modulators.

It is also an object of the invention to provide a method of treating a mammal having or at risk for having a condition characterized by lower than normal levels of PI 3-kinase activity by providing a therapeutic agent that is an antagonist of a SIP polypeptide, and administering an effective amount of this therapeutic agent to the mammal. A further object of the invention is a method of treating a mammal having or at risk for having a condition characterized by lower than normal levels of mitogen activated protein (MAP) kinase activity by providing a therapeutic agent that is an antagonist of a SIP polypeptide, and administering an effective amount of this therapeutic agent to the mammal. The invention is also a method of increasing a level of phosphatidylinositol (3,4,5) triphosphate (PtdIns(3,4,5)P$_3$) in a cell in a mammal by providing a therapeutic agent that is an antagonist of a SIP polypeptide, and administering an effective amount of this therapeutic agent to the mammal. Another object is a method of stimulating cell growth in a population of cells in a mammal by providing a therapeutic agent that is an antagonist of a SIP polypeptide, and administering an effective amount of this therapeutic agent to the mammal.

Another object is a pharmaceutical composition for treating a mammal having a population of cells having lower than normal levels of PI 3-kinase activity or lower than normal levels of MAP kinase activity having an effective amount of a therapeutic agent that is an antagonist of a SIP polypeptide and a pharmaceutically acceptable carrier.

Another object is a pharmaceutical composition for treating a mammal having a condition characterized by lower than normal levels of phosphatidylinositol (3,4,5) polyphosphate (PtdIns(3,4,5)P$_3$) having an effective amount an antagonist of SIP polypeptide and a pharmaceutically acceptable carrier.

Another object is a method of reducing a level of inositol polyphosphates in a cell in a mammal by providing a therapeutic agent that is a SIP polypeptide, a polynucleotide encoding a SIP polypeptide, or a modulator of a SIP polypeptide, and administering an effective amount of this therapeutic agent to the mammal.

Another object is a method of increasing a level inositol polyphosphates in a cell in a mammal by providing a therapeutic agent that is an antagonist of a SIP polypeptide, and administering an effective amount of this therapeutic agent to the mammal.

Another object is a method of treating a mammal having or at risk for having a condition characterized by a higher than normal level of calcium signaling by providing a therapeutic including a SIP polypeptide, a polynucleotide encoding a SIP polypeptide, and a modulator of a SIP polypeptide, and administering an effective amount of this therapeutic agent to the mammal and administering an effective amount of this therapeutic agent to the mammal.

Another object is a method of treating a mammal having or at risk for having a condition characterized by lower than normal levels of calcium signaling by providing a therapeutic agent that is an antagonist of a SIP polypeptide, and administering an effective amount of this therapeutic agent to the mammal.

Another object is a pharmaceutical composition for treating a mammal having a population of cells exhibiting higher than normal levels of calcium signaling including an effective amount of a therapeutic agent that is a SIP polypeptide, a polynucleotide encoding a SIP polypeptide, or a modulator of a SIP polypeptide, and a pharmaceutically acceptable carrier.

Another object is a pharmaceutical composition for treating a mammal having a population of cells exhibiting lower than normal levels of calcium signaling including an effective amount of a therapeutic agent that is an antagonist of a SIP polypeptide and a pharmaceutically acceptable carrier.

BRIEF DESCRIPTION OF THE DRAWINGS

Figure 1C:
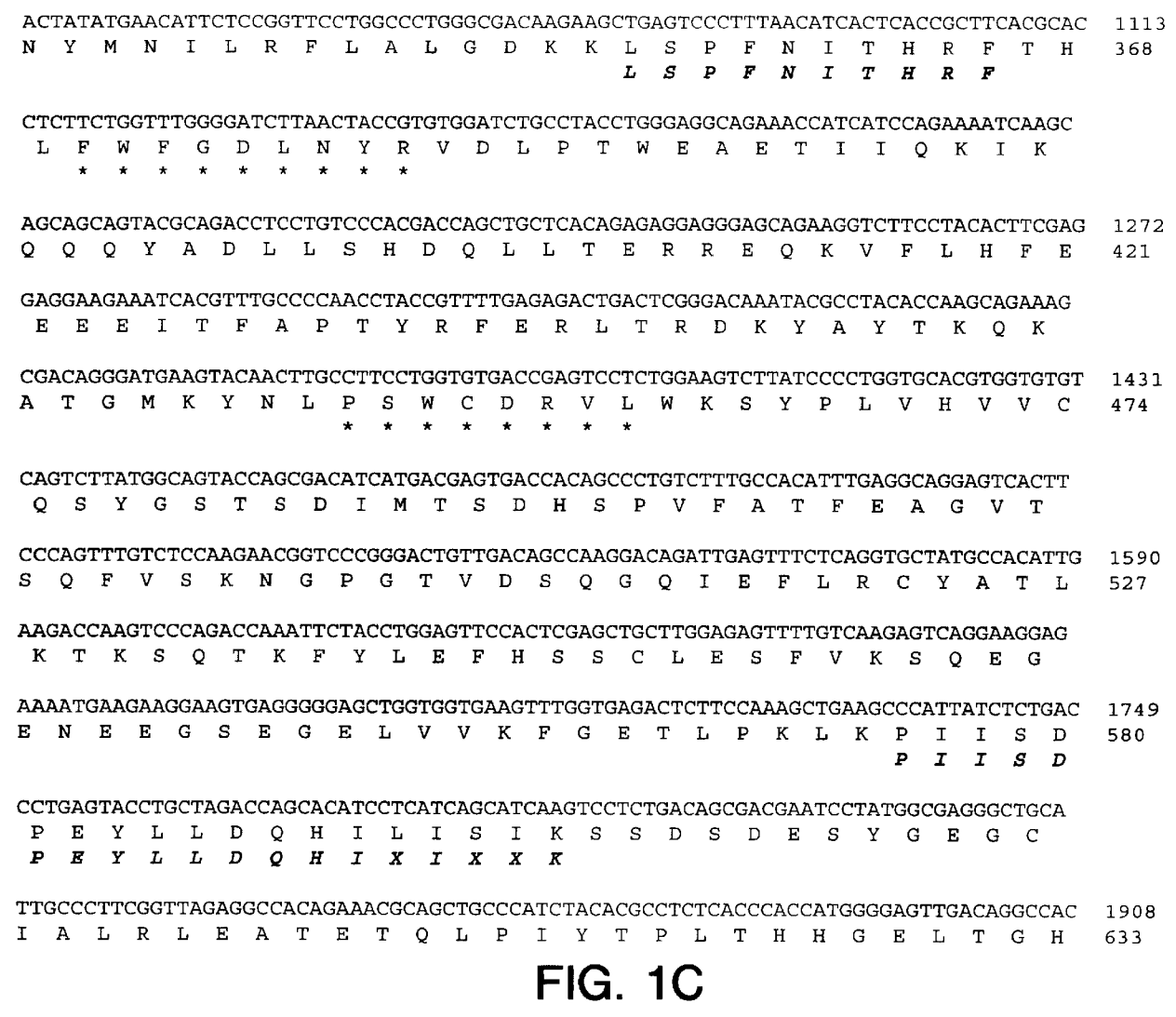

FIG. 1 is a schematic representation of cDNA and predicted amino acid sequences of SIP-110 and SIP-130. Sequence which is present in SIP-130 but not in SIP-110

(SEQ ID NO. 10) is in italics and is numbered separately from the full-length SIP-110 cDNA (SEQ ID NO. 11). The junction between SIP-130 (SEQ ID NO. 12) and SIP-110 (SEQ ID NO. 11) sequences is indicated by the large arrow. The predicted amino acid sequences of SIP-130 (SEQ ID NO. 15) and SIP-110 (SEQ ID NO. 14) are compared with peptide sequences obtained from purified p130 (bold italics indicates the mouse sequence; the sequence above that is the human sequence) (SEQ ID NO.s 1 and 5, 2 and 6, 3 and 7, 4 and 8, and 9 and 13) and p125 (bold type) (SEQ ID NO.s 25, 26, and 27) proteins. X denotes an undetermined residue. The in-frame stop codon 5' to SIP-110 ATG is in bold type (a TAA codon). Proline-rich SH3 binding motifs are indicated by bold underlined italics (SEQ ID NO.s 16, 17, 18, 19, and 20) and are also considered GRB2 binding sites. Shaded boxes highlight the two NPXY motifs presumed for SHC PTB domain binding (SEQ ID NO.s 31 and 32). The partial λgt11 clone of SIP-110 which binds GRB2 begins at SIP-110 nucleotide 2679 (small arrow) (SEQ ID NO. 21). The SH2 domain of SIP-130 is underlined (SEQ ID NO.s 23). Asterisks indicate the conserved sequence motifs which define the inositol polyphosphate 5-phosphatase family (SEQ ID NO. 24 and 33).

DETAILED DESCRIPTION

The invention described herein draws on previously published work and pending patent applications. By way of example, such work consists of scientific papers, patents or pending patent applications. All such published work cited herein are hereby incorporated by reference. The invention is not limited to any theories of action of the elements of the invention.

Definitions

An "isolated polypeptide" or "isolated polynucleotide" as used herein refers to a polypeptide or polynucleotide, respectively, produced in vivo or in vitro in an environment manipulated by humans using state of the art techniques of molecular biology, biochemistry and gene therapy. For example, an isolated polypeptide can be produced in a cell free system by automated peptide or polypeptide synthesis, in heterologous host cells transformed with the nucleic acid sequence encoding the polypeptide and regulatory sequences for expression in the host cells, and in an animal into which the coding sequence of the polypeptide has been introduced for expression in the animal. A polypeptide or polynucleotide is "isolated" for purposes herein to the extent that it is not present in its natural state inside a cell as a product of nature. For example, such isolated polypeptides or polynucleotides can be 10% pure, 20% pure, or a higher degree of purity.

The term "inositol polyphosphate 5-phosphatase family" as used herein refers to a family of phosphatases each of which removes the 5 phosphate from inositol- and phosphatidylinositol- polyphosphates. The family of proteins is determined by the substrate specificity of these enzymes and by amino acid sequence homology. A description of some of the aspects of the family is provided in Jefferson and Majerus, *J Biol Chem* 270: 9370–77 (1995).

The term "activated T cell" and "activated B cell" refers to T and B cells that have been stimulated, for example, with cytokines or growth factors, or which have had their antigen receptors cross-linked using antibodies, all of which events stimulate gene expression, cell proliferation or other responses in T and B cells.

The term "tyrosine phosphorylated" as used herein refers to the addition of a phosphate group at a tyrosine residue. Generally, tyrosine phosphorylation of polypeptides is associated with activation or inactivation of signaling pathways. Tyrosine phosphorylation is also associated with activation or inhibition of signaling molecules. Tyrosine phosphorylation of a polypeptide of the invention can occur in response to, for example, B or T cell activation. In some cases, binding to other polypeptides occurs before, after, or during the tyrosine phosphorylation of a polypeptide.

The term "SHC PTB domain" or "PTB domain" as used herein refers to the phosphotyrosine binding (PTB) domain of an Src Homology 2 Collagen (or SHC) protein. The PTB domain was originally identified as a 186-residue segment of the signaling protein SHC which binds specifically to a tyrosine-phosphorylated form of proteins in response to many growth factors, as described in Kavanaugh and Williams, *Science* 266:1862–1865 (1994). In addition to having a PTB domain, SHC also has an SH2 domain.

The term "apparent molecular weight" as used herein refers to the molecular weight of the protein or polypeptide as it migrates on a polyacrylamide gel under reducing or non-reducing conditions. The "apparent" molecular weight may be accounted for by glycosylations or other moieties that alter the molecular weight of the polypeptide alone.

The term "SIP protein" as used herein refers to any of the following proteins, each of which is distinguished from the others by apparent molecular weight, amino acid sequence differences, and nucleic acid sequence differences. All the SIP proteins have some sequence homology with proteins of the SIP family. SIP proteins include a protein of an apparent molecular weight of approximately 130–135 kDa (SIP-130), which binds the PTB domain of a SHC protein, and to a protein with homology to SIP-130 but no homology to SIP-110 and possessing an SH2 domain called SIP-N. SIP has been variously reported to have a molecular mass of 130, 140, 145 or 150 kDa. Recombinant SIP-130 migrated at the exact same apparent molecular weight as the largest form of endogenous SIP present in either lysates or anti-SHC immunoprecipitates from B cells. These results strongly suggest that full-length SIP corresponds to SIP-130, contains residues 41–976, and has an apparent molecular mass of approximately 130–135 kDa. This form of SIP was therefore used in subsequent experiments. SIP-N is also described herein, and is depicted as SEQ ID NO. 29 (nucleic acid) and SEQ ID NO. 30 (amino acid). The term "SIP-110" as used herein refers to a polypeptide having a molecular weight of about 110 kDa (SEQ ID NO. 14) (GRB2-associated inositol polyphosphate 5-phosphatase or SIP-110). SIP-110 binds both SH3 (Src Homology 3) domains on the GRB2 protein, and modulates signaling of, for example, ras. In addition to having 2 SH3 domains, GRB2 also has an SH2 domain.

A "gene delivery vehicle" refers to a component that facilitates delivery to a cell of a coding sequence for expression of a polypeptide in the cell. The cell can be inside the mammal, as in in vivo gene therapy, or can be removed from the mammal for transfection and returned to the mammal for expression of the polypeptide as in ex vivo gene therapy. The gene delivery vehicle can be any component or vehicle capable of accomplishing the delivery of a gene to a cell, for example, a liposome, a particle, or a vector. A gene delivery vehicle is a recombinant vehicle, such as a recombinant viral vector, a nucleic acid vector (such as plasmid), a naked nucleic acid molecule such as genes, a nucleic acid molecule complexed to a polycationic molecule capable of neutralizing the negative charge on the nucleic acid molecule and condensing the nucleic acid molecule into a compact molecule, a nucleic acid associated with a liposome (Wang, et al., *PNAS* 84:7851, 1987), a bacterium, and certain eukaryotic cells such as a producer cell, that are capable of delivering a nucleic acid molecule having one or more desirable properties to host cells in an organism. As discussed further below, the desirable properties include the ability to express a desired substance, such as a protein, enzyme, or antibody, and/or the ability to provide a biological activity, which is where the nucleic acid molecule carried by the gene delivery vehicle is itself the active agent without requiring the expression of a desired substance. One example of such biological activity is gene therapy where the delivered nucleic acid molecule incorporates into a specified gene so as to inactivate the gene and "turn off" the product the gene was making. Gene delivery vehicle refers to an assembly which is capable of directing the expression of the sequence(s) or gene(s) of interest. The gene delivery vehicle will generally include promoter elements and may include a signal that directs polyadenylation. In addition, the gene delivery vehicle includes a sequence which, when transcribed, is operably linked to the sequence(s) or gene(s) of interest and acts as a translation initiation sequence. The gene delivery vehicle may also include a selectable marker such as Neo, $SV_2$ Neo, TK, hygromycin, phleomycin, histidinol, or DHFR, as well as one or more restriction sites and a translation termination sequence. Gene delivery vehicles as used within the present invention refers to recombinant vehicles, such as viral vectors (Jolly, *Cancer Gen. Therapy* 1:5164, 1994), nucleic acid vectors, naked DNA, cosmids, bacteria, and certain eukaryotic cells (including producer cells; see U.S. Ser. No. 08/240,030 and U.S. Ser. No. 07/800,921), that are capable of eliciting an immune response within an animal. Representative examples of such gene delivery vehicles include poliovirus (Evans et al., *Nature* 339:385–388, 1989; and Sabin, *J. Biol. Standardization* 1:115–118, 1973); rhinovirus; pox viruses, such as canary pox virus or vaccinia virus (Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973); SV40 (Mulligan et al., *Nature* 277:108–114, 1979); retrovirus (U.S. Pat. No. 4,777,127, GB 2,200,651, EP 0,345,242, and WO 91/02805); influenza virus (Luytjes et al., *Cell* 59:1107–1113, 1989; McMicheal et al., *N. Eng. J. Med.* 309:13–17, 1983; and Yap et al., *Nature* 273:238–239, 1978); adenovirus (Berkner, *Biotechniques* 6:616–627, 1988; Rosenfeld et al., *Science* 252:431–434, 1991; WO 93/9191; Kolls et al., *PNAS* 91:215–219, 1994; Kass-Eisler et al., *PNAS* 90:11498–11502, 1993; Guzman et al., *Circulation* 88:2838–2848, 1993; Guzman et al., *Cir. Res.* 73:1202–1207, 1993; Zabner et al., *Cell* 75:207–216, 1993; Li et al., *Hum. Gene. Ther.* 4:403409, 1993; Caillaud et al., *Eur. J. Neurosci.* 5:1287–1291, 1993; Vincent et al., *Nat. Genet* 5:130–134, 1993; Jaffe et al., *Nat. Genet.* 1:372–378, 1992; and Levrero et al., *Gene* 101:195–202, 1991); parvovirus such as adeno-associated virus (Samulski et al., *J. Vir.* 63:3822–3828, 1989; Mendelson et al., *Virol.* 166:154–165, 1988; PA 7/222,684); herpes (Kit, *Adv. Exp. Med. Biol.* 215:219–236, 1989); SV40; HIV (Poznansky, *J. Virol.* 65:532–536, 1991); measles (EP 0 440,219); astrovirus (Munroe, S. S. et al., *J. Vir.* 67:3611–3614, 1993); Semlild Forest Virus, and coronavirus, as well as other viral systems (e.g., EP 0,440,219; WO 92/06693; U.S. Pat. No. 5,166,057). In addition, viral carriers may be homologous, non-pathogenic(defective), replication competent virus (e.g., Overbaugh et al., *Science* 239:906–910,1988), and nevertheless induce cellular immune responses, including cytotoxic T-cell lymphocytes (CTL).

The term "in vivo administration" refers to administration to a mammal a polynucleotide encoding a polypeptide for expression in the mammal. In particular, direct in vivo administration involves transfecting a mammal's cell with a coding sequence without removing the cell from the mammal. Thus, direct in vivo administration may include direct injection of the DNA encoding the polypeptide of interest in the region of interest resulting in expression in the mammal's cells.

The term "ex vivo administration" refers to transfecting a cell, for example, a cell from a population of cells that are exhibiting aberrant or absence of SIP activity, after the cell is removed from the mammal. After transfection the cell is then replaced in the mammal. Ex vivo administration can be accomplished by removing cells from a mammal, optionally selecting for cells to transform, rendering the selected cells incapable of replication, transforming the selected cells with a polynucleotide encoding a gene for expression, including also a regulatory region for facilitating the expression, and placing the transformed cells back into the mammal for expression of the SIP polypeptide.

"Biologically active" refers to a molecule that retains a specific activity. A biologically active SIP polypeptide, for example, retains its phosphatase ability, or also by example, its ability to bind the PTB (phosphotyrosine binding) domain of SHC. In general, biologically active means, in the case of a SIP polypeptide, retention of at least one activity normally associated with a native SIP polypeptide.

"Administration" or "administering" as used herein refers to the process of delivering to a mammal a therapeutic agent, or a combination of therapeutic agents. The process of administration can be varied, depending on the therapeutic agent, or agents, and the desired effect. Administration can be accomplished by any means appropriate for the therapeutic agent, for example, by parenteral, mucosal, pulmonary, topical, catheter-based, and oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Administration will generally also include delivery with a pharmaceutically acceptable carrier., such as, for example, a buffer, a polypeptide, a peptide, a polysaccharide conjugate, a liposome, and a lipid. A gene therapy protocol is considered an administration in which the therapeutic agent is a polynucleotide capable of accomplishing a therapeutic goal when expressed as a transcript or a polypeptide in the mammal.

"Co-administration" refers to administration of one or more therapeutic agents in course of a given treatment of a mammal. The agents may be administered with the same pharmaceutical carrier, or different carriers. They may be administered by the same administration means, for example intramuscular injection, or different means, for example also oral administration in an enteric coated capsule, or nasal spray. The agents may be the same type of agent or different types of agents, for example polynucleotides, polypeptide, or small molecules. The time of administration may be exactly the same time, or one therapeutic agent may be administered before or after another agent. Thus a co-administration can be simultaneous, or consecutive. The exact protocol for a given combination of therapeutic agents it determined considering the agents and the condition being treated, among other considerations.

A "nucleic acid molecule" or a "polynucleotide," as used herein, refers to either RNA or DNA molecule that encodes a specific amino acid sequence or its complementary strand. Nucleic acid molecules may also be non-coding sequences, for example, a ribozyme, an antisense oligonucleotide, or an untranslated portion of a gene. A "coding sequence" as used herein, refers to either RNA or DNA that encodes a specific amino acid sequence or its complementary strand. A polynucleotide may include, for example, an antisense oligonucleotide, or a ribozyme, and may also include such items as a 3' or 5' untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and may also be modified with chemical moieties to render the molecule resistant to degradation. Synthetic nucleic acids can be ribozymes or antisense molecules, for example. Modifications to synthetic nucleic acid molecules include nucleic acid monomers or derivative or modifications thereof, including chemical moieties. For example, phosphothioates can be used for the modification. A polynucleotide derivative can include, for example, such polynucleotides as branched DNA (bDNA). A polynucleotide can be a synthetic or recombinant polynucleotide, and can be generated, for example, by polymerase chain reaction (PCR) amplification, or recombinant expression of complementary DNA or RNA, or by chemical synthesis.

The term "an expression control sequence" or a "regulatory sequence" refers to a sequence that is conventionally used to effect expression of a gene that encodes a polypeptide and include one or more components that affect expression, including transcription and translation signals. Such a sequence includes, for example, one or more of the following: a promoter sequence, an enhancer sequence, an upstream activation sequence, a downstream termination sequence, a polyadenylation sequence, an optimal 5' leader sequence to optimize initiation of translation in mammalian cells, a Kozak sequence, which identifies optimal residues around initiator AUG for mammalian cells. The expression control sequence that is appropriate for expression of the present polypeptide differs depending upon the host system in which the polypeptide is to be expressed. For example, in prokaryotes, such a control sequence can include one or more of a promoter sequence, a Shine-Dalgarno sequence, a ribosomal binding site, and a transcription termination sequence. In eukaryotes, for example, such a sequence can include a promoter sequence, and a transcription termination sequence. If any necessary component of an expression control sequence is lacking in the nucleic acid molecule of the present invention, such a component can be supplied by the expression vector to effect expression. Expression control sequences suitable for use herein may be derived from a prokaryotic source, an eukaryotic source, a virus or viral vector or from a linear or circular plasmid. Further details regarding expression control sequences are provided below. An example of a regulatory sequence is the human immunodeficiency virus ("HIV-1") promoter that is located in the U3 and R region of the HIV-1 long terminal repeat ("LTR"). Alternatively, the regulatory sequence herein can be a synthetic sequence, for example, one made by combining the UAS of one gene with the remainder of a requisite promoter from another gene, such as the GADP/ADH2 hybrid promoter.

Any "polypeptide" of the invention, including a native or altered SIP polypeptide, includes any part of the protein including the mature protein, and further include truncations, variants, alleles, analogs and derivatives thereof. Variants can be spliced variants expressed from the same gene as the related protein. Unless specifically mentioned otherwise, such a polypeptide possesses one or more of the bioactivities of the protein, including for example protease activity, or inhibition of a protease. This term is not limited to a specific length of the product of the gene. Thus, polypeptides that are identical or contain at least 60%, preferably 70%, more preferably 80%, and most preferably 90% homology to the target protein or the mature protein, wherever derived, from human or nonhuman sources are included within this definition of a polypeptide. Also included, therefore, are alleles and variants of the product of the gene that contain amino acid substitutions, deletions, or insertions. The amino acid substitutions can be conservative amino acid substitutions or substitutions to eliminate nonessential amino acid residues such as to alter a glycosylation site, a phosphorylation site, an acetylation site, or to alter the folding pattern by altering the position of the cysteine residue that is not necessary for function, etc. Conservative amino acid substitutions are those that preserve the general charge, hydrophobicity/hydrophilicity and/or steric bulk of the amino acid substituted, for example, substitutions between the members of the following groups are conservative substitutions: Gly/Ala, Val/Ille/Leu, Asp/Glu, Lys/Arg, Asn/Gln, Ser/Cys/Thr and Phe/Trp/Tyr. Analogs include peptides having one or more peptide mimics, also known as peptoids, that possess the target protein-like activity. Included within the definition are, for example, polypeptides containing one or more analogs of an amino acid (including, for example, unnatural amino acids, etc.), polypeptides with substituted linkages, as well as other modifications known in the art, both naturally occurring and nonnaturally occurring. The term "polypeptide" also does not exclude post-expression modifications of the polypeptide, for example, glycosylations, acetylations, phosphorylations, myristoylations and the like.

The term "binding pair" refers to a pair of molecules capable of a binding interaction between the two molecules. Usually a binding interaction furthers a cell signal or cellular event. The term binding pair can refer to a protein/protein, protein-DNA, protein-RNA, DNA—DNA, DNA-RNA, and RNA—RNA binding interactions, and can also include a binding interaction between a small molecule, a peptoid, or a peptide and a protein, DNA, or RNA molecule, in which the components of the pair bind specifically to each other with a higher affinity than to a random molecule, such that upon binding, for example, in case of a ligand/receptor interaction, the binding pair triggers a cellular or an intracellular response. An example of a ligand/receptor binding pair is a pair formed between PDGF (platelet derived growth factor) and a PDGF receptor. An example of a different binding pair is an antigen/antibody pair in which the antibody is generated by immunization of a host with the antigen. Another example of a binding pair is the formation of a binding pair between a protease and a protease inhibitor, or a protease substrate and a protease inhibitor. Specific binding indicates a binding interaction having a low dissociation constant, which distinguishes specific binding from non-specific, background, binding. Inhibition of a biological interaction can be accomplished by inhibiting an in vivo binding interaction such as, for example, a DNA-protein interaction. Such inhibition can be accomplished, for example, by an inhibitor that bind the protein, or by an inhibitor that binds the DNA, in either case, thus preventing the original endogenous binding interaction, and so the biological activity that follows from it.

"Homology" refers to the degree of similarity between x and y. The correspondence between the sequence from one form to another can be determined by techniques known in the art. For example, they can be determined by a direct comparison of the sequence information of the polynucleotide. Typically, two sequences, either polynucleotide or polypeptide, are homologous if the sequences exhibit at least 45% sequence identity; more typically, 50% sequence identity; more typically, 55% sequence identity; more typically, 60% sequence identity; more typically, 65% sequence identity; even more typically, 70% sequence identity. Usually, two sequences are homologous if the sequences exhibit at least 75% sequence identity; more usually, 80% sequence identity; even more usually, 85% 75% sequence identity; even more usually, 90% sequence identity; and even more usually, 95% sequence identity. Alternatively, homology can be determined by hybridization of the polynucleotides under conditions which form stable duplexes between homologous regions. Stable duplexes are those, for example, which would withstand digestion with a single-stranded specific nuclease(s), such as $S_1$. Such duplexes can be analyzed by various methods, such as size determination of digested fragments.

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor their binding hydrogen bonding. Factors that affect this binding bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al. MOLECULAR CLONING; A LABORATORY MANUAL, SECOND EDITION (1989), Volume 2, chapter 9, pages 9.47 to 9.57. "Stringency" refers to conditions in a hybridization reaction that favor association of very similar sequences over sequences that differ. For example, the combination of temperature and salt concentration should be chosen that is approximately 12° to 20° C. below the calculated $T_m$ of the hybrid under study.

The term "naked DNA" refers to polynucleotide DNA for administration to a mammal for expression in the mammal. The polynucleotide can be, for example, a coding sequence, and the polynucleotide DNA can be directly or indirectly connected to an expression control sequence that can facilitate the expression of the coding sequence once the DNA is inside a cell. The direct or indirect connection is equivalent from the perspective of facilitating the expression of the DNA in the mammal's cells, and merely allows the possibility of the inclusion of other sequences between the regulatory region and the coding sequence that may facilitate the expression further, or may merely act a linker or spacer to facilitate connecting the two polynucleotide regions together to form a nonviral vector.

"Recombinant retroviral vector" refers to an assembly which is capable of directing the expression of a sequence(s) or gene(s) of interest. Preferably, the retroviral vector construct should include a 5' LTR, a tRNA binding site, a packaging signal, one or more heterologous sequences, an origin of second strand DNA synthesis and a 3' LTR. A wide variety of heterologous sequences may be included within the vector construct, including for example, sequences which encode a protein (e.g., cytotoxic protein, disease-associated antigen, immune accessory molecule, or replacement protein), or which are useful in and of themselves (e.g., as ribozymes or antisense sequences). Alternatively, the heterologous sequence may merely be a "stuffer" or "filler" sequence of a size sufficient to allow production of retroviral particles containing the RNA genome. Preferably, the heterologous sequence is at least 1, 2, 3, 4, 5, 6, 7 or 8 Kb in length. The retroviral vector construct may also include transcriptional promoter/enhancer or locus defining element (s), or other elements which control gene expression by means such as alternate splicing, nuclear RNA export, post-translational modification of messenger, or post-transcriptional modification of protein. Optionally, the retroviral vector construct may also include selectable markers that confer resistance of recombinant retroviral vector, transduced or transfected, cells to TK, hygromycin, phleomycin, histidinol, or DHFR, as well as one or more specific restriction sites and a translation termination sequence.

The term "fusion protein" or "fusion polypeptide" refers to the recombinant expression of more than one heterologous coding sequence in a vector or contiguous connection such that expression of the polypeptide in the vector results in expression of one polypeptide that includes more than one protein or portion of more than one protein. Fusion proteins can be called chimeric proteins. Most optimally, the fusion protein retains the biological activity of the polypeptide units from which it is built, and preferably, the fusion protein generates a synergistic improved biological activity by combining the portion of the separate proteins to form a single polypeptide. A fusion protein can also be created with a polypeptide that has function and a peptide or polypeptide that has no function when expressed, but which serves a purpose for the expression of the polypeptide with activity. Examples of fusion proteins useful for the invention include any SIP fusion protein engineered to some advantage for a therapeutic or other use.

A "therapeutically effective amount" is that amount that will generate the desired therapeutic outcome. For example, if the therapeutic effect desired is reduction or arrest of uncontrolled growth in a population of cells, the therapeutically effective amount is that amount that facilitates the reduction or arrest of cell growth. A therapeutically effective amount can be an amount administered in a dosage protocol that includes days or weeks of administration, for example. Where the therapeutic effect is a reduction of the effects of uncontrolled cell growth in the mammal, for example, the effective amount of an agent to accomplish this in the mammal will be that amount that results in, for example, tumor regression, or reduced hyperproliferation of a population of cells.

A "therapeutic agent" as used herein can be any agent that accomplishes or contributes to the accomplishment of one or more of the therapeutic elements of the invention. For example, where the therapeutic agent is a polynucleotide designed to express a SIP polypeptide, that agent will be a polynucleotide that can be administered to and expressed in a cell in the mammal. Thus, the active form of the agent will initially be the expressed polypeptide. A SIP therapeutic agent is a therapeutic agent with the bioactivity of SIP or a therapeutic agent derived from native SIP. Optimally, a therapeutic agent will achieve a therapeutic goal, alone or in combination with other agents, for example, the use of other known treatments for a particular condition used in conjunction with administration of SIP or a modulator of SIP, or a gene delivery vehicle capable of facilitating expression of SIP or a modulator of SIP in the mammal. The therapeutic agents including for example agonists or antagonists of SIP, for example, a small organic molecule, a peptide, a peptoid, a polynucleotide, or a polypeptide SIP or SIP modulatory therapeutic agent.

A "combination therapeutic agent" is a therapeutic composition having several components or agents that produce their separate effects when administered together, and perhaps maybe also produce a synergistic effect when administered together to treat a disease. Preferably, the separate effects of the combination therapeutic agent combine to result in a larger therapeutic effect, for example recovery from a disease manifesting PI 3-kinase activity, or MAP kinase activity, or activities associated with products of the PI 3-kinase or MAP kinase pathways, and long term survival. An example of separate effects resulting from administration of a combination therapeutic agent is the combination of such effects as short-term, or long-term remission, or decrease of an auto-immune response to a particular type of cell in the patient. An example of a combination therapeutic agent of this invention would be administration of a gene delivery vehicle including a polynucleotide encoding a mutant or native SIP polypeptide, or a polypeptide capable of modulating SIP activity, administered in a viral vector, followed with administration of another drug to treat the particular condition. For example, thymidine kinase can be administered with SIP as a prodrug activator, in the event a prodrug is required later to kill the gene delivery vehicle expression system in the mammal. Also by example, a chemotherapeutic agent can be administered to kill tumor cells along with the polynucleotide encoding a SIP polypeptide or a modulator of SIP activity. The various therapeutic agents can be administered in the same pharmaceutically acceptable carrier at the same time, followed, perhaps, for example, by repeated administrations of one or all of the individual agents as needed to make the therapy efficacious.

The term "pharmaceutically acceptable carrier" refers to a carrier for administration of a therapeutic agent, such as, for example, a polypeptide, polynucleotide, small molecule, peptoid, or peptide, refers to any pharmaceutically acceptable carrier that does not itself induce the production of antibodies harmful to the individual receiving the composition, and which may be administered without undue toxicity.

"Vector construct" refers to an assembly which is capable of directing the expression of the sequence(s) or gene(s) of interest. The vector construct must include transcriptional promoter/enhancer or locus defining element(s), or other elements which control gene expression by other means such as alternate splicing, nuclear RNA export, post-translational modification of messenger, or post-transcriptional modification of protein. In addition, the vector construct must include a sequence which, when transcribed, is operably linked to the sequence(s) or gene(s) of interest and acts as a translation initiation sequence. Optionally, the vector construct may also include a signal which directs polyadenylation, a selectable marker such as Neo, TK, hygromycin, phleomycin, histidinol, or DHFR, as well as one or more restriction sites and a translation termination sequence. In addition, if the vector construct is placed into a retrovirus, the vector construct must include a packaging signal, long terminal repeats (LTRs), and positive and negative strand primer binding sites appropriate to the retrovirus used (if these are not already present).

"Tissue-specific promoter" refers to transcriptional promoter/enhancer or locus defining elements, or other elements which control gene expression as discussed above, which are preferentially active in a limited number of tissue types. Representative examples of such tissue-specific promoters include the PEP-CK promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, a or P globin promoters, T-cell receptor promoter, or the osteocalcin promoter.

"Event-specific promoter" refers to transcriptional promoter/enhancer or locus defining elements, or other elements which control gene expression as discussed above, whose transcriptional activity is altered upon response to cellular stimuli. Representative examples of such event-specific promoters include thymidine kinase or thymidilate synthase promoters, a or P interferon promoters and promoters that respond to the presence of hormones (either natural, synthetic or from other non-host organisms, e.g., insect hormones).

The term "derivative" as used herein in reference to a polypeptide or a polynucleotide means a polypeptide or polynucleotide that retains the functionality of the polypeptide or polynucleotide to which it is a derivative. They may be variously modified by amino acid deletions, substitutions, insertions or inversions by, for example, site directed mutagenesis of the underlying nucleic acid molecules. Derivatives of a polypeptide or polynucleotide may also be fragments thereof. In any case, a derivative, or a fragment, retains at least some, and preferably all of the function of the polypeptide from which it is derived.

"Mammalian cell" as used herein refers to a subset of eukaryotic cells useful in the invention as host cells, and includes human cells, and animal cells such as those from dogs, cats, cattle, horses, rabbits, mice, goats, pigs, etc. The cells used can be genetically unaltered or can be genetically altered, for example, by transformation with appropriate expression vectors, marker genes, and the like. Mammalian cells suitable for the method of the invention are any mammalian cell capable of expressing the genes of interest, or any mammalian cells that can express a cDNA library, cRNA library, genomic DNA library or any protein or polypeptide useful in the method of the invention. Mammalian cells also include cells from cell lines such as those immortalized cell lines available from the American Type Culture Collection (ATCC). Such cell lines include, for example, rat pheochromocytoma cells (PC12 cells), embryonal carcinoma cells (P19 cells), Chinese hamster ovary (CHO) cells, HeLa cells, baby hamster kidney (BHK) cells, monkey kidney cells (COS), human hepatocellular carcinoma cells (e.g., Hep G2), human embryonic kidney cells, mouse sertoli cells, canine kidney cells, buffalo rat liver cells, human lung cells, human liver cells, mouse mammary tumor cells, as well as others. Also included are hematopoetic stem cells, neuronal stem cells such as neuronal sphere cells, and embryonic stem cells (ES cells).

The term "antagonist" as used herein refers to a molecule that blocks signaling, as for example, a molecule that can bind a receptor, but which does not cause a signal to be transduced by the receptor to the cell. In the case of signaling inositol polyphosphatase 5'-phosphatases (SIPs), an antagonist might block signaling by a SIP by binding the SIP, for example, at an SH2 domain on the SIP molecule, or by binding the SIP, for example, so as to inhibit its phosphatase activity. In general, an antagonist of a SIP polypeptide is an inhibitor of any biological activity of the SIP polypeptide. A given inhibitor or agonist may target and inhibit one biological activity, while not affecting another non-target activity of the molecule.

The term "agonist" as used herein refers to a molecule that mimics the signaling in the pathway under study, for example, by binding a receptor and promoting a signal transduction to the cell through the receptor. In the case of signaling inositol polyphosphatase 5'-phosphatases (SIPs), an agonist might mediate signaling by a SIP by binding the SIP in a way that promotes signaling by the SIP to other protein molecules; or an agonist might mimic the signaling accomplished by a SIP and bind protein targets of SIPs, thereby promoting signaling. Agonists and antagonists or inhibitors, are modulators of a given biological activity or molecule.

The inventors herein have discovered a novel polypeptides of apparent molecular weight of about 130–135 kDa of the inositol polyphosphate 5-phosphatase family. The 130–135 kDa polypeptide is named signaling inositol polyphosphate 5-phosphatase or SIP-130. SIP can also be called SHIP for SH2-containing Inositol Phosphatase. SIP associates with the SHC protein through its PTB domain Additionally, the inventors have identified SIP-N, a SIP that contains homology to the amino terminus of SIP-130, but no homology with SIP-110, the 110 kDa polypeptide member of the SIP family.

In one embodiment of the present invention, the novel polypeptides can be purified from extracts of cells stimulated by to treatment of cells with, for example, growth factors such as platelet-derived growth factor (PDGF), and fibroblast growth factor (FGF), and other stimulating factors such as, for example, leukemia inhibitory factor, interleukin-(IL-6). The novel polypeptides can also be extracted from activated T cells and B cells. These polypeptides can be purified by any conventional means. For example, the supernatants from the pelleted homogenized cells can be separated by anti-phosphotyrosine antibody affinity chromatography. Column fractions can be assayed for the presence of the polypeptides binding to SHC PTB domain by, for example, human SHC PTB domain expressed as a glutathione-S-transferase (GST) fusion protein in bacteria or Sf9 cells and labeled. The labeled fusion protein can be used to monitor the purification process.

Fractions can be further separated by dialysis, anion exchange chromatography, and by SDS-PAGE, or by other means standard in the art of peptide purification.

For identification of the amino acid sequences of the novel polypeptides they can be digested with endoproteinase Lys-C to yield peptide fragments for sequencing. The peptide sequencing can be done by standard methods. The sequences of these peptides can then be compared to known polypeptides in a database such as, for example, the database GenBank. The polypeptide fragments can be used as the basis of construction of oligonucleotide probes for probing cDNA libraries, such as a human λgt11 cDNA library, to obtain a cDNA molecule that encodes the polypeptide. The inventors herein have discovered that certain peptide sequences obtained by endoproteinase Lys-C digestion of the novel polypeptides herein have substantial sequence homology to the amino acid sequence of SIP-110.

A SIP-110 sequence has been identified by expression cloning characterized by its binding to GRB2 SH3 domains. SIP-110 possesses an apparent molecular weight of about 110 kDa. SIP-110 can be obtained by expression by using radiolabeled human GRB2 protein to screen a human library made from tissue known to contain signaling molecules, such as, for example, a human placental λgt11 cDNA library, as described in Blanar & Rutter, *Science* 256: 1014–8 (1992). Duplicate filters can be probed with antiphosphotyrosine antibody to identify and eliminate SH2 domain-mediated interactions. Clones that interacted with GRB2 and are not tyrosine phosphorylated can be considered positives. This interaction will be specific for GRB2. Full length SIP-110 has 4147 base pairs that encode a polypeptide of 976 amino acids. Sequencing of a cDNA clone can be accomplished by standard techniques, and will identify any open reading frame or portion thereof of the polypeptide. The predicted 110 kDa protein will contain proline-rich motifs and will have significant homology to the inositol 5-phosphatases. SIP-110 is formerly called GRB2-associated inositol polyphosphate 5-phosphatase (GAPtase or GA5Ptase). A point mutation in either of the two GRB2 or GA5Ptase). A point mutation in either of the two GRB2 SH3 domains will reduce or eliminate SIP-110 binding, where mutations in the SH2 domains will not have this effect, demonstrating that SIP-110 binds the SH3 domains of GRB2.

To clone SIP-130, cDNA was generated by reverse transcription of total or mRNA of cells or tissues known to have signaling proteins such as, for example, human lung, placental, or liver tissue, human HepG2 liver, Balb/c fibroblast, BAL 17 B cell, and others to yield cDNA for a library. The cDNA was ligated into an appropriate library vector, such as, for example, pCMV-Sport plasmid, λgt10, λgt11, and any other appropriate vector, and screened with SIP-110 DNA probes of varying lengths. The probes were, for example, a DNA probe from any region of SIP-110. A preferred sequence for the probe was a sequence conserved within the family of inositol polyphosphate 5-phosphatases, such as, for example, a sequence selected from those sequences described in Jefferson and Majerus, *J Biol Chem* 270: 9370–77 (1995).

The cDNA generated from the above described tissues was subjected to polymerase chain reaction (PCR) using specific primers from, for example, one or more SIP-110 sub-sequences, specific primers from the arms of the library vector, degenerate primers derived from the polypeptide sequence of a purified polypeptide of about 130–135 kDa, and conserved sequences from the inositol polyphosphate 5-phosphatase family. The PCR products were generated by standard PCR techniques, and once generated, were compared. The products that were in the size range of the expected size of SIP coding sequence based on SIP amino acid content and polypeptide size were cloned into sequencing vectors or sequenced from the PCR mixture directly.

To further identify positive clones representing p130, those sequences that have some identity with SIP-110, but also contain unique p130 sequences will represent the gene sequence of the novel polypeptides herein. The unique p130 peptide sequences are represented in mouse and human sequence in SEQ ID No.s 1 and 5, 2 and 6, 3 and 7, 4 and 8, and 9 and 13. Peptide sequence of p125 polypeptide are represented in SEQ ID No.s 25, 26, and 27. SIP-N was generated by using SIP-130 polynucleotide probes and screening a cDNA library.

The genomic DNA sequence of the present novel polypeptides can be identified by screening genomic DNA libraries, for example, those made from human placental tissue or other tissue, with any SIP sequence. The genomic DNA can be used to identify the sequences that regulate mRNA expression, to determine the intron and exon organization of the gene and, because exons usually represent functional domains within a protein, to determine the possible functional domains of the protein and understand how SIP functions in cells. Knowing the intron and exon organization will identify any splice variants that exist and their exact relationship to one another.

Once identified, either by hybridization to homologous DNA probes, or by RT/PCR, the polynucleotide sequence encoding the novel polypeptide can be ligated into vectors for sequencing and/or cloning and expression, and mutagenesis. Vectors appropriate for sequencing include vectors for which sequencing primers are known and easily available, such as, for example, T7 and SP6 promoter primers for use in sequencing from a vector established for use with these primers. Vectors appropriate for expression of the polypeptides include any vector including regulatory sequences for controlling expression. Host cells for replication of the polynucleotide clone and for expression of the polypeptide include any host cell, prokaryotic or eukaryotic, for accomplishing replication or expression of the polynucleotide and polypeptide. The regulatory sequences can be any regulatory sequence operable for expression of the polypeptides of the invention. The sequence can be heterologous to the polypeptide, and/or heterologous to the host cell, having the only requirement that promotes cloning or expression of the polynucleotide or polypeptide within the cloning or expression system. The host cells, if eukaryotic, can be fungal cells, insect cells, fish cells, amphibian cells, avian cells, crustacean cells and mammalian cells.

The coding regions of SIP-N and SIP-130 can be expressed in any conventional expression system for expressing such proteins and polypeptides. Examples of such expression systems are provided below. Expression of large quantities of the polypeptide is useful for therapeutic applications, and for further studies on the polypeptide.

In addition, further manipulation of the SIP gene using any expression system known in the art, including but not limited to those listed below, can be accomplished by conventional mutagenesis or alteration of the coding sequence of SIP and subsequent expression of the altered gene. This can be done in order to generate a SIP that is incompetent for signaling, for example, for use in diagnosis of a ras activation pathway, the PI 3-kinase pathway, a MAP kinase pathway, a calcium signaling pathway, or for diagnosis of another signaling pathway in which SIP or SHC is in involved, or for use in therapeutic interruption of cell proliferation. Additionally, inhibitors of SIP can be used to activate these pathways, in a therapeutic or other context. Because it is known that SIP-N and SIP-130 each contain an SH2 domain, a domain that mediates interactions with specific tyrosine-phosphorylated proteins, it is likely that SIP-N and SIP-130 are important signaling molecules.

Based on the presence of SH2 domains, new protein partners of SIP-N and SIP-130 can be identified by using standard biochemical or expression cloning techniques. For example, a library could be screened by the yeast 2-hybrid system as described U.S. Pat. No. 5,283,173 for proteins that bind the SH2 domains of the SIP molecules, or for proteins that bind SIP molecules at any other part of the SIP molecule.

An isolated polypeptide can thus be found having a first domain that, upon tyrosine phosphorylation, is capable of forming a binding pair with a PTB domain of SHC, and a second domain having a peptide sequence that possesses at least 70% amino acid sequence homology to one selected from the group consisting of (a) (SEQ ID NO: 1), (b) (SEQ ID NO: 2), (c) (SEQ ID NO: 3), (d) (SEQ ID NO: 4) and (e) (SEQ ID NO: 13). This isolated polypeptide can have an amino acid sequence that is obtainable from a cell of an activated T cell, an activated B cell, a cell capable of responding to treatment by PDGF, a cell capable of responding to treatment by FGF, a cell capable of responding to treatment by leukemia inhibitory factor, and a cell capable of responding to treatment by interleukin-6, wherein the polypeptide is capable of binding to a PTB domain of SHC to form a binding pair. This isolated polypeptide can be a polypeptide capable of binding to antibodies to form a binding pair, where the antibodies are obtained from the serum of an animal immunized with a composition having a peptide that includes an epitope of SIP-110. The epitope of SIP-110 can be selected from the amino acid residues 48–231, amino acid residues 232–500, and amino acid residues 891–969 of SIP-110. The isolated polypeptide can have an apparent molecular weight of about 130–135 kDa. The isolated polypeptide can generate, upon digestion with endoproteinase Lys-C, a peptide having an amino acid sequence (SEQ ID NO: 5), wherein X represents an amino acid residue. The isolated polypeptide can generate, upon digestion with endoproteinase Lys-C, a peptide having an amino acid sequence (SEQ ID NO: 6), wherein X represents an amino acid residue. The isolated polypeptide can generate, upon digestion with endoproteinase Lys-C, a peptide having an amino acid sequence (SEQ ID NO: 7), where X represents an amino acid residue. The isolated polypeptide can generate, upon digestion with endoproteinase Lys-C, a peptide having an amino acid sequence (SEQ ID NO: 8), wherein X represents an amino acid residue. The isolated polypeptide can generate, upon digestion with endoproteinase Lys-C, a peptide having an amino acid sequence (SEQ ID NO: 9), wherein X represents an amino acid residue.

A pharmaceutical composition having the isolated polypeptide described above and a pharmaceutically acceptable carrier is also part of the invention, as is an isolated polynucleotide having a nucleotide sequence that encodes the polypeptide described, and a pharmaceutical composition having this polynucleotide along with a pharmaceutically acceptable carrier. The polynucleotide can be RNA, intron-free DNA, genomic DNA and complementary strands thereof. A recombinant vector having this polynucleotide and a regulatory control sequence that is capable of controlling the expression of the polynucleotide is also part of the invention, as is a host cell having the vector. The host cell can be a fungal cell, an insect cell, a fish cell, an amphibian cell, an avian cell, a crustacean cell, or a mammalian cell. The invention also includes application of standard molecular biology techniques to produce the SIP polypeptide(s) described, including production of the polypeptide in a fungal cell, an insect cell, a fish cell, an amphibian cell, an avian cell, a crustacean cell, or a mammalian cell. The standard techniques can include providing an oligonucleotide probe that encodes a sequence of at least 4 consecutive amino acid residues of the polypeptide; probing a nucleic acid library with the oligonucleotide; and isolating a clone that hybridizes with the oligonucleotide under stringent conditions to form a binding pair. This method can use at least 4 consecutive amino acid residues of the human sequences of (SEQ ID NO: 1), (SEQ ID NO. 2), (SEQ ID NO. 3), (SEQ ID NO. 4), (SEQ ID NO. 13) or the mouse sequences of (SEQ ID NO: 5), (SEQ ID NO. 6), (SEQ ID NO. 7), (SEQ ID NO. 8), and (SEQ ID NO. 9). The invention also includes producing a recombinant vector having a SIP polypeptide.

Further, the invention includes an antibody produced by injecting a composition having at least one epitope of the SIP polypeptide(s) described herein into a mammal, and obtaining serum from the mammal, and the antibody is capable of forming a binding pair with the SIP polypeptide. The antibody can be modified to be a single chain antibody or a humanized antibody, and a hybridoma can be made that is capable of producing such an antibody. Further, the antibody can be a polyclonal or a monoclonal antibody.

The invention contemplates a modulator of a SIP polypeptide, and the modulator can be an antibody, a peptide, a peptoid, a small molecule inhibitor, or a fragment of a polypeptide and the modulator can modulate a biological activity of the SIP polypeptide. A type of modulator can be an inhibitor of SIP biological activity. The invention is also a method of treating a disease characterized by a deficiency of an inositol polyphosphate 5-phosphatase in a mammal by administering to the mammal a SIP polypeptide or a biologically active derivative of SIP, or a modulator of SIP, any of which have the capability of correcting the deficiency. The disease can be Lowe's oculocerebralrenal disease, or can be a disease characterized by abnormal cell growth. The inositol polyphosphate 5-phosphatase deficiency in a mammal can be corrected by administering to the mammal a pharmaceutical composition having a SIP polypeptide, or a modulator of SIP biological activity.

A small molecule inhibitor of a SIP polypeptide can be found by allowing the SIP polypeptide to contact a kinase in the presence of a composition comprising candidate small molecule inhibitors to form a mixture, determining the presence of inhibition of phosphorylation in the mixture; and identifying a molecule in the mixture that is responsible for any inhibition. A small molecule inhibitor of SIP polypeptide can also be found by allowing the polypeptide to contact a PTB domain of SHC in the presence of a composition comprising candidate small molecule inhibitors to form a mixture; determining the presence of inhibition of binding of the polypeptide to the PTB domain; and identifying a molecule in the mixture that is responsible for any inhibition. Further, a method of identifying a small molecule inhibitor of a SIP polypeptide can be accomplished by allowing the polypeptide to contact an inositol polyphosphate or phosphotidylinositol polyphosphate in the presence of a composition comprising candidate small molecule inhibitors to form a mixture; determining the presence of inhibition of hydrolysis in the mixture; and identifying a molecule in the mixture that is responsible for any inhibition. The inositol polyphosphate can be inositol 1,3,4,5 tetrakisphosphate and the phosphotidylinositol polyphosphate can be phosphotidylinositol (3,4,5) trisphosphate. Yet another method of identifying a small molecule inhibitor to a SIP polypeptide can be accomplished by allowing the SIP polypeptide to contact GRB2 in the presence of a composition having candidate small molecule inhibitors to form a mixture; determining the presence of inhibition of binding to GRB2; and identifying a molecule in the mixture that is responsible for any inhibition.

The invention includes a polynucleotide sequence having a functional portion of SEQ ID NO: 29 connected to a heterologous polynucleotide sequence; a polynucleotide sequence having a functional portion of SEQ ID NO: 12 connected to a heterologous polynucleotide sequence; a functional portion of a polypeptide sequence represented by SEQ ID NO: 30; and a functional portion of a polypeptide sequence represented by SEQ ID NO: 15.

The invention includes a method of attenuating 5-phosphatase signaling mediated by SH2 domain binding to other polypeptides by providing a polynucleotide encoding a portion of a 5-phosphatase containing an SH2 domain; and expressing the polynucleotide in a mammal. This method can include a portion of a 5-phosphatase containing an SH2 domain including SIP-N and SIP-130.

The invention is also a method of identifying inhibitors of 5-phosphatase signaling activity by providing a SIP; using the SIP in a yeast 2-hybrid screen of a cDNA library; identifying a polypeptide expressed by the cDNA library that forms a binding pair with the SIP and screening a candidate inhibitor for ability to disrupt the binding pair just identified. The SIP can be SIP-110 or SIP-130.

The invention includes a method of treating a cell or a mammal having a condition or disease characterized by signaling mediated by polyphosphate 5-phosphatase activity by providing an inhibitory amount of an antagonist of 5-phosphatase activity; and administering the antagonist to the cell or the a mammal having the condition or disease. The invention is also a method of treating a cell or mammal having a condition or disease characterized by signaling mediated by polyphosphate 5-phosphatase activity by providing a stimulatory amount of an agonist of 5-phosphatase activity; and administering the agonist to the cell or to the mammal. The 5-phosphatase activity can be SIP-110 or SIP-130 activity. The agonist or antagonist can be a small molecule, a peptide, a peptoid, a polypeptide, or a polynucleotide. The disease can be characterized by cells growing slower than normal, or by proliferating cells. In either case, the cell growth is expected to be abnormal.

In the case where an antagonist of SIP is administered, either to a cell or a mammal, the conditions that can be treated in the mammal include, for example, stroke, myocardial infarction, or an immunodeficiency state. In the case where SIP or an agonist of SIP is administered, the conditions that can be treated include for example, cancer and other cell proliferative disorders. Additionally, SIP polypeptide or a polynucleotide encoding a SIP, an agonist of SIP, or an antagonist of SIP can be administered for modulating a calcium signaling pathway. For example, where the pathway is to be inhibited, a SIP polypeptide can be administered. For example, where the pathway is to be stimulated, an antagonist of SIP is can be administered. SIP polypeptides are capable of hydrolyzing inositol polyphosphates which have been shown to be involved in calcium signaling.

The invention includes a polynucleotide sequence of a 5' untranslated region of a SIP gene, for use in a regulatory function for regulating a heterologous coding sequence. This polynucleotide sequence can have a regulatory function of stabilizing a heterologous sequence or directing localization of a heterologous sequence. This polynucleotide can include an expression cassette from which expression of said heterologous sequence is placed under regulatory control of the 5' untranslated region of the SIP gene. The invention includes also a polynucleotide sequence of a 3' untranslated region of a SIP gene, for use in a regulatory function for regulating a heterologous coding sequence. The regulatory function can be stabilizing a heterologous sequence or directing localization of a heterologous sequence. The polynucleotide sequence can be part of an expression cassette from which expression of said heterologous sequence is placed under regulatory control of the 3' untranslated region of the SIP gene. The invention includes also a polynucleotide sequence of a promoter region of a SIP gene, for use in a regulatory function for regulating a heterologous coding sequence. This promoter sequence can be part of an expression cassette from which expression of the heterologous sequence is placed under regulatory control of a promoter region of a SIP gene. The invention includes also a polynucleotide sequence of an intron of a SIP gene, for use in a regulatory function for regulating a heterologous coding sequence. The SIP intron can be part of an expression cassette from which expression of the heterologous sequence is placed under regulatory control of the intron of the SIP gene.

The invention is an isolated signaling inositol polyphosphate 5-phosphatase (SIP) polypeptide having a polypeptide having a sequence of 50 consecutive amino acids from SEQ ID No. 15 (SIP 130) wherein said polypeptide has an activity selected from the group consisting of 5' phosphatase activity specific for a 3' phosphorylated substrate, and binding of an SHC (Src Homology-2 domain and collagen) polypeptide at a phosphotyrosine binding (PTB) domain. Further, this polypeptide exhibits 60% or more of the activity of SIP. The polypeptide just described where the polypeptide has 5' phosphatase activity specific for a 3' phosphorylated substrate including a phosphatidylinositol substrate and a phosphorylated inositol polyphosphatase substrate. The invention includes a polynucleotide encoding this SIP polypeptide; a polynucleotide sequence encoding a functional portion of a polypeptide sequence of SEQ ID No. 15; a polynucleotide sequence encoding SEQ ID No. 15.; a polynucleotide sequence of SEQ ID No. 12; an mRNA molecule capable of hybridizing to the polynucleotide of SEQ ID No. 12 under stringent conditions; a polypeptide translated from an mRNA molecule capable of hybridizing to said polynucleotide of SEQ ID No. 12 under stringent conditions; recombinant vector having the polynucleotide sequence that encodes a SIP polypeptide; a recombinant vector, having a polynucleotide sequence encoding a mutant form of a SIP polypeptide; a recombinant vector, having a polynucleotide sequence encoding a chimeric protein including a SIP polypeptide; and host cells transformed with any of the recombinant vector including SIP polynucleotide sequences.

The invention is also a method of producing a SIP polypeptide by introducing into a host cell a polynucleotide that encodes the SIP polypeptide, and expressing the polypeptide in the host cell. An antibody that binds to a SIP polypeptide is also part of the invention. The invention also includes a modulator capable of modulating an activity including an activity of SIP polypeptide, a level of SIP mRNA transcription, or a level of SIP protein expression. The modulator can be a polynucleotide, a polypeptide, a small molecule, a peptide, and a peptoid. A polynucleotide modulator can be a coding sequence or a noncoding sequence; and where the modulator is a noncoding sequence, the noncoding sequence can be a 3' untranslated region, a 5' untranslated region, an antisense oligonucleotide, or a ribozyme. The modulator can be a polypeptide and the polypeptide can be an antibody. The SIP modulator can be an antagonist or an agonist.

Thus, the inventors have discovered a method reducing a level of PI 3kinase activity in a cell having higher than normal levels of PI 3-kinase activity by providing a therapeutic agent including either a SIP polypeptide or a modulator of a SIP polypeptide, or a polynucleotide encoding a SIP polypeptide, and contacting the cell with an effective amount of the therapeutic agent.

The invention also is a method reducing a level of mitogen activated protein (MAP) kinase activity in a cell having higher than normal levels of MAP kinase activity by providing a therapeutic agent including a SIP polypeptide, a polynucleotide encoding a SIP polypeptide, and a modulator of a SIP polypeptide, and contacting the cell with an effective amount of the therapeutic agent.

The invention is also a method of reducing a level of phosphatidylinositol (3,4,5) triphosphate (PtdIns(3,4,5)P$_3$) in a cell by providing a therapeutic agent including a SIP polypeptide, a polynucleotide encoding a SIP polypeptide, or a modulator of a SIP polypeptide, and contacting the cell with an effective amount of the therapeutic agent.

The invention is also a method of regulating mitogenic activity in a cell by providing a therapeutic agent including a SIP polypeptide, a polynucleotide encoding a SIP polypeptide, or a modulator of a SIP polypeptide, and contacting the cell with an effective amount of the therapeutic agent.

The invention is also a pharmaceutical composition for treating a mammal having a population of mitogenic cells having higher than normal levels of PI 3-kinase activity or higher than normal levels of MAP kinase activity including an effective amount of a therapeutic agent including a SIP polypeptide, a polynucleotide encoding a SIP polypeptide, a polypeptide encoding a functional portion of the sequence of SEQ ID No. 15, or a modulator of a functional portion of the sequence of SEQ ID No. 15, and administering an effective amount of this therapeutic agent to the mammal. This pharmaceutical composition can include a therapeutic agent that is a modulator of a functional portion of the sequence of SEQ ID No. 15, and this modulator can be a polynucleotide, a polypeptide, a small molecule, a peptide, or a peptoid. The pharmaceutical composition can include a modulator that is a polynucleotide and the polynucleotide can be a coding sequence or a noncoding sequence. The pharmaceutical composition can be a polynucleotide modulator of SIP that is a noncoding sequence, and the noncoding sequence can be a 3' untranslated region, a 5' untranslated region, an antisense oligonucleotide, or a ribozyme.

The invention includes a pharmaceutical composition for treating a mammal having a condition characterized by higher than normal levels of phosphatidylinositol (3,4,5) polyphosphate (PtdIns(3,4,5)P$_3$) including an effective amount of a therapeutic agent including a SIP polypeptide, a polynucleotide encoding a SIP polypeptide, or a modulator of a functional portion of the sequence of SEQ ID No. 15, and a pharmaceutically acceptable carrier. This pharmaceutical composition can include a therapeutic agent that is a modulator of a functional portion of the sequence of SEQ ID No. 15, and the modulator can be a polynucleotide, a polypeptide, a small molecule, a peptide, and a peptoid.

The invention further includes a pharmaceutical composition for treating a mammal having a condition characterized by a deficiency of an inositol polyphosphate 5-phosphatase including an effective amount of a therapeutic agent including a SIP polypeptide, a polynucleotide encoding a SIP polypeptide, or a modulator of a functional portion of the sequence of SEQ ID No. 15, and a pharmaceutically acceptable carrier. This pharmaceutical composition can be used to treat a mammal that has Lowe's oculocerebralrenal disease. This pharmaceutical composition can be used to treat a condition characterized by abnormal cell growth.

The invention includes a polynucleotide sequence of a 5' untranslated region of SIP gene, for use in a regulatory function for regulating a heterologous coding sequence; a polynucleotide sequence of a 3' untranslated region of a SIP gene, for use in a regulatory function for regulating a heterologous coding sequence; a polynucleotide sequence of a promoter region of a SIP gene, for use in a regulatory function for regulating a heterologous coding sequence; and such a polynucleotide sequence further including an expression cassette from which expression of said heterologous sequence is placed under regulatory control of a promoter region of a SIP gene.

The invention is a method of increasing a level of PI 3-kinase activity in a cell having lower than normal levels of PI 3-kinase activity by providing a therapeutic agent that is an antagonist of a SIP polypeptide, and contacting the cell with an effective amount of the therapeutic agent.

Likewise, the invention is also a method increasing a level of MAP kinase activity in a cell having lower than normal levels of MAP kinase activity by providing a therapeutic agent that is an antagonist of a SIP polypeptide, and contacting the cell with an effective amount of the therapeutic agent.

The invention is also a method of increasing a level of phosphatidylinositol (3,4,5) triphosphate (PtdIns(3,4,5)P$_3$) in a cell by providing a therapeutic agent that is an antagonist of a SIP polypeptide, and contacting the cell with an effective amount of the therapeutic agent.

The invention is also a method of stimulating cell growth in a cell by providing a therapeutic agent that is an antagonist of a SIP polypeptide, and contacting the cell with an effective amount of the therapeutic agent.

The invention is also a pharmaceutical composition for treating a mammal having a population of cells having lower than normal levels of PI 3-kinase activity or lower than normal levels of MAP kinase activity having an effective amount of a therapeutic agent that is an antagonist of a SIP polypeptide and a pharmaceutically acceptable carrier. The pharmaceutical composition just described can include an antagonist of a SIP polypeptide that is a polynucleotide, a polypeptide, a small molecule, a peptide, or a peptoid. Further, the antagonist can be a polynucleotide that is a coding sequence or a noncoding sequence. The polynucleotide that is a noncoding sequence, can be a 3' untranslated region, a 5' untranslated region, an intron, an antisense oligonucleotide, or a ribozyme.

The invention is also a pharmaceutical composition for treating a mammal having a condition characterized by lower than normal levels of phosphatidylinositol (3,4,5) polyphosphate (PtdIns(3,4,5)P$_3$) having an effective amount of a therapeutic agent that is an antagonist of a SIP polypeptide and a pharmaceutically acceptable carrier.

The invention is also a pharmaceutical composition for treatment of a condition that is characterized by retarded cell growth or apoptosis. For example, the condition can be characterized by abnormally slow cell growth, or where apoptosis of the cells exists in higher than normal level, or predominates, and which may be characterized by low PI 3-kinase and/or low MAP kinase activity. Examples of such disease states are stroke, myocardial infarction, or immunodeficiency states where cells are dying from apoptosis. In these contexts, a SIP inhibitor or antagonist will increase cell survival and preserve cell function.

The invention is also a method of reducing a level of inositol polyphosphates in a cell by providing a therapeutic agent selected from the group consisting of a SIP polypeptide, a polynucleotide encoding this polypeptide, or a modulator of this polypeptide, and contacting the cell with an effective amount of the therapeutic agent.

The invention is also a method of increasing a level inositol polyphosphates in a cell by providing a therapeutic agent that is an antagonist of a SIP polypeptide, and contacting the cell with an effective amount of the therapeutic agent.

The invention is also a method reducing a level of calcium signaling in a mammal having a condition characterized by a higher than normal level of calcium signaling by providing a therapeutic agent selected from the group consisting of a SIP polypeptide, a polynucleotide encoding this polypeptide, or a modulator of this polypeptide, and contacting the cell with an effective amount of the therapeutic agent.

The invention is also a method of increasing a level of calcium signaling in a cell having lower than normal levels of calcium signaling by providing a therapeutic agent that is an antagonist of a SIP polypeptide, and contacting the cell with an effective amount of the therapeutic agent.

The invention is also a pharmaceutical composition for treating a mammal having a population of cells exhibiting higher than normal levels of calcium signaling having an effective amount of a therapeutic agent that is a SIP polypeptide, a polynucleotide encoding a SIP polypeptide, and a modulator of a SIP polypeptide, and a pharmaceutically acceptable carrier.

The invention is also a pharmaceutical composition for treating a mammal having a population of cells exhibiting lower than normal levels of calcium signaling having an effective amount of a therapeutic agent that is an antagonist of a SIP polypeptide and a pharmaceutically acceptable carrier.

Functional portions of the SIP polypeptide can be used to design therapeutic agents for treating appropriate conditions. For example, the SIP-derived sequence could be used to act as a dominant/negative to inhibit SIP function, delivered, for example, in a gene delivery vehicle. SIP analogues can also be designed to agonize SIP activity in cells. Parts or all of a SIP protein, could be synthetically constructed and placed in a vector for expression, for delivery to a mammal for expression in the mammal, or for delivery as a recombinant protein therapeutic agent. Administration of the polynucleotides derived from a SIP sequence could follow, to be accomplished by any means known for administration of polynucleotides for expression in a mammal, including, for example, liposomes, gels, matrices, injection of naked DNA, and covalent or non-covalent attachment of the polynucleotide to a carrier. The polynucleotide could be administered to the patient for expression in the patient, either systemically, or locally, depending on the nature of the condition being treated. Expression of an active SIP domain, for example, could then act to block SIP signaling, or to mimic it.

The cloned SIP gene can be used to generate derivatives of the polypeptide by using conventional techniques of recombinant DNA technology for preparation of variously modified derivatives or fragments of the full length, native polypeptide. The modifications can be made, for example, by single or multiple amino acid deletions, substitutions, insertions, or inversions by, for example, means of site directed mutagenesis of the underlying DNA. Such fragments of SIP may possess at least one original useful activity of SIP. All the allelic variations, glycosylated versions, modifications and fragments resulting in derivatives of SIP are within the scope of the invention so long as they contain a functional segment of SIP and retain the essential characteristic SIP activity attributed to that functional segment.

Also, functional studies of SIP can be conducted by altering, for example, the domain of SIP that binds the (phosphotyrosine binding) PTB domain of (SH2 and collagen protein) SHC, (represented in SEQ ID Nos. 31 and 32), or the catalytic domain, expressing the altered polypeptide and identifying the necessary and sufficient moieties on SIP that permit or interrupt binding, or permit or interrupt catalytic activity as the case may be. Other functional studies on SIP can be conducted in a similar manner to determine the regions of SIP that interact with other proteins and to determine the functional domains of SIP that are responsible for SIP effects on, SHC-related signaling, other signaling, or any intracellular response attributable to SIP.

Functional utility of the polypeptide fragments that make up SIP can be elucidated by determining which polypeptides are responsible for signaling pathway modulation, or for a cellular response, for example, modulation of the ras pathway, modulation of a MAP kinase pathway, in both instances including potentiation, inhibition or activation, and modulation of the PI 3-kinase pathway including potentiation, inhibition or activation, or abnormal cell growth generally. Polypeptide fragments important in ras pathway modulation or PI 3-kinase pathway modulation, for example, may constitute polypeptides involved in binding the PTB domain, or other domains that are involved in the modulating, activating, inhibiting, or potentiating complex of polypeptides. With sequence knowledge of these polypeptide fragments, altered peptides that alter the signal, for example, by binding competitively but without the ability to transmit a signal, can be constructed and used therapeutically. Such polypeptide fragments and derivatives include, for example, polypeptides that act as a dominant negative modulators of the affected signaling pathway or the cellular response.

In addition, small molecule antagonists and agonists of SIP activity can be discovered by screening methods standard in the art, including those methods described herein. Such molecules can be screened by their ability to modulate, inhibit, or augment any activity attributable at least in part to the novel polypeptides herein, including, but not limited to ras pathway activation, PI 3 kinase pathway activation, the MAP kinase pathway, or other SIP related cellular responses or pathways. In this regard, molecules that inhibit SIP binding via the SH2 domain, or molecules that inhibit SIP-binding via a PTB domain of an SHC protein can be screened for. For example, the SH2 domain could be used to identify inhibitors of the binding of a SIP to important targets. These inhibitors could be, for example, phosphorylated peptides, peptide derivatives such as peptoids, small molecules, or polynucleotides.

Additionally, agonists of SIP signaling can be sought, for mimicking the activity of a SIP, for example, where a condition is characterized by lower than normal levels of SIP signaling, or by SIP signaling that represents an aberrant pathway from normal. Similarly, antagonists of SIP signaling can be sought, for blocking the signaling activity of a SIP by a variety of mechanisms including, for example, binding a SIP to prevent signaling, or binding the signaling molecule to prevent SIP binding. Agonists or antagonists can be, for example, phosphorylated peptides, peptide derivatives such as peptoids, small molecules, polynucleotides, or other polypeptides.

Any of the full-length, fragments, derivatives, or polypeptide inhibitors or antagonists of the invention can be cloned, expressed, or synthesized by standard recombinant DNA or chemical techniques. Some exemplary expression systems that can be applied for these purposes follow.

Expression Systems

Although the methodology described below is believed to contain sufficient details to enable one skilled in the art to practice the present invention, other constructs not specifically exemplified, such as plasmids, can be constructed and purified using standard recombinant DNA techniques as described in, for example, Sambrook et al. (1989), MOLECULAR CLONING: A LABORATORY MANUAL, 2nd ed. (Cold Spring Harbor Press, Cold Spring Harbor, N.Y.); and under current regulations described in United States Dept of HHS, NATIONAL INSTITUTE OF HEALTH (NLH) GUIDELINES FOR RECOMBINANT DNA RESEARCH.

Bacterial Expression

Control elements for use in bacteria include promoters, optionally containing operator sequences, and ribosome binding sites. Useful promoters include sequences derived from sugar metabolizing enzymes, such as galactose, lactose (lac) and maltose. Additional examples include promoter sequences derived from biosynthetic enzymes such as, tryptophan (trp), the β-lactamase (bla) promoter system, bacteriophage λPL, and T7. In addition, synthetic promoters can be used, such as the tac promoter. The P4actamase and lactose promoter systems, the alkaline phosphatase, tryptophan (trp) promoter system and hybrid promoters such as the tac promoter can also be used. However, other known bacterial promoters useful for expression of eukaryotic proteins are also suitable. A person skilled in the art would be able to operably ligate such promoters to the coding sequences of interest using linkers or adaptors to supply any required restriction sites. Promoters for use in bacterial systems also generally will contain a Shine-Dalgarno (SD) sequence operably linked to the DNA encoding the target polypeptide. For prokaryotic host cells that do not recognize and process the native target polypeptide signal sequence, the signal sequence can be substituted by a prokaryotic signal sequence.

The foregoing systems are particularly compatible with *Escherichia coli*. However, numerous other systems for use in bacterial hosts including Gram-negative or Gram-positive organisms such as Bacillus spp., Streptococcus spp., Streptomyces spp., Pseudomonas species such as *P. aeruginosa, Salmonella typhimurium,* or *Serratia marcescans,* among others.

Yeast Expression

Expression and transformation vectors, either extrachromosomal replicons or integrating vectors, have been developed for transformation into many yeasts. For example, expression vectors have been developed for, among others, the following yeasts: *Saccharomyces cerevisiae, Candida albicans; Candida maltosa,; Hansenula polymorpha, Kluyveromyces fragilis,; Kluyveromyces lactis,; Pichia guillerimondii,; Pichia pastoris,; Schizosaccharomyces pombe, Yarrowia lipolytica,* Aspergillus hosts such as *A. nidulans,* and *A. niger,; Trichoderma reesia,* as described in EP 244,234, and filamentous fungi such as, e.g., Neurospora, Penicillium, and Tolypocladium.

Control sequences for yeast vectors are known and include promoters regions from genes such as alcohol dehydrogenase (ADH), as described in EP 284,044, enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK), as described in EP 329,203. The yeast PHO5 gene, encoding acid phosphatase, also provides useful promoter sequences. Other suitable promoter sequences for use with yeast hosts include the promoters for 3-phosphoglycerate kinase, or other glycolytic enzymes, such as pyruvate decarboxylase, triosephosphate isomerase, and phosphoglucose isomerase. Inducible yeast promoters having the additional advantage of transcription controlled by growth conditions, include from the list above and others the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman, EP 073,657. Yeast enhancers also are advantageously used with yeast promoters. In addition, synthetic promoters which do not occur in nature also function as yeast promoters. Examples of hybrid promoters include promoters which consist of the regulatory sequences of either the ADH2, GAL4, GAL10, or PHO5 genes, combined with the transcriptional activation region of a glycolytic enzyme gene such as GAP or PyK, as described in EP 164,556. Furthermore, a yeast promoter can include naturally occurring promoters of non-yeast origin that have the ability to bind yeast RNA polymerase and initiate transcription.

Other control elements which may be included in the yeast expression vectors are terminators, and leader sequences which encode signal sequences for secretion. DNA encoding suitable signal sequences can be derived from genes for secreted yeast proteins, such as the yeast invertase gene and the a-factor gene. Alternatively, leaders of non-yeast origin, such as an interferon leader, also provide for secretion in yeast, as described in EP 060,057.

Methods of introducing exogenous DNA into yeast hosts are well known in the art, and typically include either the transformation of spheroplasts or of intact yeast cells treated with alkali cations.

Insect Expression

Baculovirus expression vectors (BEVs) are recombinant insect viruses in which the coding sequence for a foreign gene to be expressed is inserted behind a baculovirus promoter in place of a viral gene, for example polyhedrin, as described in U.S. Pat. No. 4,745,051.

An expression construct herein includes a DNA vector useful as an intermediate for the infection or transformation of an insect cell system, the vector generally containing DNA coding for a baculovirus transcriptional promoter, optionally but preferably, followed downstream by an insect signal DNA sequence capable of directing secretion of a desired protein, and a site for insertion of the foreign gene encoding the foreign protein, the signal DNA sequence and the foreign gene being placed under the transcriptional control of a baculovirus promoter, the foreign gene herein being the coding sequence of the desired polypeptide.

The promoter for use herein can be a baculovirus transcriptional promoter region derived from any of the over 500 baculoviruses generally infecting insects. Particularly suitable for use herein is the strong polyhedrin promoter of the baculovirus, which directs a high level of expression of a DNA insert, and the promoter from the gene encoding the p10 protein.

The plasmid for use herein usually also contains the polyhedrin polyadenylation signal, and a procaryotic ampicillin-resistance (amp) gene and an origin of replication for selection and propagation in *E. coli*. DNA encoding suitable signal sequences can also be included and is generally derived from genes for secreted insect or baculovirus proteins, such as the baculovirus polyhedrin gene, as well as mammalian signal sequences such as those derived from genes encoding human a-interferon; human gastin-releasing peptide; human IL-2; mouse IL-3, and human glucocerebrosidase. Other baculovirus genes in addition to the polyhedrin promoter may be employed to advantage in a baculovirus expression system. These include immediate-early (alpha), delayed-early (beta), late (gamma), or very late (delta), according to the phase of the viral infection during which they are expressed.

Currently, the most commonly used transfer vector that can be used herein for introducing foreign genes into AcNPV is pAc373. Many other vectors, known to those of skill in the art, can also be used herein. The techniques utilized herein are generally known to those skilled in the art and are fully described in Summers and Smith, A MANUAL OF METHODS FOR BACULOVIRUS VECTORS AND INSECT CELL CULTURE PROCEDURES, Texas Agricultural Experiment Station Bulletin No. 1555, Texas A & M University (1987); Smith et al., *Mol. Cell. Biol.* (1983)3: 2156, and Luckow and Summers (1989). The procedure for the cultivation of viruses and cells are described in Volkman and Summers, *J. Virol.* (1975) 19: 820–832 and Volkman, al., *J. Virol.* (1976) 19: 820–832.

Expression in Amphibian Cells

Expression of SIP polypeptide, derivatives, variants and fusions and polypeptide modulators can be conducted in the oocytes of amphibians. One amphibian particularly useful for this purpose is *Xenopus laevis* because of the capacity of the oocytes of this animal to express large libraries. Expression systems for *X. laevis* and other amphibians is established and expression conducted as described in Lustig and Kirschner, *PNAS* (1995) 92: 6234–38, Krieg and Melton (1987) *Meth Enzymol* 155:397–415 and Richardson et al. (1988) *Bio/technology* 6:565–570.

Mammalian Expression

The polypeptides of the present invention can be expressed in mammalian cells, such as HeLa cells, using promoters and enhancers that are functional in those cells. Synthetic non-natural promoters or hybrid promoters can also be used. For example, a T7T7/T7gene promoter can be constructed and used where the T7 polymerase is under the regulatory control of its own promoter and drives the transcription of the inserted coding sequence, which is placed under the control of another T7 promoter. Also suitable for use herein is the gene for the CCAAT/enhancer-binding protein C/EBPalpha. Typical promoters for mammalian cell expression include the SV40 early promoter, the CMV promoter, the mouse mammary tumor virus LTR promoter, the adenovirus major late promoter (Ad MLP), and the herpes simplex virus promoter, among others. Other non-viral promoters, such as a promoter derived from the murine metallothionein gene, will also find use in mammalian constructs.

Mammalian expression may be either constitutive or regulated (inducible), depending on the promoter. Typically, transcription termination and polyadenylation sequences will also be present, located 3' to the translation stop codon. Preferably, a sequence for optimization of initiation of translation, located 5' to the polypeptide coding sequence, is also present. Examples of transcription terminator/polyadenylation signals include those derived from SV40. Introns, containing splice donor and acceptor sites, may also be designed into the constructs of the present invention.

Enhancer elements can also be used herein to increase expression levels of the mammalian constructs. Examples include the SV40 early gene enhancer, and the enhancer/promoter derived from the long terminal repeat (LTR) of the Rous Sarcoma Virus, and human cytomegalovirus. A leader sequence can also be present which includes a sequence encoding a signal peptide, to provide for the secretion of the foreign protein in mammalian cells. Preferably, there are processing sites encoded between the leader fragment and the gene of interest such that the leader sequence can be cleaved either in vivo or in vitro. The adenovirus tripartite leader is an example of a leader sequence that provides for secretion of a foreign protein in mammalian cells.

Once complete, the mammalian expression vectors can be used to transform any of several mammalian cells. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. General aspects of mammalian cell host system transformations have been described in U.S. Pat. No. 4,399,216.

Mammalian cell lines available as hosts for expression are also known and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), human embryonic kidney cells, baby hamster kidney cells, mouse sertoli cells, canine kidney cells, buffalo rat liver cells, human lung cells, human liver cells, mouse mammary tumor cells, as well as others.

The mammalian host cells used to produce the polypeptides of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM1, Sigma) are suitable for culturing the host cells. In addition, any of the media described in Ham and Wallace, *Meth. Enz.* (1979) 58: 44, Barnes and Sato, *Anal. Biochem.* (1980) 102: 255, U.S. Pat. Nos. 4,767,704, 4,657,866, 4,927,762, or 4,560,655, WO 90/103430, WO 87/00195, and U.S. RE 30,985, may be used as culture media for the host cells. Any of these media may be supplemented as necessary with hormones and/or other growth factors such as insulin, transferrin, or epidermal growth factor, salts (such as sodium chloride, calcium, magnesium, and phosphate), buffers (such as HEPES), nucleosides (such as adenosine and thymidine), antibiotics (such as Gentamycin™ M drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The novel polypeptides of the present invention can further be used to generate monoclonal or polyclonal antibodies. These antibodies are useful to identify such polypeptides and immunoprecipitate, for example, SIP bound polypeptides, and are useful also to inhibit SIP activity for diagnostic purposes, or for in vivo therapeutic uses. Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50–200 µg/injection is typically sufficient Immunization is generally boosted 2–6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2–18 hours. The serum is recovered by centrifugation, for example, at about 1,000×g for 10 minutes. About 20–50 ml per bleed may be obtained from rabbits.

Monoclonal antibodies (MAbs) are prepared using the method of Kohler and Milstein, *Nature* (1975) 256: 495–96, or a modification thereof. Typically, a mouse or rat is immunized as described above. However, rather than bleeding the animal to extract serum, the spleen, and optionally several large lymph nodes, is removed and dissociated into single cells. If desired, the spleen cells may be screened, after removal of non-specifically adherent cells, by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium such as one containing, e.g., hypoxanthine, aminopterin, and thymidine (a "HAT" medium). The resulting hybridomas are plated by limiting dilution, and are assayed for the production of antibodies which bind specifically to the immunizing antigen, and which do not bind to unrelated antigens. The selected MAb-secreting hybridomas are then cultured either in vitro, e.g., in tissue culture bottles or hollow fiber reactors, or in vivo, as ascites in mice.

If desired, the antibodies, whether polyclonal or monoclonal, may be labeled using conventional techniques. Suitable labels include fluorophores, chromophores, radioactive atoms (particularly $^{32}P$ and $^{125}I$), electron-dense reagents, enzymes; and ligands having specific binding partners. Enzymes are typically detected by their activity. For example, horseradish peroxidase (HRP) is usually detected by its ability to convert 3,3,5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

The antibodies generated in this manner can be used in any conventional applications, including for diagnostic and therapeutic purposes. For example, as a diagnostic, it can be used in an immunoassay for identification or detection of a SIP polypeptide or a homologue thereof in a sample suspected of containing such. For this purpose, the antibodies can be labeled with a suitable marker, such as a radioactive label, and allowed to react with the sample. After an appropriate length of time, the sample can be examined for the presence of specific binding pairs. Presence of specific binding suggests that a SIP polypeptide or a homologue thereof is present in the sample.

The antibodies to the SIP polypeptide, polyclonal or monoclonal, and preferably monoclonal, can be used for therapeutic purposes for blocking the in vivo activity of the SIP polypeptide. Such antibodies will be compatible to the host to be treated. For example, for treatment of humans, the antibodies can be human monoclonal antibodies or humanized antibodies, as the term is generally known in the art. The humanized antibodies can be made by any number of conventional methods. For example, by cdr (complementarity determining region) grafting, veneering, phage library display, or by use of xeno-mouse. In cdr grafting, the coding regions of the cdr of murine antibodies are linked to the coding regions of the framework regions of human antibodies. In veneering, the canonical regions of the antibodies, including parts of the cdr and parts of the murine framework regions that are exposed on the surface of the molecule, are maintained as well as the murine cdr regions. The antibodies to be administered can be given in a therapeutically effective amount, and can be in the form of a pharmaceutical composition.

Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. The assays herein involve the use of labeled antibodies to the SIP polypeptide or labeled SIP polypeptides. The labels may be, for example, fluorescent, chemiluminescent, radioactive, or dye molecules. Assays which amplify the signals from the probe can also be used; examples of which are assays which utilize biotin and avidin, and enzyme labeled and mediated immunoassays, such as ELISA assays.

The enzyme-linked immunosorbent assay (ELISA) can be used, for example, to measure either antigen, the SIP polypeptide, concentration or the antibody to the SIP polypeptide concentration. This method depends upon conjugation of an enzyme to either the antigen or to the antibody, and uses the bound enzyme activity as a quantitative label. To measure the antibody concentration, the antigen is fixed to a solid phase, such as a microplate or plastic cup, incubated with dilutions of the sample to be tested. The mixture is then washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization calorimetrically. The enzyme activity bound is a direct function of the amount of antibody bound.

To measure antigen concentration, that is, SIP polypeptide concentration, a known specific antibody is fixed to the solid phase, the test material containing antigen is added. After incubation, the solid phase is washed, and a second enzyme-labeled antibody is added. After washing, substrate is added, and enzyme activity is estimated colorimetrically, and related to antigen concentration. Immunofluorescence assays can also be performed with such antibodies and antigens, as described in Hashido et al., *Biochem. Biophys. Res. Comm.* (1992) 187(3): 1241–1248.

Modulators of SIP activity can be screened for from small molecule libraries, including small organic molecules, peptides, and peptide derivatives known as peptoids. Modulators can also be derived from noncoding DNA sequences, for example, ribozymes and antisense polynucleotides. These modulators can be screened for agonist activity of SIP or antagonist activity of SIP, depending on the therapeutic goal.

Small Molecule Library Synthesis

Therapeutic agents of the invention can include peptides and peptoids derived from SIP polypeptide sequence, and can be designed or modified to accomplish improved biological activity over SIP polypeptide, such as, for example higher affinity for SIP receptor, or resistance to degradation in the mammal. Peptides and peptoids can be prepared synthetically in libraries for screening for a favored biological activity, for example, increased binding to SIP receptor. Exemplary synthesis of some of these small molecules are described below. The small molecules libraries designed based on variations in SIP receptor binding sites of a SIP polypeptide can be screened for ability to block PI 3kinase activity or MAP kinase activity, for example, in a cell-base assay in microwell plates, as described generally above, and more specifically in the examples.

Small molecule libraries that are peptide and peptoid derivatives of SIP are made as follows. A "library" of peptides may be synthesized and used following the methods disclosed in U.S. Pat. No. 5,010,175, (the '175 patent) and in PCT WO91/17823. In method of the '175 patent, a suitable peptide synthesis support, for example, a resin, is coupled to a mixture of appropriately protected, activated amino acids. The method described in WO91/17823 is similar but simplifies the process of determining which peptides are responsible for any observed alteration of gene expression in a responsive cell. The methods described in WO91/17823 and U.S. Pat. No. 5,194,392 enable the preparation of such pools and subpools by automated techniques in parallel, such that all synthesis and resynthesis may be performed in a matter of days.

Further alternative agents include small molecules, including peptide analogs and derivatives, that can act as stimulators or inhibitors of gene expression, or as ligands or antagonists. Some general means contemplated for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, Weinstein, B. ed., Marcell Dekker, Inc., publ. New York (1983). Moreover, substitution of D-amino acids for the normal L-stereoisomer can be carried out to increase the half-life of the molecule.

Peptoids, polymers comprised of monomer units of at least some substituted amino acids, can act as small molecule stimulators or inhibitors herein and can be synthesized as described in PCT 91/19735. Presently preferred amino acid substitutes are N-alkylated derivatives of glycine, which are easily synthesized and incorporated into polypeptide chains. However, any monomer units which allow for the sequence specific synthesis of pools of diverse molecules are appropriate for use in producing peptoid molecules. The benefits of these molecules for the purpose of the invention is that they occupy different conformational space than a peptide and as such are more resistant to the action of proteases.

Peptoids are easily synthesized by standard chemical methods. The preferred method of synthesis is the "sub-monomer" technique described by R. Zuckermann et al., *J. Am. Chem. Soc.* (1992)114:10646–7. Synthesis by solid phase techniques of heterocyclic organic compounds in which N-substituted glycine monomer units forms a backbone is described in copending application entitled. "Synthesis of N-Substituted Oligomers" filed on Jun. 7, 1995 and is herein incorporated by reference in fill. Combinatorial libraries of mixtures of such heterocyclic organic compounds can then be assayed for the ability to alter gene expression.

Synthesis by solid phase of other heterocyclic organic compounds in combinatorial libraries is also described in copending application U.S. Ser. No. 08/485,006 entitled "Combinatorial Libraries of Substrate-Bound Cyclic Organic Compounds" filed on Jun. 7, 1995, herein incorporated by reference in full. Highly substituted cyclic structures can be synthesized on a solid support by combining the submonomer method with powerful solution phase chemistry. Cyclic compounds containing one, two, three or more fused rings are formed by the submonomer method by first synthesizing a linear backbone followed by subsequent intramolecular or intermolecular cyclization as described in the same application.

Ribozymes and Antisense

Where the therapeutic agent is a ribozyme, the ribozyme can be chemically synthesized or prepared in a vector for a gene therapy protocol including preparation of DNA encoding the ribozyme sequence. The synthetic ribozymes or a vector for gene therapy delivery can be encased in liposomes for delivery, or the synthetic ribozyme can be administered with a pharmaceutically acceptable carrier. A ribozyme is a polynucleotide that has the ability to catalyze the cleavage of a polynucleotide substrate. Ribozymes can be prepared and used as described in Long et al.,, FASEB J. 7: 25 (1993) and Symons, Ann. Rev. Biochem. 61: 641 (1992), Perrotta et al.,, Biochem. 31: 16, 17 (1992); and U.S. Pat. No. 5,225,337, U.S. Pat. No. 5,168,053, U.S. Pat. No. 5,168,053 and U.S. Pat. No. 5,116,742, Ojwang et al.,, Proc. Natl. Acad. Sci. USA 89: 10802–10806 (1992), U.S. Pat. No. 5,254,678 and in U.S. Pat. No. 5,144,019, U.S. Pat. No. 5,225,337, U.S. Pat. No. 5,116,742, U.S. Pat. No. 5,168,053. Preparation and use of such ribozyme fragments in a hammerhead structure are described by Koizumi et al., Nucleic Acids Res. 17:7059–7071 (1989). Preparation and use of ribozyme fragments in a hairpin structure are described by Chowrira and Burke, Nucleic Acids Res. 20:2835 (1992).

The hybridizing region of the ribozyme or of an antisense polynucleotide may be modified by linking the displacement arm in a linear arrangement, or alternatively, may be prepared as a branched structure as described in Horn and Urdea, Nucleic Acids Res. 17:6959–67 (1989). The basic structure of the ribozymes or antisense polynucleotides may also be chemically altered in ways quite familiar to those skilled in the art.

Chemically synthesized ribozymes and antisense molecules can be administered as synthetic oligonucleotide derivatives modified by monomeric units. Ribozymes and antisense molecules can also be placed in a vector and expressed intracellularly in a gene therapy protocol.

Assay for function of SIP and modulators of SIP

Where the SIP polypeptide or modulator is directed to regulate PI 3kinase products, a small molecule, or other therapeutic can be screened for this function. Analysis of PI 3-kinase products in vivo can accomplished using oocytes that are labeled with [$^{32}$P]orthophosphate. Phospholipids can be extracted and analyzed by TLC and HPLC essentially as previously described in Klippel, et al, Molecular and Cellular Biology 16:41174127 (1996) and Liu et al, Molecular and Cellular Biology 15:3563–3570 (1995). Briefly, oocytes are injected with SIP cRNA, p110* cRNA or both, and incubated. Oocytes are then washed and either lysed directly (p110* experiments) or stimulated with insulin at room temperature. The oocytes were placed on ice, the buffer aspirated and lysed with vigorous vortexing and repeated pipeting. Chloroform is then added and the mixture vortexed to extract lipids. The extracts were then centrifuged and the lower, chloroform phase removed to a new tube, the interface material and aqueous layer re-extracted with an equal volume of chloroform and the organic phases combined. The extracts were then separated on thin layer chromatography, de-acylated and analyzed by HPLC as described in Klippel, et al, Molecular and Cellular Biology 16:4117–4127 (1996) and Liu et al, Molecular and Cellular Biology 15:3563–3570 (1995). PtdIns(3,4,5)P$_3$ was identified using $^{32}$P-labeled standards generated with p110* as described in Klippel, et al, Molecular and Cellular Biology 16:41174127 (1996). Production or lack of production of the PtdIns(3,4,5)P$_3$ is an indicator of the presence or the absence of PI 3kinase activity. Where SIP is inhibited, the PtdIns(3,4,5)P$_3$ will be made, and where SIP is not inhibited, or where SIP activity is agonized or mimicked, the PtdIns(3,4,5)P$_3$ will not be present after the assay.

Similarly, analysis of MAP kinase phosphorylation can be accomplished with oocytes that were lysed and clarified by centrifugation. Aliquots of lysate containing equal amounts of total protein and representing equal numbers of oocytes can be analyzed by 10% SDS-PAGE and immunoblotted with polyclonal antibodies specific for the phosphorylated form of MAP kinase. Where SIP is active, or analogues of SIP are active, MAP kinase is not phosphorylated, as compared to when SIP is antagonized or not expressed in a system.

Similarly, analysis of germinal vessicle breakdown, or maturation, of oocytes can be accomplished in oocytes by injecting SIP cRNA, treating with insulin, and scoring for maturation 8–24 hours later. Alternatively, SIP and p110* cRNA can be co-injected, and oocytes scored for germinal vessicle breakdown 8–48 hours later. When SIP is active, maturation in response to insulin or expression of p110* is inhibited, as compared to when SIP is antagonized or not expressed in a system.

Use of SIP

Discovery that SIP is an SH2 domain-containing protein makes SIP an important signaling molecule. The activity of SIP includes becoming tyrosine phosphorylated and binding the PTB domain of SHC in response to activation of hematopoetic cells. SIP is a phosphatidylinositol- and inositol- polyphosphate 5-phosphatase with specificity in vitro for substrates phosphorylated at the 3' position. Phosphatidylinositol 3'-kinase (PI 3-kinase) is an enzyme that is involved in mitogenic signaling and whose phosphorylated lipid products are predicted to be substrates for SIP. To further elucidate the functional aspects of SIP, we show that SIP can modulate signaling by PI 3-kinase, and test this by in vivo by injecting SIP cRNAs into Xenopus oocytes. SIP reduced germinal vesicle breakdown (GVBD) induced by expression of a constitutively activated form of PI 3-kinase (p110*; p110* is described in U.S. Ser. No. 60/017693 filed in 1996) and blocked GVBD induced by insulin. SIP had no effect on progesterone-induced GVBD. Catalytically inactive SIP had little effect on insulin- or PI 3-kinase-induced GVBD. Expression of SIP, but not catalytically inactive SIP, also blocked insulin-induced MAP kinase phosphorylation in oocytes. SIP specifically reduced the level of phosphatidylinositol (3,4,5) triphosphate (PtdIns(3,4,5)P$_3$) generated in oocytes in response to insulin stimulation. Although the invention is not limited to theories of how the invention works, these results taken together strongly suggest that phosphatidylinositol 5-phosphatases can inhibit specific signaling pathways in vivo by hydrolyzing a product of PI 3-kinase. Further, our data suggest that the generation of PtdIns(3,4,5)P$_3$ by PI 3-kinase is necessary for insulin-induced GVBD in Xenopus oocytes.

SIP is tyrosine phosphorylated and binds the PTB domain of SHC in a variety of activated hematopoetic cell lines, but not in quiescent cells. SIP also contains proline-rich motifs which bind to the SH3 domains of GRB2. SIP is a member of the inositol polyphosphate 5-phosphatase family which hydrolyzes the 5' phosphate from both inositol- and phosphatidylinositol- polyphosphates. SIP has a striking substrate specificity in vitro for those inositol and phosphatidylinositols which are also phosphorylated at the 3' position.

Therefore, PtdIns(3,4,5)$P_3$, a known product of PI 3-kinase in vivo, would be predicted to be a substrate for the enzymatic activity of SIP. Additional members of the inositol polyphosphate 5-phosphatase family have been recently identified that are specific for PtdIns(3,4,5)$P_3$ and form signal transduction complexes in cells as described in Jackson et al, *EMBO* 14:4490–4500 (1995) and Liu et al, *J. of Biol Chem.* in press (1996). Thus, hydrolysis of PI 3-kinase products by phosphatidylinositol polyphosphate 5-phosphatases may be a general mechanism for the regulation of PI 3-kinase effects, although the invention is not limited to theories of mechanism.

Towards elucidating a mechanism of action for SIP, we tested the hypothesis that phosphatidylinositol polyphosphate 5-phosphatases like SIP may regulate PI 3-kinase activity in vivo by injecting SIP cRNAs into Xenopus oocytes. We show that SIP inhibits germinal vesicle breakdown induced by a constitutively activated PI 3-kinase. Further, we show that SIP blocks insulin-induced GVBD and phosphorylation of MAP kinase, processes which are thought to be mediated by PI 3-kinase in oocytes. Finally, we show directly that SIP reduces PtdIns(3,4,5)$P_3$ produced in vivo. The data we generated supports the theory that SIP is a regulator of PI 3-kinase.

We previously reported that the human Signaling Inositol Polyphosphate 5-Phosphatases (SIPs) represent a family of molecules which are likely to be splice variants of the same gene. We postulated that the full-length form of SIP corresponded to a 145 kDa protein, SIP-145, based on the existence of a open reading frame without termination cordons 5' to the first methionine codon (methionine 41) in the longest SIP cDNA we cloned. SIP has been variously reported to have a molecular mass of 130, 140, 145 or 150 kDa(7, 18, 22). To better characterize the full-length form of SIP for subsequent experiments, lysates of unstimulated BAL17 B cells and anti-SHC immunoprecipitates of activated BAL17 cell lysates were immunoblotted with anti-SIP antisera. The largest protein specifically recognized by anti-SIP antisera migrated at an apparent molecular weight of approximately 130–135 kDa, as measured by quantitative comparison to molecular weight standards, and migrated significantly faster than a known 148 kDa protein, phospholipase C-gamma. This suggested that no 145 kDa form of SIP protein exists in these cells. Further, because translation starting at methionine 41 would produce a protein of predicted molecular weight of 133 kDa, this suggested that methionine 41 is the translation start site for the largest form of SIP. To investigate further, recombinant SIP protein corresponding to residues 41–976 was expressed in COS 6M cells. This recombinant SIP migrated at the exact same apparent molecular weight as the largest form of endogenous SIP present in either lysates or anti-SHC immunoprecipitates from B cells. These results strongly suggest that full-length SIP corresponds to SIP-130, contains residues 41–976 and has an apparent molecular mass of approximately 130–135 kDa. This form of SIP was therefore used in subsequent experiments. Attempts to directly sequence the NH2-terminus of the largest form of SIP protein purified from BAL17 B cells were unsuccessful, presumably because the NH2-terminus was blocked. We have observed that both recombinant SIP expressed in COS cells and endogenous SIP from B cells is often seen as a doublet on immunoblots. The lower form may represent a degradation product of the larger form, the product of translation from an internal methionine, or a splice variant. The lower form migrates at an apparent molecular weight of 125 kDa, and is referred to as p125, or SIP-125.

SIP was originally identified as an inositol- and phosphatidylinositol-polyphosphate 5-phosphatase by the presence of sequence motifs homologous to other inositol polyphosphate 5-phosphatases. These sequences are presumed to constitute part of the catalytic domain, but mutagenesis studies of SIP to demonstrate this directly have not been reported. We wished to generate a mutant SIP protein which is catalytically inactive to use as a control in subsequent experiments. We therefore generated SIP constructs with point mutations or deletions within these conserved motifs and tagged with the influenza hemagglutinin (HA) epitope. The mutant proteins were expressed in COS cells, immunoprecipitated with anti-HA antibodies, and tested for inositol polyphosphate 5-phosphatase activity. SIP proteins with a substitution of alanine for aspartic acid 460 (D460A SIP), or with a deletion of amino acids 454–468 (SIP/EIP) were expressed equally well as wild-type SIP, but contained no detectable inositol polyphosphate 5-phosphatase activity. This experiment demonstrates directly that the these residues are necessary for SIP catalytic activity and support the hypothesis that the LPSWCDRVL (SEQ ID No. 33) motif comprises part of the catalytic center of inositol polyphosphate 5-phosphatases.

The identification of a family of phosphatidylinositol polyphosphate 5-phosphatases which are specific for 3'-phosphorylated substrates in vitro, has suggested a novel mechanism for the regulation of PI 3-kinase signaling. However, the activity of these enzymes in vivo has not been demonstrated, nor is it known whether they would potentiate or inhibit signaling by PI 3-kinase. We have demonstrated that one member of this family, SIP, can inhibit PI 3-kinase effects in vivo. Using a constitutively activated form of PI 3-kinase, p110*, we showed that SIP inhibits oocyte maturation induced by PI 3-kinase in the absence of added growth factors or hormones. Further, SIP blocks insulin-induced phosphorylation of MAP kinase and GVBD, processes which are thought to be mediated by PI 3 kinase in oocytes. SIP did not effect GVBD induced by progesterone, demonstrating that the effect of SIP is specific. The lack of an effect of SIP on progesterone-induced GVBD is consistent with a report that progesterone-induced oocyte maturation is not inhibited by the PI 3-kinase inhibitor wortmannin and does not require PI 3-kinase activation.

The ability of SIP to inhibit insulin and PI 3-kinase signaling is likely to be due to hydrolysis of a biologically active product of PI 3-kinase, PtdIns(3,4,5)$P_3$. First, as mentioned above, SIP inhibited processes known to be dependent on PI 3-kinase activity. Second, mutant SIP proteins which were demonstrated to be catalytically inactive did not inhibit signaling by either insulin or p110*. Finally, we have shown directly that expression of SIP results in significant decreases in PtdIns(3,4,5)$P_3$ generated in vivo in response to either insulin treatment. Hydrolysis in vivo of PtdIns(3,4,5)$P_3$, but not PtdIns(4,5)$P_2$ (FIG. 6), is consistent with the substrate specificity of SIP previously defined in vitro. Taken together, these results suggest that generation of PtdIns(3,4,5)$P_3$ is necessary for GVBD induced by insulin, and that SIP inhibits signaling by hydrolyzing PtdIns(3,4,5)$P_3$. Direction injection into oocytes of PtdIns(3,4,5)$P_3$ generated in vitro with p110* did not induce GVBD. Because the amount of PtdIns(3,4,5)$P_3$ which can be generated in vitro by this method is limited, the dose of PtdIns(3,4,5)$P_3$ injected may have been insufficient to induce GVBD. Further, a single injection of PtdIns(3,4,5)$P_3$ may not mimic the kinetics of PtdIns(3,4,5)$P_3$ generated by p110* or in response to insulin.

Recently published data on the function of SIP in mammalian cells support the hypothesis that SIP is an inhibitor of signaling. It has been reported that SIP associates with the inhibitory FcgammaRIIB receptor in B cells and mast cells. Co-ligation of this receptor with FceRI or FcgammaRIII on mast cells inhibits degranulation, and co-ligation with the antigen receptor on B cells inhibits B cell activation. SIP bound to a 13 amino acid motif in the cytoplasmic domain of the FcgammaRIIB receptor which has been shown to be necessary for inhibitory signaling by FcgammaRIIB. It has also been reported that expression of SIP in myeloid cells results in growth inhibition. Our data demonstrate one mechanism by which SIP might inhibit signaling in these cells, and the invention is not limited by theory of how the invention may work.

The SH2 domain of SIP was neither necessary nor sufficient for inhibition of insulin signaling. These data exclude the possibility that the SH2 domain accounted for the inhibitory effect of SIP. In mammalian cells, the SH2 domain is likely to participate in targeting of SIP to signaling complexes. The absence of a requirement for the SH2 domain for SIP activity in oocytes likely reflects either the effect of over-expression of SIP, or the absence of the endogenous target of the SH2 domain in oocytes. In addition to the SH2 domain, SIP contains binding sites for the PTB domain of SHC and for the SH3 domains of GRB2. Formation of signal complexes may regulate SIP activity by changing its sub-cellular localization or by bringing SIP into contact with regulatory molecules.

In conclusion, we have shown that a phosphatidylinositol polyphosphate 5-phosphatase can inhibit biological effects mediated by PI 3-kinase. We propose that this family of enzymes can participate in the downregulation of PI 3-linase-mediated signaling during mitogenesis, transformation and immune cell function. The nucleic acid constructs that contain the novel polypeptide coding sequence ("SIP coding sequence"), and variants thereof derived from SIP, (for purposes of this invention, also called "the SIP coding sequence"), with or without a signal sequence, can be used in a gene therapy protocol by delivery in gene delivery vehicles to replace cells and tissues lacking in SIP activity or activity of a polypeptide from the inositol polyphosphate 5-phosphatase family, for control of abnormal cell growth or other cellular responses by administration via gene therapy of recombinant SIP, or a SIP variant or analogue, or a signaling incompetent variant that acts as an antagonist or competitor of native or fully functional SIP. A gene therapy protocol can be designed to effect modulation of a biological pathway, where expression of a modulator of a signaling pathway is accomplished, for example a dominant negative repressor of a signaling pathway, including a modulator modulating such pathways as, for example, the ras pathway, MAP kinase pathway, the PI 3-kinase pathway, or a pathway mediated by the interaction of SIP with another protein. The gene delivery vehicle containing a modulator of a SIP-related pathway can be accomplished by in vivo expression of SIP or a derivative of SIP.

Gene therapy strategies for delivery of such constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

Generally, for delivery using viral vectors, any of a number of viral vectors can be used, as described in Jolly, *Cancer Gene Therapy* 1: 51–64 (1994). For example, the SIP coding sequence can be inserted into plasmids designed for expression in retroviral vectors, as described in Kimura et al., *Human Gene Therapy* (1994) 5: 845–852, adenoviral vectors, as described in Connelly et al., *Human Gene Therapy* (1995) 6: 185–193, adeno-associated viral vectors, as described in Kaplitt et al., *Nature Genetics* (1994) 6: 148–153 and sindbis vectors. Promoters that are suitable for use with these vectors include the Moloney retroviral LTR, CMV promoter and the mouse albumin promoter. Replication incompetent free virus can be produced and injected directly into the animal or humans or by transduction of an autologous cell ex vivo, followed by injection in viva as described in Zatloukal et al., *Proc. Natl. Acad. Sci. USA* (1994) 91:5148–5152.

The native or altered SIP coding sequence can also be inserted into plasmid for expression of the SIP polypeptide in vivo or ex vivo. For in vivo therapy, the coding sequence can be delivered by direct injection into tissue or by intravenous infusion. Promoters suitable for use in this manner include endogenous and heterologous promoters such as CMV. Further, a synthetic T7T7/T7OB promoter can be constructed in accordance with Chen et al. *Nucleic Acids Res.* 22: 2114–2120 (1994), where the T7 polymerase is under the regulatory control of its own promoter and drives the transcription of the SIP coding sequence, which is also placed under the control of a T7 promoter. The coding sequence can be injected in a formulation comprising a buffer that can stabilize the coding sequence and facilitate transduction thereof into cells and/or provide targeting, as described in Zhu et al., *Science* (1993) 261: 209–211.

Expression of the SIP coding sequence in vivo upon delivery for gene therapy purposes by either viral or non-viral vectors can be regulated for maximal efficacy and safety by use of regulated gene expression promoters as described in Gossen et al., *Proc. Natl. Acad. Sci. USA* (1992) 89:5547–5551. For example, the SIP coding sequence can be regulated by tetracycline responsive promoters. These promoters can be regulated in a positive or negative fashion by treatment with the regulator molecule.

For non-viral delivery of the SIP coding sequence, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu and Wu, *J. Biol. Chem.* (1987) 262: 4429–4432; insulin, as described in Hucked et al., *Biochem. Pharmacol.* 40: 253–263 (1990); galactose, as described in Plank et al., *Bioconjugate Chem.* 3:533–539 (1992); lactose, as described in Midoux et al., *Nucleic Acids Res.* 21: 871–878 (1993); or transferrin, as described in Wagner et al., *Proc. Natl. Acad. Sci. USA* 87:3410–3414 (1990). Other delivery systems include the use of liposomes to encapsulate DNA comprising the SIP gene under the control of a variety of tissue-specific or ubiquitously-active promoters, as described in Nabel et al., *Proc. Nat. Acad. Sci. USA* 90: 11307–11311 (1993), and Philip et al., *Mol. Cell Biol.* 14: 2411–2418 (1994). Further non-viral delivery suitable for use includes mechanical delivery systems such as the biolistic approach, as described in Woffendin et al., *Proc. Natl. Acad. Sci. USA* (1994) 91(24): 11581–11585. Moreover, the SIP coding sequence and the product of expression of such can be delivered through deposition of photopolymerized hydrogel materials. Other conventional methods for gene delivery that can be used for delivery of the SIP coding sequence include, for example, use of hand held gene transfer particle gun, as described in U.S. Pat. No. 5,149,655; use of ionizing radiation for activating transferred gene, as described in U.S. Pat. No. 5,206,152 and PCT application WO 92/11033.

Application of gene therapy technology with regard to SIP and its analogues or variants can be made in disease states where, for example, activity of any of the inositol polyphosphate 5-phosphatases is deficient, including, for example, a deficiency in activity of SIP. It is also conceived by the inventors that gene therapy using SIP and its analogues or variants is appropriate when treating conditions of abnormal cell growth where, for example, in vivo expression of SIP competitors, antagonists or dominant negatives interrupts the normal function of SIP and so interrupts the signaling pathways that SIP is a part of, and the cellular responses that result from these pathways, including but not limited to cellular proliferation.

In general, gene therapy can be applied according to the invention in all situations where SIP acts to modulate a signaling pathway, including potentiation, activation or inhibition of the pathway, by administering according to a gene therapy protocol, of a sufficient amount of a SIP analogue, variant, or dominant negative, for example, for modulating the normal activity of SIP in a given signaling pathway. The signaling pathways that can be modulated by gene therapy according to the invention may include, but are not limited to, for example, the ras and PI 3-kinase pathways. The modulations achievable by gene therapy employing SIP include any modulation of any cellular response that is generated in part by the activity of SIP.

For treating disease states including diseases caused by deficiencies in a member of the inositol polyphosphate 5-phosphatase family such as, for example, Lowe's oculocerebralrenal disease, or also including diseases cause by cellular proliferation by a signaling pathway of which a component of the pathway is a member of the inositol polyphosphate 5-phosphatase family, gene therapy to replace a missing gene or to interrupt or modulate the activity of existing genes can be applied according to the invention. First, polynucleotide constructs including a coding sequence for the missing gene or active fragment or variant thereof, or for the inhibitor of the activity of a gene in the pathway sought to be modulated or interrupted, and regulatory sequences for expression in vivo are designed and assimilated. The construct is then administered by standard administration methods for gene therapy protocols.

For the purpose of the invention, based on the sequence and function of the novel polypeptides herein, assays can be developed for screening small molecule library pools for functional SIP, modulators, for example, inhibitors, antagonists, and agonists for use in controlling abnormal cell growth, for example, in tumor conditions or other conditions induced by uncontrolled abnormal cell growth along a signaling pathway responsible for cell proliferation, such as, for example, a ras pathway, a MAP kinase pathway or a PI 3-kinase pathway. Small molecule inhibitors can also be used to inhibit, for example, SIP activity for inhibiting other cellular or signal transduction activities attributable to SIP or other members of the inositol polyphosphate 5-phosphatase. These inhibitors, antagonists, or agonists are then administered to the animal, and in the case of cancer locally at the tumor site, for example, and can be administered with a pharmaceutically acceptable carrier, including, for example, liposomes compositions such as Depofoam™, and other carriers such as, for example, Focalgel™.

More specifically, gene therapy vehicles for delivery of constructs including a coding sequence of a therapeutic of the invention, to be delivered to the mammal for expression in the mammal, for example, a SIP coding sequence, or also including a nucleic acid sequence of all or a portion of SIP for delivery can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

Administration of a polynucleotide encoding SIP polypeptide for expression in the mammal in a gene therapy protocol, can be provided by a viral vector, including for example, a vector of a retrovirus, an adenovirus, an adeno-associated virus, a herpes virus, an alpha virus, for example a semiliki forest virus, a sindbis virus, including sindbis DNA or sindbis RNA, or ELVS DNA. Retroviral gene therapy is described in WO 91/02805, and EF 334 301, both incorporated by reference in full. The retroviral vectors described in these patent publications can be used for retroviral delivery of a polynucleotide sequence encoding a SIP, or a portion, fusion, variant, or derivative of a SIP, for expression in a mammal. For example, a polynucleotide encoding a SIP can be placed in a retroviral vector, for example, a retroviral vector derived from an adenovirus, an adeno-associated virus, a herpes virus, an alpha virus, an ELVS virus and a sindbis virus. The alpha virus retroviral vector can be derived from a semiliki forest virus. Standard techniques known in the art of retroviral vector gene delivery can be used to incorporate an appropriate SIP coding sequence, or fusion coding sequence for retroviral gene delivery to the mammal. Where the SIP is expressed in the mammal, it can be expressed as a biologically active portion, variant, derivative or fusion of a SIP polypeptide.

Polynucleotide sequences encoding SIP can be delivered by any gene delivery vehicle. The gene delivery vehicles can include, for example, naked plasmid DNA delivery by liposome or particle-mediated gene transfer, or delivery of a polynucleotide coding sequence in a viral or other vector. Polynucleotide delivery strategies for delivery of constructs including a coding sequence for expression in the mammal, can be administered by a gene therapy protocol, either locally or systemically. These constructs can utilize viral or non-viral vector approaches in in vivo or ex vivo modality. Ex vivo means a process whereby the cells of a mammal are removed and selected for those for transfection, the selected cells are made so that they will not replicate, and are transfected with the polynucleotide to be expressed. The transfected cells are then placed back in the mammal, and the polynucleotide is expressed in the mammal. Expression of a coding sequence can be induced using endogenous mammalian or heterologous promoters. In vivo delivery involves directly administering a polynucleotide sequence into the mammal in the region of target cells for expression, for example, in the region of proliferating cells. In a process facilitated by the gene delivery vehicle, the cells take up the polynucleotide. Expression of the coding sequence in vivo, whether the polynucleotide is directly injected, or whether cells that are removed and replaced after transfection are used, can be either constitutive or regulated.

The constructions and use of, for example, the retroviral or adenoviral or naked or lipid encased are known in the art as described in Roussel et al., *Nature* 325: 549 (1987). The effects of the gene therapy administration are expected to be dose related, and optimal dosage for a particular type of condition will have to be determined, as is appropriate for the particular disease, and may be influenced by such factors as the mammal's level of progression of the disease, and the mammal's responsiveness to an initial treatment. Gene therapy can be practiced according to the invention by delivery to a region in a mammal genes that are under regulatory control of appropriate regulatory sequences for transformation or infection of the cells in a particular region. Gene therapy can be practiced as follows using coding regions for any SIP therapeutic agent appropriate for treatment of the SIP related condition.

For delivery using viral vectors, any of a number of viral vectors conventional in the art can be used, as described in Jolly, *Cancer Gene Therapy* 1: 51–64 (1994). For example, the SIP coding sequence can be inserted into plasmids designed for expression in retroviral vectors, as described in Kimura et al., *Human Gene Therapy* (1994) 5: 845–852, adenoviral vectors, as described in Connelly et al., *Human Gene Therapy* (1995) 6: 185–193, adeno-associated viral vectors, as described in Kaplitt et al., *Nature Genetics* (1994) 6: 148–153 and sindbis vectors. Recombinant retroviruses and various uses thereof have been described in numerous references including, for example, Mann et al. (*Cell* 33:153, 1983), Cane and Mulligan (*Proc. Nat'l. Acad. Sci. USA* 81:6349, 1984), Miller et al., *Human Gene Therapy* 1:5–14, 1990, U.S. Pat. Nos. 4,405,712; 4,861,719; 4,980,289 and PCT Application Nos. WO 89/02,468; WO 89/05,349 and WO 90/02,806, all incorporated by reference in full.

Briefly, numerous retroviral gene delivery vehicles may be utilized within the context of the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860–3864, 1993; Vile and Hart, *Cancer Res.* 53:962–967, 1993; Ram et al., *Cancer Res.* 53:83–88, 1993; Takamiya et al., *J. Neurosci. Res.* 33:493–503, 1992; Baba et al., *J. Neurosurg.* 79:729–735, 1993 (U.S. Pat. No. 4,777,127, GB 2,200,651, EP 0,345,242 and WO91/02805).

Retroviral gene delivery vehicles of the present invention may be readily constructed from a wide variety of retroviruses, including for example, B, C, and D type retroviruses as well as spumaviruses and lentiviruses (see RNA Tumor Viruses, Second Edition, Cold Spring Harbor Laboratory, 1985). Retroviruses for the preparation or construction of retroviral gene delivery vehicles of the present invention include retroviruses selected from the group consisting of Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Also Murine Leukemia Viruses include 4070A and 1504A (Hartley and Rowe, *J. Virol.* 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-1 90). Such retroviruses may be readily obtained from depositories or collections such as the American Type Culture Collection ("ATCC"; Rockville, Md.), or isolated from known sources using commonly available techniques.

Any of the above retroviruses may be readily utilized in order to assemble or construct retroviral gene delivery vehicles given the disclosure provided herein, and standard recombinant techniques (e.g., Sambrook et al, *Molecular Cloning: A Laboratory Manual*, 2d ed., Cold Spring Harbor laboratory Press, 1989; Kunkle, *PNAS*82:488, 1985). In addition, within certain embodiments of the invention, portions of the retroviral gene delivery vehicles may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

Recombinant retroviruses may be made by introducing a vector construct as discussed above, into a cell (termed a "packaging cell") which contains those elements necessary for production of infectious recombinant retrovirus which are lacking in the vector construct. Packaging cell lines suitable for use with the above-described retrovector constructs may be readily prepared (see U.S. Ser. No. 08/240, 030, filed May 9, 1994; see also WO 92/05266), and utilized to create producer cell lines (also termed vector cell lines or "VCLs") for the production of recombinant vector particles.

A wide variety of retrovector constructs may be utilized within the present invention in order to prepare recombinant retroviruses. For example, retrovector constructs can be provided comprising a 5' LTR, a tRNA binding site, a packaging signal, one or more heterologous sequences, an origin of second strand DNA synthesis and a 3' LTR, wherein the vector construct lacks gag/pol or env coding sequences.

The construction of recombinant retroviral vectors is described in greater detail in an application entitled "Recombinant Retroviruses" (U.S. Ser. No. 07/586,603, filed Sep. 21, 1990, which is hereby incorporated by reference in full). These recombinant retroviral vectors may be used to generate transduction competent retroviral vector particles by introducing them into appropriate packaging cell lines (see U.S. Ser. No. 07/800,921, which is hereby incorporated by reference in its entirety).

Adenovirus vectors may also be readily prepared and utilized given the disclosure provided herein (see also Berkner, *Biotechniques* 6:616–627, 1988, and Rosenfeld et al., *Science* 252:431–434, 1991, WO 93/07283, WO 93/06223, and WO 93/07282, which are incorporated by reference in full).

Vector constructs of the present invention may also be utilized with other viral vectors, including for example poliovirus (Evans et al., *Nature* 339:385–388, 1989, and Sabin, *J. of Biol. Standardization* 1:115–118, 1973); rhinovirus (Arnold, *J. Cell. Biochem.* L401–405, 1990); pox viruses, such as canary pox virus or vaccinia virus (Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112 and 4,769,330; WO 89/01973); SV40 (Mulligan et al., *Nature* 277:108–114, 1979); influenza virus (Luytjes et al., *Cell* 59:1107–1113, 1989; McMicheal et al., *The New England Journal of Medicine* 309:13–17, 1983; and Yap et al., *Nature* 273:238–239, 1978); parovirus such as adeno-associated virus (Samulski et al., *Journal of Virology* 63:3822–3828, 1989, and Mendelson et al., *Virology* 166:154–165, 1988); herpes (Kit, *Adv. Exp. Med Biol.* 215:219–236, 1989); SV40; HIV; measles (EP 0 440,219); corona virus and Sindbis virus (Xiong et al., *Science* 234:1188–1191, 1989; U.S. Pat. Nos. 5,091,309 and 5,217,879). Other adenoviral vectors are described in WO 95/14091, incorporated by reference in full.

Retrovirus and adenovirus vectors used for gene delivery are associated with certain complications and disadvantages. An alternative vector that is neither pathogenic or immunogenic can be a parvovirus adeno-associated virus (AAV). AAV has a smaller genome than adenovirus, most of which can be replaced by foreign DNA. Parvoviruses are small, icohedral viruses about 25 nm in diameter containing a single strand DNA genome of about 5 kb. They consist of two major classes: the dependoviuses, including AAV and its subtypes (AAV1, AAV2, AAV3, AAV4 and AAV5) and the autonomous parvoviruses. The wild-type (wt) AAV has been shown to integrate into human chromosome 19 in a site-specific manner, and it has been suggested that the AAV-based vector system may prove to be a safer alternative to the more commonly used retrovirus and adenovirus-based vectors; because approximately 90% of the human population is sero-positive for AAV, accidental infection by recombinant AAV is not likely to be problematic.

A disadvantage of AAV vector in some clinical indications is the generalized nature of AAV infection. Previous studies have indicated that AAV possesses a wide host range that transcends the species barrier. Additionally, AAV vectors can be formed from more than one AAV, forming a hybrid AAV vector, as described in U.S. Pat. No. 5,252,479.

Alpha viruses, including sindbis and ELVS viruses can be gene delivery vehicles for the invention. Alpha viruses are described in WO 94/21792, WO 92/10578 and WO 95/07994, all incorporated by reference in full. Several different alphavirus vector systems may be constructed and utilized within the present invention. Representative examples of such systems include those described within U.S. Pat. Nos. 5,091,309 and 5,217,879. Particularly preferred alphavirus vectors for use within the present invention include those which are described within WO 95/07994, and U.S. Ser. No. 08/405,627. Sindbis vector constructs, as well as numerous similar vector constructs, may be readily prepared essentially as described in U.S. Ser. No. 08/198,450. Exemplary Sindbis vector constructs, as well as numerous similar vector constructs, may be readily prepared essentially as described in U.S. Ser. No. 08/405,627, which is incorporated herein by reference in full.

As will be evident to one of ordinary skill in the art given the disclosure provided herein, when utilizing viral gene delivery vehicles, the efficiency of packaging and hence, viral titer, is to some degree dependent upon the size of the sequence to be packaged. Thus, in order to increase the efficiency of packaging and the production particle virus, additional non-coding sequences may be added to the gene delivery vehicle. Moreover, within certain embodiments of the invention it may be desired to increase or decrease viral titer. This increase or decrease may be accomplished by increasing or decreasing the size of the heterologous sequence, and hence the efficiency of packaging.

The coding sequence of, for example SIP or any of the other recombinant therapeutics listed herein, and chimeric and analog molecules thereof, can also be inserted into plasmids for expression of the polypeptide in vivo or ex vivo. For in vivo therapy, the coding sequence can be delivered by direct injection, or by delivery such as, for example, those systems described in U.S. Pat. Nos. 5,137,510, 5,213,570, and 5,269,326. Promoters suitable for use in this manner include endogenous and heterologous promoters such as those described herein. Gene delivery vehicles may be constructed to include a promoter such as SV40, cytomegalovirus ("CMV"), or an internal ribosomal binding site ("IRBS"). Further, a synthetic T7T7/T7 promoter can be constructed. Any promoter appropriate for the expression of the gene selected for the therapy is contemplated by the method of the invention. The coding sequence can be injected in a formulation comprising a buffer that can stabilize the coding sequence and facilitate transduction thereof into cells and/or provide targeting, as described in Zhu et al., *Science* (1993) 261: 209–211. Expression of such coding sequence can be induced using endogenous mammalian or heterologous promoters. Expression of the coding sequence in vivo can be either constitutive or regulated.

Expression of the coding sequence of a desired polypeptide or replication of a ribozyme or antisense polynucleotide in vivo upon delivery for gene therapy purposes by either viral or non-viral vectors can be regulated for maximal efficacy and safety by use of regulated gene expression promoters as described in Gossen et al., *Proc. Natl. Acad Sci. USA* (1992) 89:5547–5551. For example, the polynucleotide transcription and/or translation can be regulated by tetracycline responsive promoters. These promoters can be regulated in a positive or negative fashion by treatment with the regulator molecule.

In addition to the above viral-based vectors, numerous non-viral gene delivery vehicles may likewise be utilized within the context of the present invention. Representative examples of such gene delivery vehicles include direct delivery of nucleic acid expression vectors, naked DNA alone (WO 90/11092), polycationic lipids and liposomes encapsulating nucleic acid (single or double stranded DNA or RNA) expression vectors, polycation condensed DNA linked or unlinked to killed adenovirus (Curiel et al., *Hum. Gene Ther.* 3:147–154, 1992), DNA linked to a ligand with or without one of the high affinity pairs described above (Wu et al, *J. of Biol. Chem* 264:16985–16987, 1989), and certain eukaryotic cells (e.g., producer cells—see U.S. Ser. No. 08/240/030, filed May 9, 1994, and U.S. Ser. No. 07/800, 921). All such DNA vectors can be delivered as a gene delivery vehicle where an initial RNA pol II transcription encodes a viral bacteriophage or other source RNA replicase and in the same or a separate transcript, an RNA message that can be amplified in the cytoplasm by the RNA replicase, encoding the desired gene to be explored for therapy (U.S. Ser. No. 08/404,796).

Naked DNA or nucleic acid molecules are also suitable for use as gene delivery vehicles within the present invention (WO 90/11092). Such gene delivery vehicles may be either DNA or RNA and, in certain embodiments, are linked to killed adenovirus (Curiel et al., *Hum. Gene. Ther.* 3:147–154, 1992). Other suitable vehicles include DNA-ligand (Wu et al., *J. Biol. Chem.* 264:16985–16987, 1989), lipid-DNA combinations (Felgner et al., *Proc. Natl. Acad. Sci. USA* 84:7413 7417, 1989), liposomes (Wang et al., *Proc. Natl. Acad. Sci.* 84:7851–7855, 1987) and microprojectiles (Williams et al., *Proc. Natl. Acad. Sci.* 88:2726–2730,1991).

In addition, one can increase the efficiency of naked DNA uptake into cells by coating biodegradable latex beads with naked DNA. This approach takes advantage of the fact that latex beads, when incubated with cells in culture, are efficiently transported and concentrated in the perinuclear region. The beads will then be transported into cells when injected into muscle. DNA coated latex beads will be efficiently transported into cells after endocytosis is initiated by the latex beads, and thus increase the gene transfer and expression efficiency of this method. This method may be improved further by treatment of the beads to increase their hydrophobicity and thereby facilitate the disruption of the endosome and release of the DNA into the cytoplasm.

For non-viral delivery of the coding sequence, the sequence can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al.,, *Proc. Natl. Acad Sci. USA* (1994) 91(24): 11581–11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT application WO 92/11033. The aforementioned are not to the exclusion of additional means of facilitating of nucleic acid uptake that rely on nucleic charge neutralization or fusion with cell membranes or facilitate uptake, for example.

Polycationic molecules, lipids, liposomes, polyanionic molecules, or polymer conjugates conjugated to the polynucleotide can facilitate non-viral delivery of DNA or RNA. For example, polycationic agents for gene delivery include: polylysine, polyarginine, polyornithine, and protamine. Other examples include histones, protamines, human serum albumin, DNA binding proteins, non-histone chromosomal proteins, coat proteins from DNA viruses, such as φX174, transcriptional factors also contain domains that bind DNA and therefore may be useful as nucleic aid condensing agents, for example, C/CEBP, c-jun, c-fos, AP-1, AP-2, AP-3, CPF, Prot-1, Sp-1, Oct-1, Oct-2, CREP, and TFIID contain basic domains that bind DNA sequences. Organic polycationic agents include: spermine, spermidine, and purtrescine. The dimensions and of the physical properties of a polycationic agent can be extrapolated from the list above, to construct other polypeptide polycationic agents or to produce synthetic polycationic agents.

Polypeptides can be incorporated into the polycationic agents. In addition, lipoproteins can be incorporated into the polycationic agent, such as low density lipoprotein, high density lipoprotein, or very low density lipoprotein. Mutants, fragments, or fusions of these proteins can also be used. Other groups that can be incorporated include without limitation: hormones, steroids, androgens, estrogens, thyroid hormone, or vitamins, folic acid. Also, the polycationic agents of the instant invention can be chemically conjugated with polyalkylene glycol.

A solid phase method for the synthesis of N- substituted glycines or NSGs can be used which is generally applicable for a wide variety of side-chain substituents. A method of synthesis is to assemble the monomer from two submonomers in the course of extending a polymer comprising a NSG monomer. This technique is described in PCT WO94/06451. The NSGs can also be considered to be an alternating condensation of copolymer of an acylating agent and an amine.

The polycationic agent/polynucleotide complexes, whether or not encapsulated in liposomes, may be administered in pharmaceutical compositions. The pharmaceutical compositions will comprise therapeutically effective amount of nucleic acids. An effective dose for DNA delivery is from about 0.01 mg/ kg to 50 mg/kg or 0.05 mg/kg to about 10 mg/kg of the DNA constructs in the individual to which it is administered.

Additional agents can be included with the desired polynucleotides to be delivered, for delivery in either in a gene therapy protocol, or in a nucleic acid vaccination protocol. These additional agents can facilitate, for example, endocytosis of the desired nucleic acids or aid binding of the nucleic acids to the cell surface. Polypeptides can facilitate DNA delivery and include, for example: asialoorosomucoid (ASOR); transferrin; asialoglycoproteins; antibodies; antibody fragments; ferritin; interleukins; interferons, granulocyte macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of plasmodium falcipauum known as RII. Certain hormones such as for example, steroids, androgens, estrogens, thyroid hormone, or the vitamin, folic acid, can aid in nucleic acid delivery. Also, polyalkylene glycol can be included, and mono-, di-, or polysaccharides can be included.

The desired polynucleotide can also be encapsulated in lipids or packaged in liposomes prior to delivery to the mammal. Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1–17; Straubinger et al., in METHODS OF ENZYMOLOGY (1983), Vol. 101, pp. 512–527.

Liposomal preparations for use in the instant invention include cationic (positively charged), anionic (negatively charged) and neutral preparations. Cationic liposomes have been shown to mediate intracellular delivery of plasmid DNA (Felgner et al., *Proc. Natl. Acad Sci. USA* (1987) 84:7413–7416); mRNA (Malone et al., *Proc. Natl. Acad Sci. USA* (1989) 86:6077–6081); and purified transcription factors (Debs et al., *J. Biol. Chem.* (1990) 265:10189–10192), in functional form.

Cationic liposomes are readily available. For example, N[1–2,3-dioleyloxy)propyl]-N,N,N-triethylammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413–7416). Other commercially available liposomes include transfectace (DDAB/DOPE) and DOTAP/DOPE (Boerhinger). Other cationic liposomes can be prepared from readily available materials using techniques well known in the art. See, e.g., Szoka et al., *Proc. Natl. Acad Sci. USA* (1978) 75:4194–4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512–527; Szoka et al., *Proc. Natl. Acad. Sci. USA* (1978) 75:4194–4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad.*

Sci. USA (1979) 76:3348); Enoch and Strittnatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al, *Science* (1982) 215:166.

In addition, lipoproteins can be included with the polynucleotide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Such mutants, fragments and fusions can be constructed by altering the polynucleotides encoding the desired lipoproteins by recombinant DNA techniques. See, for example, Sambrook et al., (1989) Molecular Cloning, A Laboratory Manual, 2d edition (Cold Spring Harbor Press, Cold Spring Harbor, N.Y.). These polynucleotides can be inserted into expression vectors and host cells can be utilized to produce the desired apoprotein. In addition, naturally occurring lipoproteins, mutants, fragments, and fusions can be chemically altered. For example, acetylated LDL has biological activity. Chemically modified lipoproteins can also be purchased from commercial suppliers, such as Biomedical Technologies, Inc., Stoughton, Mass., USA.

A polynucleotide binding molecule refers to those compounds that associate with polynucleotides, and the association is not sequence specific. For example, such molecules can (1) aid in neutralizing the electrical charge of polynucleotide, or (2) facilitate condensation of nucleotides, or (3) inhibit serum or nuclease degradation. Examples of polynucleotide binding molecules include: polylysine, polyarginine, polyornithine, and protamine. Examples of organic polycations include: spermine, spermidine, and purtrescine. Other examples include histones, protamines, human serum albumin, DNA binding proteins, non-histone chromosomal proteins, coat proteins from DNA viruses, such as $\phi$X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Examples of other positively charged moieties include polybrene, DEAE-dextran, and cationic lipids. Useful cationic lipids and liposomes are described above. Lipids and liposomes are not used in this aspect of the invention to encapsulate both polynucleotide and lipoprotein. The lipoprotein must be exposed to bind the its cell surface receptor. Other synthetic compounds that are capable of binding negatively charged polynucleotides are useful, such as polymers of N-substituted glycines.

Pharmaceutical Compositions

Within another aspect of the invention, pharmaceutical compositions are provided for any of the therapeutic agents of the invention, including polynucleotides, polypeptides and small molecules. Where a gene delivery vehicle is used, the pharmaceutical composition can comprise a recombinant viral vector as described above, in combination with a pharmaceutically acceptable carrier or diluent. Such pharmaceutical compositions may be prepared either as a liquid solution, or as a solid form (e.g., lyophilized) which is suspended in a solution prior to administration. In addition, the composition may be prepared with suitable carriers or diluents for either surface administration, injection, oral, or rectal administration. Pharmaceutically acceptable carriers or diluents are nontoxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2, and 150 mM NaCl. In this case, since the recombinant vector represents approximately 1 mg of material, it may be less than 1% of high molecular weight material, and less than 1/100,000 of the total material (including water). This composition is stable at −70° C. for at least six months.

Pharmaceutical compositions of the present invention may also additionally include factors which stimulate cell division, and hence, uptake and incorporation of a recombinant retroviral vector. Preserving recombinant viruses is described in U.S. applications entitled "Methods for Preserving Recombinant Viruses" (U.S. Ser. No. 08/135,938, filed Oct. 12, 1993) which is incorporated herein by reference in full.

All of the therapeutic agents that make up the proposed therapy of the invention can be incorporated into an appropriate pharmaceutical composition that includes a pharmaceutically acceptable carrier for the agent. The pharmaceutical carrier for the agents may be the same or different for each agent Suitable carriers may be large, slowly metabolized macromolecules such as proteins, polysaccharides, polylactic acids, polyglycolic acids, polymeric amino acids, amino acid copolymers, and inactive viruses in particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in REMINGTON'S PHARMACEUTICAL SCIENCES (Mack Pub. Co., N.J. 1991). Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier. The term "liposomes" refers to, for example, the liposome compositions described in U.S. Pat. No. 5,422,120, WO 95/13796, WO 94/23697, WO 91/14445 and EP 524,968 B1. Liposomes may be pharmaceutical carriers for the small molecules, polypeptides or polynucleotides of the invention, or for combination of these therapeutics.

Pharmaceutical compositions are provided comprising a recombinant retrovirus or virus carrying one of the above-described vector constructs, in combination with a pharmaceutically acceptable carrier or diluent. The composition may be prepared either as a liquid solution, or as a solid form (e.g., lyophilized) which is suspended in a solution prior to administration. In addition, the composition may be prepared with suitable carriers or diluents for either surface administration, injection, oral, or rectal administration.

Pharmaceutically acceptable carriers or diluents are nontoxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A vector or recombinant virus can be delivered in a pharmaceutical composition in 10 mg/ml mannitol, 1 mg/ml HSA, 20 mM Tris, pH 7.2, and 150 mM NaCl. In this case, since the recombinant vector represents approximately 1 g of material, it may be less than 1% of high molecular weight material, and less than 1/100,000 of the total material (including water). This composition is stable at −70° C. for at least six months.

The pharmaceutically acceptable carrier or diluent may be combined with the gene delivery vehicles to provide a composition either as a liquid solution, or as a solid form (e.g., lyophilized) which can be resuspended in a solution prior to administration. The two or more gene delivery vehicles are typically administered via traditional direct routes, such as buccal/sublingual, rectal, oral, nasal, topical, (such as transdermal and ophthalmic), vaginal, pulmonary, intraarterial, intramuscular, intraperitoneal, subcutaneous, intraocular, intranasal or intravenous, or indirectly. Non-parenteral routes are contemplated by the invention.

Any therapeutic of the invention, including, for example, polynucleotides for expression in the mammal, can be formulated into an enteric coated tablet or gel capsule according to known methods in the art These are described in the following patents: U.S. Pat. No. 4,853,230, EP 225, 189, AU 9,224,296, AU 9,230,801, and WO 92144,52. Such a capsule is administered orally to be targeted to the jejunum. At 1 to 4 days following oral administration expression of the polypeptide, or inhibition of expression by, for example a ribozyme or an antisense oligonucleotide, is measured in the plasma and blood, for example by antibodies to the expressed or non-expressed proteins.

The gene delivery vehicle can be introduced into a mammal, for example, by injection, particle gun, topical administration, parental administration, inhalation, or iontophoretic delivery, as described in U.S. Pat. No. 4,411,648 and U.S. Pat. No. 5,222,936, U.S. Pat. No. 5,286,254; and WO 94/05369.

The gene delivery vehicle may be administered at single or multiple sites to a mammal directly, for example by direct injection, or alternatively, through the use of target cells transduced ex vivo. The present invention also provides pharmaceutical compositions (including, for example, various adjuvants) suitable for administering the gene delivery vehicles.

A vector construct which directs the expression of a SIP can be directly administered to a site exhibiting a condition that can be modulated by SIP or a modulator of SIP, for example in organs of the body. Various methods may be used within the context of the present invention in order to directly administer the vector construct. For example, arteries which serve the region may be identified, and the vector injected into such an artery, in order to deliver the vector directly into the site. Similarly, the vector construct may be directly administered to the skin surface, for example, by application of a topical pharmaceutical composition containing the vector construct.

The SIP polynucleotide is placed into a vector construct which directs its expression. Within the context of the present invention, a "vector construct" is understood to refer to an assembly which is capable of directing the expression of the sequence(s) or gene(s) of interest. The vector construct must include transcriptional promoter element(s), and preferably includes a signal which directs polyadenylation. In addition, the vector construct must include a sequence which, when transcribed, is operably linked to the sequence (s) or gene(s) of interest and acts as a translation initiation sequence. Optionally, the vector construct may also include a selectable marker such as Neo, TK, hygromycin, phleomycin, histidinol, or DHFR, as well as one or more restriction sites and a translation termination sequence. In addition, if the vector construct is placed into a retrovirus, the vector construct must include a packaging signal, long terminal repeats (LTRs), and positive and negative strand primer binding sites appropriate to the retrovirus used (if these are not already present).

In a direct administration, combination therapeutic agents including SIP and other agents can be administered together. The co-administration can be simultaneous, achieved for example by placing polynucleotides encoding the agents in the same vector, or by putting the agents, whether polynucleotide, polypeptide, or other drug, in the same pharmaceutical composition, or by administering the agents in different pharmaceutical compositions injected at about the same time, and perhaps in the same location. If the co-administration is not simultaneous, for example, in the case of administration of the prodrug after administration of the prodrug activator, the second agent can be administered by direct injection as appropriate for the goals of the therapy. Thus, for example, in the case of an administration of a prodrug, the prodrug is administered at the same location as the prodrug activator. Thus, a co-administration protocol can include a combination of administrations to achieve the goal of the therapy. Further, the co-administration can include subsequent administrations as is necessary, for example, repeat in vivo direct injection administrations of a SIP polypeptide.

Within the context of the present invention, it should be understood that the removed cells may be returned to the same animal, or to another allogenic animal or mammal. In such a case it is generally preferable to have histocompatibility matched animals (although not always, see, e.g., Yamamoto et al., "Efficacy of Experimental HIV Vaccines," 1st International Conference of HIV Researchers, University of California at Davis, September 1991.

Cells may be removed from a variety of locations in the mammal. In addition, within other embodiments of the invention, a vector construct may be inserted into, for example, cells from the skin (dermal fibroblasts), or from the blood (e.g., peripheral blood leukocytes). If desired, particular fractions of cells such as a T cell subset or stem cells may also be specifically removed from the blood (see, for example, PCT WO 91/16116, an application entitled "Immunoselection Device and Method"). Vector constructs may then be contacted with the removed cells utilizing any of the above-described techniques, followed by the return of the cells to the warm-blooded animal, preferably to or within the vicinity of the region of interest.

For this and many other aspects of the invention, effectiveness of treating humans may first be tested in animal models.

The multiple gene delivery vehicles may be administered to animals or plants. In preferred embodiments, the animal is a warm-blooded animal, further preferably selected from the group consisting of mice, chickens, cattle, pigs, pets such as cats and dogs, horses, and humans.

Any therapeutic of the invention, including, for example, polynucleotides for expression in the mammal, or ribozymes or antisense oligonucleotides, can be formulated into an enteric coated tablet or gel capsule according to known methods in the art. These are described in the following patents: U.S. Pat. No. 4,853,230, EP 225,189, AU 9,224, 296, AU 9,230,801, and WO 92144,52. Such a capsule is administered orally to be targeted to the jejunum. At 1 to 4 days following oral administration expression of the polypeptide, or inhibition of expression by, for example a ribozyme or an antisense oligonucleotide, is measured in the plasma and blood, for example by use of antibodies to the expressed or non-expressed proteins.

Administration of a therapeutic of the invention, includes administering a therapeutically effective dose of the therapeutic, by a means considered or empirically deduced to be effective for inducing the desired, therapeutic effect in the mammal. Both the dose and the administration means can be determined based on the specific qualities of the therapeutic, the condition of the mammal, the progression of the disease, and other relevant factors. Administration for the therapeutic agents of the invention can include, for example, local or systemic administration, including for example parenteral administration, including injection, topical administration, oral administration, catheterization, laser-created perfusion channels, a particle gun, and a pump. Parenteral administration can be, for example, intravenous, subcutaneous, intradermal, or intramuscular, administration.

The therapeutics of the invention can be administered in a therapeutically effective dosage and amount, in the process of a therapeutically effective protocol for treatment of the mammal. The initial and any subsequent dosages administered will depend upon the mammal's age, weight, condition, and the disease, disorder or biological condition being treated. Depending on the therapeutic, the dosage and protocol for administration will vary, and the dosage will also depend on the method of administration selected, for example, local or systemic administration.

For polypeptide therapeutics, for example, SIP or a SIP modulator, the dosage can be in the range of about 5 $\mu$g to about 50 $\mu$g/kg of mammal body weight, also about 50 $\mu$g to about 5 mg/kg, also about 100 $\mu$g to about 500 $\mu$g/kg of mammal body weight, and about 200 to about 250 ug/kg. In all contexts, modulators of SIP can be, for example, agonists or antagonists of SIP activity.

For polynucleotide therapeutics, for example native or mutant SIP polypeptide, or a modulator of SIP polypeptide, depending on the expression of the polynucleotide in the mammal, for tissue targeted administration, vectors containing expressable constructs of coding sequences, or non-coding sequences can be administered in a range of about 100 ng to about 200 mg of DNA for local administration in a gene therapy protocol, also about 500 ng to about 50 mg, also about 1 ug to about 2 mg of DNA, about 5 ug of DNA to about 500 ug of DNA, and about 20 ug to about 100 ug during a local administration in a gene therapy protocol, and for example, a dosage of about 500 ug, per injection or administration.

Non-coding sequences that act by a catalytic mechanism, for example, catalytically active ribozymes may require lower doses than non-coding sequences that are held to the restrictions of stoichiometry, as in the case of, for example, antisense molecules, although expression limitations of the ribozymes may again raise the dosage requirements of ribozymes being expressed in vivo in order that they achieve efficacy in the mammal. Factors such as method of action and efficacy of transformation and expression are therefore considerations that will effect the dosage required for ultimate efficacy for DNA and nucleic acids. Where greater expression is desired, over a larger area of tissue, larger amounts of DNA or the same amounts readministered in a successive protocol of administrations, or several administrations to different adjacent or close tissue portions of for example, a tumor site, may be required to effect a positive therapeutic outcome.

Administration of a therapeutic of the invention, includes administering a therapeutically effective dose of the therapeutic, by a means considered or empirically deduced to be effective for inducing the desired therapeutic effect in the mammal. Both the dose and the administration means can be determined based on the specific qualities of the therapeutic, the condition of the mammal, the progression of the disease, and other relevant factors. Administration for the therapeutic agents of the invention can include, for example, local or systemic administration including injection, topical administration, oral administration, catheterization, mucosal, nasal, or inhalation administration, laser-created perfusion channels, a particle gun, and a pump. Parenteral administration can be, for example, intravenous, subcutaneous, intradermal, or intramuscular, administration.

The therapeutics of the invention can be administered in a therapeutically effective dosage and amount, in the process of a therapeutically effective protocol for treatment of the mammal. The initial and any subsequent dosages administered will depend upon the mammal's age, weight, condition, and the disease, disorder or biological condition being treated. Depending on the therapeutic, the dosage and protocol for administration will vary, and the dosage will also depend on the method of administration selected, for example, local or systemic administration.

In all cases, routine experimentation in clinical trials will determine specific ranges for optimal therapeutic effect, for each therapeutic, each administrative protocol, and administration to specific mammals will also be adjusted to within effective and safe ranges depending on the mammal condition and responsiveness to initial administrations.

Further objects, features, and advantages of the present invention will become apparent from the detailed description. It should be understood, however, that the detailed description, while indicating preferred embodiments of the invention, is given by way of illustration only, since various changes and modifications within the spirit and scope of the invention will become apparent to those skilled in the art from this detailed description. Also, the invention is not limited by any theories of mechanism of the method of the invention.

The present invention will now be illustrated by reference to the following examples which set forth particularly advantageous embodiments. However, it should be noted that these embodiments are illustrative and are not to be construed as restricting the invention in any way.

Further objects, features, and advantages of the present invention will become apparent from the detailed description. It should be understood, however, that the detailed description, while indicating preferred embodiments of the present invention, is given by way of illustration only, since various changes and modifications within the spirit and scope of the invention will become apparent to those skilled in the art from this detailed description.

The present invention will now be illustrated by reference to the following examples which set forth particularly advantageous embodiments. However, it should be noted that these embodiments are illustrative and are not to be construed as restricting the invention in any way. Further objects, features, and advantages of the present invention will become apparent from the detailed description. It should be understood, however, that the detailed description, while indicating preferred embodiments of the present invention, is given by way of illustration only, since various changes and modifications within the spirit and scope of the invention will become apparent to those skilled in the art from this detailed description.

EXAMPLE 1

Purification of SIP-130 and SIP-125 Polypeptides

BAL17 B cells were stimulated by crosslinking the B cell antigen receptor with anti-immunoglobulin M antibodies. The B cells were grown in modified DME/F12 media containing 6% fetal bovine serum, collected by centrifugation and stimulated in phosphate buffered saline (PBS), 250 μM sodium orthovanadate, and 1 mg of anti-immunoglobulin M antibody (Jackson Immunologicals, Inc.) per $10^9$ cells for 2 minutes at 37° C. The cell slurry was then diluted with ice-cold PBS/vanadate, centrifuged and the cell pellet flash frozen until use.

The cell pellets were thawed, dounce homogenized in 20 mM Tris pH 8.0, 0.5 mM vanadate, 500 μM PMSF, 1 μg/ml aprotinin, 5 μg/ml leupeptin (Buffer A), centrifuged and the supernatants applied at 0.8 ml/min to an 15 ml (1.0×1.3 cm) anti-phosphotyrosine antibody affinity column (PY20, Signal Transduction Laboratories, Lexington, Kenty.). The column was washed at 1.6 ml/min with Buffer A+0.1% triton x-100 until absorbance plateaued and then with Buffer A until absorbance baseline was zero. Protein was eluted with Buffer A containing 100 mM phenylphosphate at 0.13 ml/min and 0.5 ml fractions collected.

Column fractions were assayed by SDS-PAGE, transferred to nitrocellulose and incubated with $^{32}$P-labeled GST-SHC PTB domain fusion protein, as described in Kavanaugh, & Williams, Science 266: 1862–1865, 1994. Fractions containing p130 and p125 were then dialyzed against 20 mM Tris-HCL, pH 7.5, 2 mM Na Tungstate, 2 mM Na Arsenate, 1 mM benzamidine and 1 mM DTT (Buffer B), and loaded at 1 ml/min on a 5 ml Pharmacia Q FF anion exchange column.

Proteins were eluted with a 100 ml, 0 to 1M NaCl gradient in Buffer B, and 2 ml fractions assayed as above. The peak fractions were then pooled, concentrated using a centriprep concentrator and analyzed by 8% SDS-PAGE. Proteins were stained with Coomassie blue, and bands corresponding to p130 excised. p130 protein was then digested with endoproteinase Lys-C, and peptides purified and sequenced according to standard methods, as described in Matsudaira, P. (1993). A Practical Guide to Protein and Peptide Purification for Microsequencing (San Diego: Academic Press, Inc).

The partially purified protein of p130 was digested with endoproteinase Lys-C. The resulting peptides were then extracted, purified by standard methods including HPLC, and sequenced according to standard methods of peptide sequencing. Eight peptide samples were analyzed for amino acid sequencing. One sample had no identifiable sequence, and two were autolytic fragments of endoproteinase Lys-C. Of the 5 remaining p130 peptides, 4 contained sequences identical to the 110 kDa SIP-110 as indicated in (SEQ ID NO: 5), (SEQ ID NO: 6), (SEQ ID NO: 7), and (SEQ ID NO: 8). One of these four peptides contained an aspartic acid instead of the glutamic acid at position 839 of SIP-I 10 (sequence (SEQ ID NO: 8). One other peptide contained a unique sequence not found in sequence databases (SEQ ID No. 9 (mouse) and SEQ ID No. 13 (human)).

These results demonstrated that p130 has a high degree of similarity to the 110 kDa SIP-110, and is likely to be a member of the inositol polyphosphate 5-phosphatase family. The difference in molecular weights of SIP-110 and p130 demonstrate that they are not the same protein, though they may be splice variants of the same gene.

EXAMPLE 2

SIP-110 Antibodies Recognize SIP-130 and SIP-125

Rabbit antibodies were raised by standard techniques against three different epitopes of SIP-110 protein. The epitopes were residues 48–231 (antibody DP3), 232–500 (antibody DP5), and 891 to 969 (antibody 8727) of SIP-110. In cell lysates and in anti-SIP-110 immunoprecipitates from B cell extracts these antibodies recognized the 110 kDa SIP-110 as well as p125 and the 130 kDa SIP. All three anti-SIP-110 antibodies specifically recognized proteins of about 130–135 kDa and about 125 kDa in SHC immunoprecipitates from stimulated but not unstimulated B cells. Pre-immune and anti-SHC immunoprecipitates from unstimulated and activated B cells were immunoblotted with two different antibodies raised against separate epitopes of SIP-110 (DP3 and DP5). p125 and p130 SIP bands were absent when immunoblotted with pre-immune sera.

EXAMPLE 3

Enzymatic Activity of SIP

Inositol polyphosphate 5-phosphatases hydrolyze the 5 phosphate from $Ins(1,4,5)P_3$ and $Ins(1,3,4,5)P_4$, and a subset of these enzymes, including SIP-110, can remove the 5-phosphate from phosphatidylinositol polyphosphates. To determine whether SIP is also a functional inositol phosphatase, anti-SHC immunoprecipitates were assayed for their ability to hydrolyze inositol phosphates and phosphatidylinositol polyphosphates. An activity that hydrolyzed inositol 1,3,4,5 tetrakisphosphate ($Ins(1,3,4,5)P_4$) was detected in immunoprecipitates of SHC from activated B cells but not in immunoprecipitates from unstimulated cells, or in preimmune immunoprecipitates of SHC. No hydrolysis of $Ins(1,4,5,)P_3$ over background was detected in any of these samples, indicating that SIP is a functional inositol polyphosphate phosphatase with a preference for 3-phosphorylated substrates. Additionally, phosphatidylinositol 3,4,5, triphosphate was hydrolyzed to phosphatidylinositol 3,4, diphosphate in immunoprecipitates of SHC from activated B cells but not in immunoprecipitates from unstimulated cells, or in preimmune immunoprecipitates of SHC, indicating that SIP-130 and p125 are functional phosphatidyl inositol 5-phosphates with a preference for 3 phosphorylated substrates.

EXAMPLE 4

Cloning SIP-130 and SIP-N

Five p130 peptides (SEQ ID No.s 5,6,7,8, and 9) and three p125 peptides (SEQ ID No. 25, 26, and 27) were sequenced. Surprisingly, four p130 peptides (SEQ ID No. 5, 6, 7, and 8) and all three p125 peptides contained sequences identical to the 110-kDa SIP-110. One p130 peptide contained an aspartic acid instead of the glutamic acid at position 839 of SIP-110. One p130-derived peptide contained unique sequence not found in the sequence databases (SEQ ID No. 9). The p125 and p130 peptides were identical to widely separated portions of the SIP-110 sequence, suggesting that p125, p130 and SIP-110 are homologous over a large portion of the SIP-110 sequence.

These results demonstrated that p125 and p130 have a high degree of similarity to the 110 kDa SIP-110, and are likely to be inositol polyphosphate 5-phosphatases. Further the presence of unique sequence in p130 and the difference in molecular weights of SIP-110 and p125 and p130 demonstrate that they are not the same protein. Thus developed the names SIP-130 and SIP-125.

cDNAs of SIP-130 were obtained by probing a human lung cDNA library with probes derived from SIP-110 sequences. A 3537-bp partial cDNA of SIP-130 was obtained with an open reading frame of 1178 amino acids. The predicted amino acid sequence of this cDNA contains all the peptide sequences isolated from purified p125 and p130 proteins. Four out of 18 residues in one p130-derived peptide sequence differed from the corresponding predicted amino acid sequence based on the SIP-130 cDNA. Three of these residues represented conservative substitutions. This likely reflects species differences between the peptide, which was derived from the mouse p130 protein, and the SIP-130 cDNA, which was obtained from a human cDNA library.

Nucleotides 788 to 3537 of the SIP-130 partial cDNA were identical to nucleotides 37 to 2786 of SIP-110. This suggested that SIP-110 is a splice variant of SIP-130 which lacks the NH2 terminal region of p130. The presence of at least two bands on a Northern blot using a SIP-110 DNA probe supported this idea. Further, an in-frame ATG at nucleotide 122 of the SIP-130 cDNA is flanked by a consensus translation initiation sequence. Translation beginning at this site would produce a protein of approximate predicted molecular weight of 133 kDa, suggesting that SIP-130 results from initiation of translation at this codon.

The predicted amino acid sequence of SIP-130 contains a SH2 domain in the NH2-terminus which is not present in the SIP-110 cDNA. The 3' end of the SIP-130 cDNA is identical to SIP-110, and therefore contains several of the proline-rich sequence present in the COOH-terminus of SIP-110. Because the SIP-130 cDNA was incomplete at the 3' end, we cannot yet determine if the SIP-130 and SIP- 110 are completely identical in this region. However, the presence of an SH2 domain and proline-rich sequences in the SIP-130 sequence strongly implicate SIP 130 as an important signaling molecule.

An additional putative splice variant of SIP-130, called SIP-N, was identified by screening cDNA libraries with oligonucleotides corresponding to SIP-130 sequences. SIP-N begins at the same nucleotide as the SIP-130 partial cDNA clone described above, but has a stop codon prior to the beginning of the SIP-110 sequence. Therefore, SIP-N protein is predicted to contain the NH2-terminus of the SIP-130 protein, including the SH2 domain, but not any of the SIP-110 sequence. SIP-N also contains a deletion of nucleotides 470,471 and 472 of SIP-130 DNA, corresponding to amino acid 157. The SIP-N cDNA contains additional coding sequence at its 3' end which is not present in SIP-130, and predicts 12 amino acids at the COOH-terminus of SIP-N which are not present in SIP-130. Finally, SIP-N contains a 3' untranslated sequence ending with a poly A tail, demonstrating that it is a splice variant and not a cloning artifact.

EXAMPLE 5

SIP inhibits PI 3-kinase-induced Xenopus oocyte maturation

The specificity of SIP in vitro for 3'-phosphorylated phosphatidylinositols suggests that SIP may regulate signaling by PI 3-kinase. We asked whether expression of SIP protein is capable of either activating or inhibiting PI 3-kinase-dependent signaling in vivo. It has been previously demonstrated that a constitutively activated form of PI 3-kinase, known as p110*, induced germinal vesicle breakdown (GVBD) in Xenopus oocytes in the absence of added growth factors or hormones. We studied whether SIP modulated the effects of p110* in oocytes by co-injecting SIP and p110* cRNA. Injection of p110* cRNA resulted in GVBD, consistent with previously reported results. Injection of SIP cRNA alone did not induce GVBD. p110*-induced GVBD was significantly reduced by co-injection of SIP. The inhibition of PI 3-kinase signaling by SIP was not due to alterations in p110* protein expression. Further, catalytically inactive SIP, SIPÆIP, had little effect on GVBD induced by p110*. These experiments demonstrate that a biological effect of PI 3-kinase, oocyte maturation, can be inhibited in vivo by the enzymatic activity of SIP.

Xenopus laevis frogs were maintained as previously described in Wu et al, *Methods Cell Biol.* 36: 1–18 (1991). In some experiments, frogs were injected with 50 I.U. PMSG (CalBiochem) on the day prior to oocyte harvesting. Oocytes were surgically harvested as described and manually defolliculated under a dissecting microscope. Stage VI oocytes were selected as described in Dumont, *J. Morphol.* 136: 153–180 (1971), and maintained in MRS (modified Ringer's solution: 100 mM NaCl, 4 mM NaHCO$_3$, 1.8 mM KCL, 2 mM CaCl$_2$, 1 mM MgCl$_2$, 1 mg/ml bovine serum albumin) at 18–20° C. Small groups of oocytes were tested for insulin responsiveness by incubation in MRS containing 8 μM insulin for 4–8 hours at 22–25° C. If >60% germinal vesicle breakdown (GVBD) in response to insulin was observed, fresh oocytes from the same harvest were used for subsequent experiments.

Microinjection of cRNAs into oocytes was performed in MRS essentially as described in Muslin, et al. *Molecular and Cellular Biology* 13:4197–42022 (1993) 5–50 nl of distilled H$_2$O containing 25–50 ng of each cRNA, or H$_2$O alone as a control, was injected at the junction of the animal and vegetal poles. The oocytes were then incubated at 22–25° C. in modified Ringer's solution for 3–16 hr to allow for translation of the cRNA into protein. The oocytes were then treated with 8 μM insulin (in 50 mM HCl neutralized with an equal volume of 0.5 M NaHCO$_3$), 5 μg/ml progesterone or vehicle for 8–16 hr at room temperature and scored for GVBD, or lysed as described below. Results presented are representative of multiple independent experiments.

To generate the cRNAs, wild-type SIP and SIPÆIP were cloned into the pSp vector and cRNA generated by in vitro transcription as described in Muslin, et al. *Molecular and Cellular Biology* 13:4197–42022 (1993). SIP containing an inactivating point mutation in the SH2 domain (SIPÆSH2) was generated by a G-to-T transversion at nucleotide 213, which changes arginine 71 to a leucine. Constitutively active, farnesylated PI 3-kinase (p110*) was constructed with a myc epitope tag and cRNA generated as described (Hu, et al, *Science* 268:100–102 (1995) and Klippel, et al, *Molecular and Cellular Biology* 16:4117–4127 (1996). For analysis of p110* expression, equal numbers of oocytes were lysed in 10 μl/oocyte of lysis buffer by repeated pipeting, and lysates clarified by centrifugation, as above. Lysates were immunoprecipitated with anti-myc antibodies and immunoblotted with anti-p110 antibodies as described Klippel, et al, *Molecular and Cellular Biology* 16:4117–4127 (1996).

In this example, and the others that follow, analysis of proteins expressed in COS cells was accomplished as follows: wild-type human SIP (amino acids 41–976 as numbered in Kavanaugh, et al, *Current Biology* 6:438–445 (1995) tagged with the influenza hemagglutinin (HA) epitope at the NH2-terminus was cloned into the mammalian expression vector pCG(19). Catalytically inactive SIP was generated from pCGN-SIP by deleting nucleotides 1368–1412, representing amino acid residues 454–468 within the presumed inositol phosphatase catalytic domain (SIP/ÆIP) as described in Kavanaugh, et al, *Current Biology* 6:438–445 (1995) or Jefferson and Majerus. *J Biol Chem* 270:9370–7 (1995) or by changing nucleotides 1388–89 from A-C to C-A, which substitutes an alanine for aspartic acid 460 (D460A SIP). Constructs were expressed by transient transfection in COS 6M cells as described in Gorman, p. 143–190. In D. M. Glover (ed.), DNA cloning, a practical approach., vol. 2. IRL Press, Oxford (1985). 48 hours after transfection, the cells were lysed in lysis buffer (20 mM Tris-HCL, pH 8.0, 137 mM NaCl, 1% triton X-100, 10% glycerol, 1 mM sodium orthovanadate, 100 mM NaF, 10 mM sodium pyrophosphate, 1 mM EGTA, 1.5 mM $MgCl_2$, 1 mM phenylmethylsulfonyl fluoride, 0.15 units/ml aprotinin and 20 $\mu$M leupeptin) and clarified by centrifugation (15,000×g, 4° C., 10 minutes). SIPs were immunoprecipitated with anti-HA monoclonal antibodies (12CA5, Boehringer Mannheim), the pellets washed, and the immunoprecipitates analyzed for the ability to hydrolyze inositol (1,3,4,5) tetraphosphate as previously described in Kavanaugh, et al *Current Biology* 6:438–445 (1996). Aliquots of lysate were also immunoblotted with 12CAS or with anti-SIP antisera 8727(18) to determine protein expression.

EXAMPLE 6

SIP specifically blocks insulin-induced GVBD

Previous studies have demonstrated that insulin action on Xenopus oocytes requires activation of PI 3-kinase and the generation of 3'-phosphorylated phosphatidylinositols. Because SIP antagonizes PI 3-kinase effects in oocytes, we postulated that expression of SIP would inhibit insulin signaling in oocytes. Injection of SIP cRNA into oocytes blocked the ability of insulin to induce GVBD in multiple experiments. This effect was not due to a non-specific toxic effect of SIP, since the same amount of SIP cRNA had no effect on progesterone-induced GVBD, even when SIP protein was allowed to accumulate to high levels over 16 hours prior to treating the oocytes with progesterone. Further, the ability of SIP to inhibit insulin-induced GVBD was dependent on the enzymatic activity of SIP, since a catalytically inactive mutant SIP (SIPÆIP) had little or no effect.

The inability of the catalytically inactive SIP/ÆIP to inhibit insulin signaling suggested that expression of the SH2 domain of SIP, which is intact in this construct, is not sufficient for inhibition of insulin effects. We also investigated whether the SH2 domain of SIP is necessary for the ability of SIP to inhibit insulin signaling in this system. A mutant SIP cRNA was generated in which the arginine within the critical FLVRES motif of the SH2 domain was changed to an alanine. Similar mutations have been demonstrated in multiple systems to eliminate the ability of SH2 domains to interact with their tyrosine phosphorylated targets. Injection of SIP cRNA containing the inactivating SH2 domain mutation, but with an intact catalytic domain, inhibited insulin-induced GVBD almost as well as wild-type SIP. This experiment demonstrates that SIP SH2 domain function is not necessary for inhibition of insulin-induced GVBD in oocytes. Oocyte culture and cRNA generation was conducted as described in Example 5.

EXAMPLE 7

SIP blocks insulin-induced MAP kinase phosphorylation

Previous studies have suggested that, in Xenopus oocytes, activation of PI 3-kinase leads to activation of the ras pathway, including activation of ras, raf kinase and MAP kinase. These results would predict that injection of SIP would block the ability of insulin to activate MAP kinase. To investigate further, oocytes were injected with SIP or mutant SIP cRNAs, treated with insulin, and oocyte lysates analyzed for MAP kinase phosphorylation. As expected, insulin induced MAP kinase phosphorylation. Phosphorylation of MAP kinase by insulin was blocked by wild-type SIP, but not by catalytically inactive SIP. These results confirm biochemically the observation that SIP blocks insulin effects in oocytes, and provide further support for the hypothesis that SIP inhibits signaling by hydrolyzing and inactivating a product of PI 3-kinase. Oocyte culture and cRNA generation was conducted as described in Example 5. Analysis of MAP kinase phosphorylation was accomplished with Oocytes that were lysed by repeated pipeting in 10 $\mu$l per oocyte of lysis buffer and clarified by centrifugation as described previously. Aliquots of lysate containing equal amounts of total protein and representing equal numbers of oocytes were analyzed by 10% SDS-PAGE and immunoblotted with polyclonal antibodies specific for the phosphorylated form of MAP kinase (New England Biolabs).

EXAMPLE 8

Effect of SIP on PI 3-kinase products produced in vivo

To directly determine whether SIP hydrolyzes a product of PI 3-kinase produced in vivo, oocytes were injected with $H_2O$ or SIP cRNA and labeled with [$^{32}P$]orthophosphate. The oocytes were then stimulated with insulin for 10 minutes, the lipids extracted, and analyzed by thin layer chromatography and HPLC as described. Standards for PtdIns(3,4,5)$P_3$ were generated in vitro with purified p110*. Levels of PtdIns(3,4,5)$P_3$ increase in oocytes treated with insulin. Expression of SIP significantly reduces the amount of PtdIns(3,4,5)$P_3$ produced in response to insulin, but did not effect levels of PtdIns(4,5)$P_2$. This data is consistent with the in vitro activity of SIP and provides the first reported evidence that SIP is a PtdIns(3,4,5)$P_3$ 5-phosphatase in vivo as well as in vitro. Further, this experiment supports the hypothesis that SIP inhibits insulin signaling by hydrolyzing and inactivating a product of PI 3-kinase.

Analysis of PI 3-kinase products in vivo was accomplished using oocytes that were labeled with [$^{32}P$] orthophosphate and phospholipids were extracted and analyzed by TLC and HPLC essentially as previously described in Klippel, et al, *Molecular and Cellular Biology* 16:4117–4127 (1996) and Liu et at, *Molecular and Cellular Biology* 15:3563–3570 (1995). Briefly, groups of 20–25 oocytes were injected with $H_2O$ or with 50 ng of SIP cRNA, incubated for 2 hr at 25° C. in MRS and then incubated an additional 3 hours at 21° C. in 1 ml of MRS containing 1 mCi of [$^{32}P$]orthophosphate (9120 Ci/mmole, NEN). Oocytes were then washed three times in 1 ml MRS, and stimulated with 8 $\mu$M insulin in 0.5 ml MRS for 10 minutes at room temperature. The oocytes were placed on ice, the buffer aspirated and lysed in 750 μl of 1:1 (v/v) methanol:1N HCl with vigorous vortexing and repeated pipeting. 380 μl of chloroform was then added and the mixture vortexed for an additional 15 minutes to extract lipids. The extracts were then centrifuged (15,000×g, 2 minutes), the lower, chloroform phase removed to a new tube, the interface material and aqueous layer re-extracted with an equal volume of chloroform and the organic phases combined. The extracts were then separated on thin layer chromatography, de-acylated and analyzed by HPLC as described in Klippel, et al, *Molecular and Cellular Biology* 16:4117–4127 (1996) and Liu et al, *Molecular and Cellular Biology* 15:3563–3570 (1995). PtdIns(3,4,5)$P_3$ was identified using $^{32}$P-labeled standards generated with p110* as described in Klippel, et al, *Molecular and Cellular Biology* 16:41174127 (1996).

What is claimed is:

1. An antibody that binds specifically to a signaling inositol polyphosphate 5-phosphatase (SIP)-130 polypeptide, wherein the polypeptide comprises the amino acid sequence of SEQ ID NO: 15.

2. The antibody of claim 1, wherein the antibody is a single chain antibody or a humanized antibody.

3. A hybridoma that produces an antibody that binds specifically to signaling inositol polyphosphate 5-phosphatase (SIP)-130 polypeptide, wherein the polypeptide comprises the amino acid sequence of SEQ ID NO: 15.

4. A monoclonal antibody that binds specifically to signaling inositol polyphosphate 5-phosphatase (SIP)-130 polypeptide, wherein the polypeptide comprises the amino acid sequence of SEQ ID NO: 15.

5. A method for producing an antibody composition comprising:
  (a) providing a signaling inositol polyphosphate 5-phosphatase (SIP)-130 polypeptide, wherein the polypeptide comprises the amino acid sequence of SEQ ID NO: 15;
  (b) immunizing a mammal with said SIP-130 polypeptide; and
  (c) recovering serum from said immunized mammal that includes an antibody that binds specifically to said SIP-130 polypeptide.

6. A method for producing a hybridoma comprising:
  (a) providing a signaling inositol polyphosphate 5-phosphatase (SIP)-130 polypeptide, wherein the polypeptide comprises the amino acid sequence of SEQ ID NO: 15;
  (b) immunizing a mammal with the SIP-130 polypeptide;
  (c) isolating an antibody-producing cell from said immunized mammal; and
  (d) fusing said antibody-producing cell with a myeloma cell to form a hybridoma.

* * * * *